(12) United States Patent
Allison

(10) Patent No.: US 7,635,676 B2
(45) Date of Patent: *Dec. 22, 2009

(54) MODIFIED ANNEXIN PROTEINS AND METHODS FOR THEIR USE IN ORGAN TRANSPLANTATION

(75) Inventor: Anthony Allison, Belmont, CA (US)

(73) Assignee: Alavita Pharmaccuticals, Inc., Mountain View, CA (US)

( * ) Notice: Subject to any disclaimer, the term of this patent is extended or adjusted under 35 U.S.C. 154(b) by 289 days.

This patent is subject to a terminal disclaimer.

(21) Appl. No.: 11/267,837

(22) Filed: Nov. 3, 2005

(65) Prior Publication Data

US 2006/0105952 A1 May 18, 2006

Related U.S. Application Data

(63) Continuation-in-part of application No. 11/078,231, filed on Mar. 10, 2005, which is a continuation-in-part of application No. 10/080,370, filed on Feb. 21, 2002, now Pat. No. 6,962,903.

(60) Provisional application No. 60/270,402, filed on Feb. 21, 2001, provisional application No. 60/332,582, filed on Nov. 21, 2001, provisional application No. 60/552,428, filed on Mar. 11, 2004, provisional application No. 60/579,589, filed on Jun. 14, 2004.

(51) Int. Cl.
A61K 38/17 (2006.01)

(52) U.S. Cl. .............................. 514/12; 514/2; 530/350; 530/300; 435/7.1

(58) Field of Classification Search ........................ None
See application file for complete search history.

(56) References Cited

U.S. PATENT DOCUMENTS

| | | | |
|---|---|---|---|
| 4,002,531 A | 1/1977 | Royer et al. |
| 4,179,337 A | 12/1979 | Davis et al. |
| 4,507,229 A | 3/1985 | Bohn et al. |
| 4,732,891 A | 3/1988 | Maki et al. |
| 4,736,018 A | 4/1988 | Reutelingsperger et al. |
| 4,897,355 A | 1/1990 | Eppstein et al. |
| 4,937,324 A | 6/1990 | Fujikawa et al. |
| 4,965,251 A | 10/1990 | Stamatoyannopoulos |
| 5,066,787 A | 11/1991 | Reutelingsperger et al. |
| 5,066,788 A | 11/1991 | Reutelingsperger et al. |
| 5,097,019 A | 3/1992 | Lobermann et al. |
| 5,225,537 A | 7/1993 | Foster et al. |
| 5,229,367 A | 7/1993 | Perretti et al. |
| 5,258,497 A | 11/1993 | Reutelingsperger et al. |
| 5,290,915 A | 3/1994 | Nakao et al. |
| 5,296,467 A | 3/1994 | Reutelingsperger et al. |
| 5,360,789 A | 11/1994 | Nakao et al. |
| 5,484,711 A | 1/1996 | Wallner et al. |
| 5,589,395 A | 12/1996 | Romisch et al. |
| 5,591,633 A | 1/1997 | Saino et al. |
| 5,608,060 A | 3/1997 | Axworthy et al. |
| 5,612,460 A | 3/1997 | Zalipsky et al. |
| 5,632,986 A | 5/1997 | Tait et al. |
| 5,837,842 A | 11/1998 | Hauptmann et al. |
| 5,849,600 A | 12/1998 | Nixon et al. |
| 5,955,437 A | 9/1999 | Reutelingsperger |
| 5,968,477 A | 10/1999 | Kasina et al. |
| 6,169,078 B1 | 1/2001 | Hughes et al. |
| 6,171,577 B1 | 1/2001 | Reno et al. |
| 6,194,214 B1 | 2/2001 | Kraus |
| 6,242,570 B1 | 6/2001 | Sytkowski et al. |
| 6,312,694 B1 | 11/2001 | Thorpe et al. |
| 6,323,313 B1 | 11/2001 | Tait et al. |
| 6,358,508 B1 | 3/2002 | Ni et al. |
| 6,387,366 B1 | 5/2002 | Hurwitz et al. |
| 2002/0082623 A1 | 6/2002 | Osther |
| 2002/0088015 A1 | 7/2002 | Shi |
| 2002/0132256 A1 | 9/2002 | Cavanaugh |
| 2003/0027763 A1 | 2/2003 | Bennett et al. |
| 2003/0113330 A1 | 6/2003 | Uhal |
| 2003/0152513 A1 | 8/2003 | Blankenberg et al. |
| 2003/0175831 A1 | 9/2003 | Canton et al. |
| 2003/0211548 A1 | 11/2003 | Packard et al. |
| 2004/0002056 A1 | 1/2004 | Lorens et al. |
| 2004/0018590 A1 | 1/2004 | Gerngross et al. |
| 2004/0029151 A1 | 2/2004 | Mahadevappa et al. |
| 2004/0042959 A1 | 3/2004 | Montalto et al. |

(Continued)

FOREIGN PATENT DOCUMENTS

CN 1343777 4/2002

(Continued)

OTHER PUBLICATIONS

Rothhut et al. (1989) Biochem J. 263:929-935.
Seffernick et al. (2001) J. Bacteriology 183:2405-2410.
Wells (1990) Biochemistry 29:8509-8517.
Allan et al., Nature 295:612-613 (1982).
Bangham et al., J. Mol. Biol. 23:238-252 (1965).
Behr et al., Proc. Natl. Acad. Sci. USA 86:6982-6986 (1989).
Benz and Hofmann, Biol. Chem. 378:177-183 (1997).
Bernard et al., Am. Rev. Respir. Dis. 144:1095-1101 (1991).
Brittain et al., Blood 81:2137-2143 (1993).
Burger, FEBS Lett. 329:25-28 (1993).

(Continued)

*Primary Examiner*—Hope A Robinson
(74) *Attorney, Agent, or Firm*—Swanson & Bratschun, L.L.C.

(57) ABSTRACT

Modified annexin proteins, including a homodimer of human annexin V, are provided. Methods for their use, such as to prevent thrombosis without increasing hemorrhage and to attenuate ischemia-reperfusion injury (IPI), are also provided. The modified annexins bind phosphatidylserine (PS) on cell surfaces, thereby preventing the assembly of the prothrombinase complex. The modified annexin decreases the binding of leukocytes and platelets during post-ischemic reperfusion, thereby restoring microvascular blood flow and decreasing organ damage.

8 Claims, 11 Drawing Sheets

U.S. PATENT DOCUMENTS

| | | | |
|---|---|---|---|
| 2004/0171629 A1 | 9/2004 | Zervos |
| 2005/0053637 A1 | 3/2005 | Ma |
| 2005/0084547 A1 | 4/2005 | Subbiah |
| 2005/0130230 A1 | 6/2005 | Davalos et al. |
| 2005/0136455 A1 | 6/2005 | Lehmann et al. |
| 2005/0142657 A1 | 6/2005 | Grein et al. |
| 2005/0147692 A1 | 7/2005 | Roth |
| 2005/0208151 A1 | 9/2005 | Hurez et al. |
| 2005/0222030 A1 | 10/2005 | Allison |
| 2005/0244897 A1 | 11/2005 | Zeiher et al. |

FOREIGN PATENT DOCUMENTS

| | | |
|---|---|---|
| CN | 1401662 | 3/2003 |
| CN | 1404872 | 3/2003 |
| DE | 19541284 | 6/1995 |
| EP | 0318703 | 7/1989 |
| JP | 04198195 A | 7/1992 |
| JP | 5001096 | 1/1993 |
| JP | 116286 | 4/1994 |
| JP | 7072147 | 3/1995 |
| JP | 7072149 | 3/1995 |
| WO | WO8807576 | 10/1988 |
| WO | WO 91/07187 | 5/1991 |
| WO | WO9116882 | 11/1991 |
| WO | WO9207870 | 5/1992 |
| WO | WO 92/19279 | 11/1992 |
| WO | WO9401554 | 1/1994 |
| WO | WO 95/34315 | 12/1995 |
| WO | WO9603655 | 2/1996 |
| WO | WO 97/17084 | 5/1997 |
| WO | WO 97/24440 | 7/1997 |
| WO | WO9801563 | 1/1998 |
| WO | WO 98/04294 | 2/1998 |
| WO | WO 98/31383 | 7/1998 |
| WO | WO9829442 | 7/1998 |
| WO | WO9902992 | 1/1999 |
| WO | WO 99/19470 | 4/1999 |
| WO | WO9919470 | 4/1999 |
| WO | WO9924054 | 5/1999 |
| WO | WO9948916 | 9/1999 |
| WO | WO 0002587 | 1/2000 |
| WO | WO0010673 | 3/2000 |
| WO | WO0011026 | 3/2000 |
| WO | WO0012547 | 3/2000 |
| WO | WO0038517 | 7/2000 |
| WO | WO0111372 | 2/2001 |
| WO | WO0123426 | 4/2001 |
| WO | WO0133228 | 5/2001 |
| WO | WO0020769 | 3/2002 |
| WO | WO02067767 | 9/2002 |
| WO | WO02080754 | 10/2002 |
| WO | WO02087497 | 11/2002 |
| WO | WO 02087498 | 11/2002 |
| WO | WO02089657 | 11/2002 |
| WO | WO03103577 | 5/2003 |
| WO | WO03062264 | 7/2003 |
| WO | WO03079987 | 10/2003 |
| WO | WO03084333 | 10/2003 |
| WO | WO03093478 | 11/2003 |
| WO | WO03105814 | 12/2003 |
| WO | WO2004006963 | 1/2004 |
| WO | WO2004090554 | 10/2004 |
| WO | WO2004112717 | 12/2004 |
| WO | WO2004113561 | 12/2004 |
| WO | WO2005014801 | 2/2005 |
| WO | WO2005023096 | 3/2005 |
| WO | WO2005028490 | 3/2005 |
| WO | WP2005027965 | 3/2005 |
| WO | WO2005053744 | 6/2005 |
| WO | WO2005058351 | 6/2005 |
| WO | WO2005058352 | 6/2005 |
| WO | WO2005065418 | 7/2005 |
| WO | WO2005069000 | 7/2005 |
| WO | WO2005018436 | 8/2005 |
| WO | WO2005078124 | 8/2005 |
| WO | WO2005087275 | 9/2005 |
| WO | WO2005099744 | 10/2005 |
| WO | WO2005103720 | 11/2005 |

OTHER PUBLICATIONS

Campos et al., Biochemistry 37:8004-8008 (1998).
Chap et al., Biochem Biophys Res Commun 1988, 150:972-978.
Chow et al., J. Lab. Clin. Med. 135:66-72 (2000).
Database WPI, Section Ch, Weed 200036, Derwent Publications Ltd, London, Shanghai Inst Biochem Chinese Acad (2000) Abstract.
Delgado et al. (1992) Critical Rev in Therapeutic Drug Carrier Systems 9(3/4):249-304.
Felgner et al., Proc. Natl. Acad. Sci. USA 86: 7413-7417 (1987).
Fritsma, in Hemostasis and Thrombosis in the Clinical Laboratory (Corriveau, D.M. and Fritsma, G.A. Eds) J.P. Lipincott Co., Philadelphia (1989), pp. 92-124, 1991.
Fukunaga et al., Endocrinol. 115:757 (1984).
Funakoshi et al., Biochemistry 1987, 26:5572-5578.
Funakoshi et al., Biochemistry 26:8087-8092 (1987).
Green et al., Am. J. Hematol. 23:317 (1986).
Grundmann et al., Behring Inst Mitt 1988, 82:59-67.
Grundmann et al., Proc Natl Acad Sci USA 1988, 85:3708-3712.
Haupt et al., Crit. Care Med. 19:1339-1347 (1991).
Haut et al., J. Lab. Clin. Med. 82:44-53 (1973).
Heathcote et al., N. Engl. J. Med. 343:1673-1680 (2000).
Hebbel et al., Abstract. Clin. Res. 41:762A (1993).
Hermanson, Bioconjugate Techniques. NY, Academic Press (1996), pp. 173-176.
Huber et al., EMBO Journal 9:3867 (1990).
Iwasaki et al., J Biochem (Tokyo) 1987, 102:1261-1273.
Kang et al., Trends Cardiovasc. Med. 9:92-102 (1999).
Kaplan et al., Blood 57:199-202 (1981).
Kaplan et al., J Biol Chem 1988, 263:8037-8043.
Kassam et al. (1998) J Biol Chem 273(8):4790-4799.
Kim et al., Biochim. Biophys. Acta 728:339 (1983).
Knauf et al., J. Biol. Chem. 266:15064-15070 (1988).
Kuypers et al. (1996) Blood 87:1179-1187.
Lubin et al. (1981) J. Clin. Invest. 67:1643-1649.
Maurer-Fogy et al., Eur J Biochem 1988, 174:585-592.
Mayhew et al. (1984) Biochim. Biophys. Acta 775:169.
Meinkoth et al. (1984) Anal. Biochem. 138:267-284.
Merten et al. (1999) Circulation 99:2577-2582.
Murata et al. (1997) Nature 388:678-682.
Nakao et al., Chem Pharm Bull (Tokyo) 1990, 38:1957-1960.
Olson et al. (1979) Biochim. Biophys. Acta 557:9.
Pepinsky et al. (1988) J Biol Chem 263(22):10799-10811.
Pepinsky et al. (1989) Biochemistry Journal 263: 97-103.
Rand et al. (1998) Blood 92(5):1652-1660.
Reutelingsperger et al., Eur J Biochem 1985, 151:625-629.
Reutelingsperger et al., Eur J Biochem 1988, 173:171-178.
Richardson et al. (1979) Br. J. Haematol. 41:95.
Romisch et al. (1991) Thrombosis Research 61:93-104.
Romisch et al., Biochem J 1990, 272:223-229.
Romisch et al., Thromb Res 1990, 60:355-366.
Rothhut et al., Biochem J 1989, 263:929-935.
Schlaepfer et al., Proc Natl Acad Sci USA 1987, 84:6078-6082.
Setty et al. (2002) Blood 99:1564-1571.
Stratton et al. (1995) Circulation 92:3113-3121.
Strauss et al. (2000) J. Nucl. Med. 41 (5 Suppl.):149P.
Stuber et al. (1995) Peptide Research 8(2):78-85.
Sugihara et al. (1992) Blood 80:2634-2642.
Sun et al. (1993) Thromb. Res. 69:289 296.
Sytkowski et al. (1998) Proc Natl Acad Sci USA 95:1184-1188.
Szoka et al. (1978) Proc. Natl. Acad. Sci. 75:4194.
Tait et al. (1989) J. Biol. Chem. 264:7944-7949.
Tait et al. (1995) Journal of Biological Chemistry 270(27):21594-21599, Especially Abstract.

Thiagarajan and Benedict, Circulation 96:2339-2347 (1997).
Thiagarajan and Tait (1990) J. Biol. Chem. 265:17420-17423.
Van Heerde et al. (1994) Arteriosclerosis and Thrombosis 14:824-830.
Van Ryn-McKenna et al. (1993) Thromb. Haemost. 69:227-230.
Veronese et al. (2001) Biomaterials 22:405.
Zanma et al. (1991) J Biochem 110(6):868-872.
D'Amico et al. (2000) FASEB J 14:1867-1869.
Robinson et.al. (1998) PNAS USA 95:5929-5934.
Gerke et al. (2002) Physiol Rev 82:331-371.
D'Amico et al. (2001) FASEB J Article 10.
Peck-Radosavljevic et al. (2000) Thrombopoietin induces rapid resolution of thrombocytopenia after orthotopic liver transplantation through increased platelet production, Blood 95(3):795-801.
Allison, A-Geneseq, Direct Submission, Accession # AEH69391, May 18, 2006.

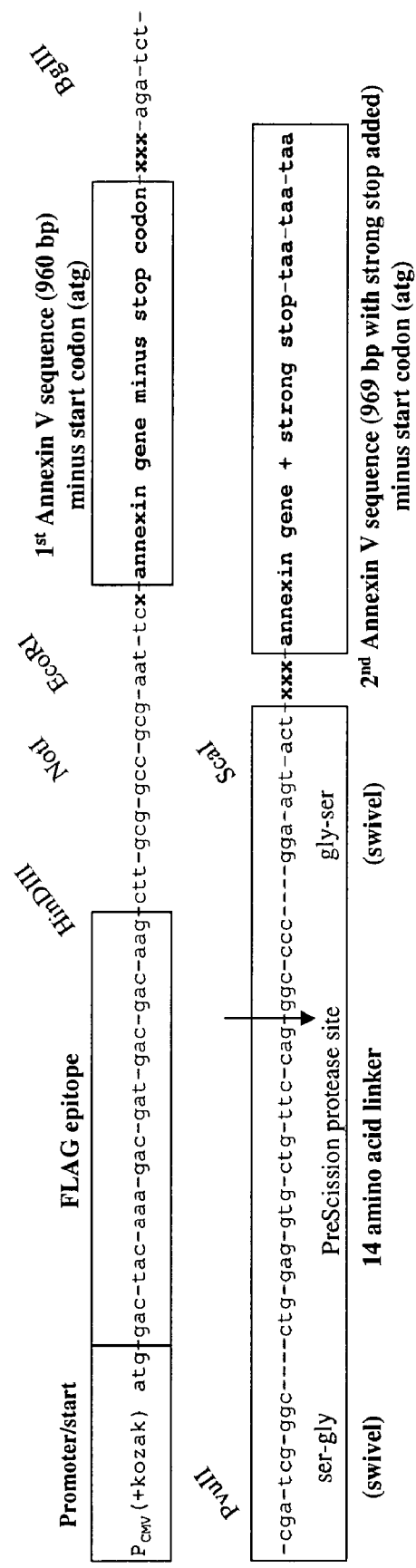

SEQUENCE LISTING

<160> NUMBER OF SEQ ID NOS: 23

<210> SEQ ID NO 1
<211> LENGTH: 957
<212> TYPE: DNA
<213> ORGANISM: Homo sapiens

<400> SEQUENCE: 1

```
gcacaggttc tcagaggcac tgtgactgac ttccctggat ttgatgagcg ggctgatgca      60
gaaactcttc ggaaggctat gaaaggcttg ggcacagatg aggagagcat cctgactctg     120
ttgacatccc gaagtaatgc tcagcgccag gaaatctctg cagcttttaa gactctgttt     180
ggcagggatc ttctggatga cctgaaatca gaactaactg gaaaatttga aaaattaatt     240
gtggctctga tgaaaccctc tcggctttat gatgcttatg aactgaaaca tgccttgaag     300
ggagctggaa caaatgaaaa agtactgaca gaaattattg cttcaaggac acctgaagaa     360
ctgagagcca tcaaacaagt ttatgaagaa gaatatggct caagcctgga agatgacgtg     420
gtggggaca cttcagggta ctaccagcgg atgttggtgg ttctccttca ggctaacaga     480
gaccctgatg ctggaattga tgaagctcaa gttgaacaag atgctcaggc tttatttcag     540
gctggagaac ttaaatgggg gacagatgaa gaaaagttta tcaccatctt tggaacacga     600
agtgtgtctc atttgagaaa ggtgtttgac aagtacatga ctatatcagg atttcaaatt     660
gaggaaacca ttgaccgcga gacttctggc aatttagagc aactactcct tgctgttgtg     720
aaatctattc gaagtatacc tgcctacctt gcagagaccc tctattatgc tatgaaggga     780
gctgggacag atgatcatac cctcatcaga gtcatggttt ccaggagtga gattgatctg     840
tttaacatca ggaaggagtt taggaagaat tttgccacct ctctttattc catgattaag     900
ggagatacat ctgggggacta taagaaagct cttctgctgc tctgtggaga agatgac       957
```

<210> SEQ ID NO 2
<211> LENGTH: 957
<212> TYPE: DNA
<213> ORGANISM: Homo sapiens
<220> FEATURE:
<221> NAME/KEY: CDS
<222> LOCATION: (1)..(957)

<400> SEQUENCE: 2

```
gca cag gtt ctc aga ggc act gtg act gac ttc cct gga ttt gat gag      48
Ala Gln Val Leu Arg Gly Thr Val Thr Asp Phe Pro Gly Phe Asp Glu
1               5                   10                  15 cgg gct gat gca gaa act ctt cgg aag gct atg aaa ggc ttg ggc aca      96
Arg Ala Asp Ala Glu Thr Leu Arg Lys Ala Met Lys Gly Leu Gly Thr
            20                  25                  30 gat gag gag agc atc ctg act ctg ttg aca tcc cga agt aat gct cag     144
Asp Glu Glu Ser Ile Leu Thr Leu Leu Thr Ser Arg Ser Asn Ala Gln
        35                  40                  45 cgc cag gaa atc tct gca gct ttt aag act ctg ttt ggc agg gat ctt     192
Arg Gln Glu Ile Ser Ala Ala Phe Lys Thr Leu Phe Gly Arg Asp Leu
    50                  55                  60 ctg gat gac ctg aaa tca gaa cta act gga aaa ttt gaa aaa tta att     240
Leu Asp Asp Leu Lys Ser Glu Leu Thr Gly Lys Phe Glu Lys Leu Ile
65                  70                  75                  80 gtg gct ctg atg aaa ccc tct cgg ctt tat gat gct tat gaa ctg aaa     288
Val Ala Leu Met Lys Pro Ser Arg Leu Tyr Asp Ala Tyr Glu Leu Lys
                85                  90                  95 cat gcc ttg aag gga gct gga aca aat gaa aaa gta ctg aca gaa att     336
His Ala Leu Lys Gly Ala Gly Thr Asn Glu Lys Val Leu Thr Glu Ile
            100                 105                 110 att gct tca agg aca cct gaa gaa ctg aga gcc atc aaa caa gtt tat     384
Ile Ala Ser Arg Thr Pro Glu Glu Leu Arg Ala Ile Lys Gln Val Tyr
        115                 120                 125 gaa gaa gaa tat ggc tca agc ctg gaa gat gac gtg gtg ggg gac act     432
Glu Glu Glu Tyr Gly Ser Ser Leu Glu Asp Asp Val Val Gly Asp Thr
    130                 135                 140 tca ggg tac tac cag cgg atg ttg gtg gtt ctc ctt cag gct aac aga     480
Ser Gly Tyr Tyr Gln Arg Met Leu Val Val Leu Leu Gln Ala Asn Arg
145                 150                 155                 160 gac cct gat gct gga att gat gaa gct caa gtt gaa caa gat gct cag     528
Asp Pro Asp Ala Gly Ile Asp Glu Ala Gln Val Glu Gln Asp Ala Gln
                165                 170                 175 gct tta ttt cag gct gga gaa ctt aaa tgg ggg aca gat gaa gaa aag     576
Ala Leu Phe Gln Ala Gly Glu Leu Lys Trp Gly Thr Asp Glu Glu Lys
            180                 185                 190 ttt atc acc atc ttt gga aca cga agt gtg tct cat ttg aga aag gtg     624
Phe Ile Thr Ile Phe Gly Thr Arg Ser Val Ser His Leu Arg Lys Val
        195                 200                 205 ttt gac aag tac atg act ata tca gga ttt caa att gag gaa acc att     672
Phe Asp Lys Tyr Met Thr Ile Ser Gly Phe Gln Ile Glu Glu Thr Ile
    210                 215                 220 gac cgc gag act tct ggc aat tta gag caa cta ctc ctt gct gtt gtg     720
Asp Arg Glu Thr Ser Gly Asn Leu Glu Gln Leu Leu Leu Ala Val Val
225                 230                 235                 240 aaa tct att cga agt ata cct gcc tac ctt gca gag acc ctc tat tat     768
Lys Ser Ile Arg Ser Ile Pro Ala Tyr Leu Ala Glu Thr Leu Tyr Tyr
                245                 250                 255 gct atg aag gga gct ggg aca gat gat cat acc ctc atc aga gtc atg     816
Ala Met Lys Gly Ala Gly Thr Asp Asp His Thr Leu Ile Arg Val Met
            260                 265                 270 gtt tcc agg agt gag att gat ctg ttt aac atc agg aag gag ttt agg     864
Val Ser Arg Ser Glu Ile Asp Leu Phe Asn Ile Arg Lys Glu Phe Arg
        275                 280                 285 aag aat ttt gcc acc tct ctt tat tcc atg att aag gga gat aca tct     912
Lys Asn Phe Ala Thr Ser Leu Tyr Ser Met Ile Lys Gly Asp Thr Ser
    290                 295                 300 ggg gac tat aag aaa gct ctt ctg ctg ctc tgt gga gaa gat gac         957
Gly Asp Tyr Lys Lys Ala Leu Leu Leu Leu Cys Gly Glu Asp Asp
```

```
Gly Asp Tyr Lys Lys Ala Leu Leu Leu Leu Cys Gly Glu Asp Asp
305                 310                 315

<210> SEQ ID NO 3
<211> LENGTH: 319
<212> TYPE: PRT
<213> ORGANISM: Homo sapiens

<400> SEQUENCE: 3

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60

Leu Asp Asp Leu Lys Ser Glu Leu Thr Gly Lys Phe Glu Lys Leu Ile
65                  70                  75                  80

Val Ala Leu Met Lys Pro Ser Arg Leu Tyr Asp Ala Tyr Glu Leu Lys
                85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Cys Gly Glu Asp Asp
305                 310                 315

<210> SEQ ID NO 4
<211> LENGTH: 2022
<212> TYPE: DNA
<213> ORGANISM: Artificial sequence
<220> FEATURE:
<223> OTHER INFORMATION: modified annexin gene
<220> FEATURE:
```

```
<221> NAME/KEY: misc_feature
<222> LOCATION: (45)..(45)
<223> OTHER INFORMATION: n= a, c, t, or g
<220> FEATURE:
<221> NAME/KEY: misc_feature
<222> LOCATION: (1003)..(1005)
<223> OTHER INFORMATION: n= a, c, t, or g
<220> FEATURE:
<221> NAME/KEY: misc_feature
<222> LOCATION: (1054)..(1056)
<223> OTHER INFORMATION: n= a, c, t, or g

<400> SEQUENCE: 4
atggactaca aagacgatga cgacaagctt gcggccgcga attcngcaca ggttctcaga     60
ggcactgtga ctgacttccc tggatttgat gagcgggctg atgcagaaac tcttcggaag    120
gctatgaaag gcttgggcac agatgaggag agcatcctga ctctgttgac atcccgaagt    180
aatgctcagc gccaggaaat ctctgcagct tttaagactc tgtttggcag ggatcttctg    240
gatgacctga atcagaact  aactggaaaa tttgaaaaat taattgtggc tctgatgaaa    300
ccctctcggc tttatgatgc ttatgaactg aaacatgcct tgaagggagc tggaacaaat    360
gaaaaagtac tgacagaaat tattgcttca aggacacctg aagaactgag agccatcaaa    420
caagtttatg aagaagaata tggctcaagc ctggaagatg acgtggtggg ggacacttca    480
gggtactacc agcggatgtt ggtggttctc cttcaggcta acagagaccc tgatgctgga    540
attgatgaag ctcaagttga acaagatgct caggctttat ttcaggctgg agaacttaaa    600
tgggggacag atgaagaaaa gtttatcacc atctttggaa cacgaagtgt gtctcatttg    660
agaaaggtgt ttgacaagta catgactata tcaggatttc aaattgagga aaccattgac    720
cgcgagactt ctggcaattt agagcaacta ctccttgctg ttgtgaaatc tattcgaagt    780
atacctgcct accttgcaga gaccctctat tatgctatga agggagctgg gacagatgat    840
catacccctca tcagagtcat ggtttccagg agtgagattg atctgtttaa catcaggaag    900
gagtttagga agaattttgc cacctctctt tattccatga ttaagggaga tacatctggg    960
gactataaga agctcttct  gctgctctgt ggagaagatg acnnnagatc tcgatcgggc   1020
ctggaggtgc tgttccaggg ccccggaagt actnnngcac aggttctcag aggcactgtg   1080
actgacttcc ctggatttga tgagcgggct gatgcagaaa ctcttcggaa ggctatgaaa   1140
ggcttgggca cagatgagga gagcatcctg actctgttga catcccgaag taatgctcag   1200
cgccaggaaa tctctgcagc ttttaagact ctgtttggca gggatcttct ggatgacctg   1260
aaatcagaac taactggaaa atttgaaaaa ttaattgtgg ctctgatgaa accctctcgg   1320
ctttatgatg cttatgaact gaaacatgcc ttgaagggag ctggaacaaa tgaaaaagta   1380
ctgacagaaa ttattgcttc aaggacacct gaagaactga gagccatcaa acaagtttat   1440
gaagaagaat atggctcaag cctggaagat gacgtggtgg gggacacttc agggtactac   1500
cagcggatgt tggtggttct ccttcaggct aacagagacc ctgatgctgg aattgatgaa   1560
gctcaagttg aacaagatgc tcaggcttta tttcaggctg agaacttaa  atgggggaca   1620
gatgaagaaa agtttatcac catctttgga acacgaagtg tgtctcattt gagaaaggtg   1680
tttgacaagt acatgactat atcaggattt caaattgagg aaaccattga ccgcgagact   1740
tctggcaatt tagagcaact actccttgct gttgtgaaat ctattcgaag tatacctgcc   1800
taccttgcag agaccctcta ttatgctatg aagggagctg gacagatga  tcatacccctc   1860
atcagagtca tggtttccag gagtgagatt gatctgttta acatcaggaa ggagtttagg   1920
aagaattttg ccacctctct ttattccatg attaagggag atacatctgg ggactataag   1980
```

```
aaagctcttc tgctgctctg tggagaagat gactaataat aa                         2022
```

<210> SEQ ID NO 5
<211> LENGTH: 2022
<212> TYPE: DNA
<213> ORGANISM: Artificial sequence
<220> FEATURE:
<223> OTHER INFORMATION: modified annexin gene
<220> FEATURE:
<221> NAME/KEY: CDS
<222> LOCATION: (1)..(2022)
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (1003)..(1005)
<223> OTHER INFORMATION: n is a, c, g, or t
<220> FEATURE:
<221> NAME/KEY: misc_feature
<222> LOCATION: (1054)..(1056)
<223> OTHER INFORMATION: n is a, c, g, or t

<400> SEQUENCE: 5

| | | | | | | | | | | | | | | | |
|---|---|---|---|---|---|---|---|---|---|---|---|---|---|---|---|
| atg | gac | tac | aaa | gac | gat | gac | gac | aag | ctt | gcg | gcc | gcg | aat | tcn | gca | 48 |
| Met | Asp | Tyr | Lys | Asp | Asp | Asp | Asp | Lys | Leu | Ala | Ala | Ala | Asn | Xaa | Ala | |
| 1 | | | 5 | | | | | 10 | | | | | 15 | | | |

| cag | gtt | ctc | aga | ggc | act | gtg | act | gac | ttc | cct | gga | ttt | gat | gag | cgg | 96 |
| Gln | Val | Leu | Arg | Gly | Thr | Val | Thr | Asp | Phe | Pro | Gly | Phe | Asp | Glu | Arg | |
| | | | 20 | | | | 25 | | | | | 30 | | | | |

| gct | gat | gca | gaa | act | ctt | cgg | aag | gct | atg | aaa | ggc | ttg | ggc | aca | gat | 144 |
| Ala | Asp | Ala | Glu | Thr | Leu | Arg | Lys | Ala | Met | Lys | Gly | Leu | Gly | Thr | Asp | |
| | | 35 | | | | | 40 | | | | | 45 | | | | |

| gag | gag | agc | atc | ctg | act | ctg | ttg | aca | tcc | cga | agt | aat | gct | cag | cgc | 192 |
| Glu | Glu | Ser | Ile | Leu | Thr | Leu | Leu | Thr | Ser | Arg | Ser | Asn | Ala | Gln | Arg | |
| | 50 | | | | | 55 | | | | | 60 | | | | | |

| cag | gaa | atc | tct | gca | gct | ttt | aag | act | ctg | ttt | ggc | agg | gat | ctt | ctg | 240 |
| Gln | Glu | Ile | Ser | Ala | Ala | Phe | Lys | Thr | Leu | Phe | Gly | Arg | Asp | Leu | Leu | |
| 65 | | | | | 70 | | | | | 75 | | | | | 80 | |

| gat | gac | ctg | aaa | tca | gaa | cta | act | gga | aaa | ttt | gaa | aaa | tta | att | gtg | 288 |
| Asp | Asp | Leu | Lys | Ser | Glu | Leu | Thr | Gly | Lys | Phe | Glu | Lys | Leu | Ile | Val | |
| | | | | 85 | | | | | 90 | | | | | 95 | | |

| gct | ctg | atg | aaa | ccc | tct | cgg | ctt | tat | gat | gct | tat | gaa | ctg | aaa | cat | 336 |
| Ala | Leu | Met | Lys | Pro | Ser | Arg | Leu | Tyr | Asp | Ala | Tyr | Glu | Leu | Lys | His | |
| | | | 100 | | | | | 105 | | | | | 110 | | | |

| gcc | ttg | aag | gga | gct | gga | aca | aat | gaa | aaa | gta | ctg | aca | gaa | att | att | 384 |
| Ala | Leu | Lys | Gly | Ala | Gly | Thr | Asn | Glu | Lys | Val | Leu | Thr | Glu | Ile | Ile | |
| | | 115 | | | | | 120 | | | | | 125 | | | | |

| gct | tca | agg | aca | cct | gaa | gaa | ctg | aga | gcc | atc | aaa | caa | gtt | tat | gaa | 432 |
| Ala | Ser | Arg | Thr | Pro | Glu | Glu | Leu | Arg | Ala | Ile | Lys | Gln | Val | Tyr | Glu | |
| | 130 | | | | | 135 | | | | | 140 | | | | | |

| gaa | gaa | tat | ggc | tca | agc | ctg | gaa | gat | gac | gtg | gtg | ggg | gac | act | tca | 480 |
| Glu | Glu | Tyr | Gly | Ser | Ser | Leu | Glu | Asp | Asp | Val | Val | Gly | Asp | Thr | Ser | |
| 145 | | | | | 150 | | | | | 155 | | | | | 160 | |

| ggg | tac | tac | cag | cgg | atg | ttg | gtg | gtt | ctc | ctt | cag | gct | aac | aga | gac | 528 |
| Gly | Tyr | Tyr | Gln | Arg | Met | Leu | Val | Val | Leu | Leu | Gln | Ala | Asn | Arg | Asp | |
| | | | | 165 | | | | | 170 | | | | | 175 | | |

| cct | gat | gct | gga | att | gat | gaa | gct | caa | gtt | gaa | caa | gat | gct | cag | gct | 576 |
| Pro | Asp | Ala | Gly | Ile | Asp | Glu | Ala | Gln | Val | Glu | Gln | Asp | Ala | Gln | Ala | |
| | | | 180 | | | | | 185 | | | | | 190 | | | |

| tta | ttt | cag | gct | gga | gaa | ctt | aaa | tgg | ggg | aca | gat | gaa | gaa | aag | ttt | 624 |
| Leu | Phe | Gln | Ala | Gly | Glu | Leu | Lys | Trp | Gly | Thr | Asp | Glu | Glu | Lys | Phe | |
| | | 195 | | | | | 200 | | | | | 205 | | | | |

-continued

```
atc acc atc ttt gga aca cga agt gtg tct cat ttg aga aag gtg ttt        672
Ile Thr Ile Phe Gly Thr Arg Ser Val Ser His Leu Arg Lys Val Phe
210             215                 220 gac aag tac atg act ata tca gga ttt caa att gag gaa acc att gac        720
Asp Lys Tyr Met Thr Ile Ser Gly Phe Gln Ile Glu Glu Thr Ile Asp
225             230                 235                 240 cgc gag act tct ggc aat tta gag caa cta ctc ctt gct gtt gtg aaa        768
Arg Glu Thr Ser Gly Asn Leu Glu Gln Leu Leu Leu Ala Val Val Lys
                245                 250                 255 tct att cga agt ata cct gcc tac ctt gca gag acc ctc tat tat gct        816
Ser Ile Arg Ser Ile Pro Ala Tyr Leu Ala Glu Thr Leu Tyr Tyr Ala
            260                 265                 270 atg aag gga gct ggg aca gat gat cat acc ctc atc aga gtc atg gtt        864
Met Lys Gly Ala Gly Thr Asp Asp His Thr Leu Ile Arg Val Met Val
        275                 280                 285 tcc agg agt gag att gat ctg ttt aac atc agg aag gag ttt agg aag        912
Ser Arg Ser Glu Ile Asp Leu Phe Asn Ile Arg Lys Glu Phe Arg Lys
    290                 295                 300 aat ttt gcc acc tct ctt tat tcc atg att aag gga gat aca tct ggg        960
Asn Phe Ala Thr Ser Leu Tyr Ser Met Ile Lys Gly Asp Thr Ser Gly
305                 310                 315                 320 gac tat aag aaa gct ctt ctg ctc tgt gga gaa gat gac nnn aga           1008
Asp Tyr Lys Lys Ala Leu Leu Leu Cys Gly Glu Asp Asp Xaa Arg
                325                 330                 335 tct cga tcg ggc ctg gag gtg ctg ttc cag ggc ccc gga agt act nnn       1056
Ser Arg Ser Gly Leu Glu Val Leu Phe Gln Gly Pro Gly Ser Thr Xaa
            340                 345                 350 gca cag gtt ctc aga ggc act gtg act gac ttc cct gga ttt gat gag      1104
Ala Gln Val Leu Arg Gly Thr Val Thr Asp Phe Pro Gly Phe Asp Glu
        355                 360                 365 cgg gct gat gca gaa act ctt cgg aag gct atg aaa ggc ttg ggc aca      1152
Arg Ala Asp Ala Glu Thr Leu Arg Lys Ala Met Lys Gly Leu Gly Thr
    370                 375                 380 gat gag gag agc atc ctg act ctg ttg aca tcc cga agt aat gct cag      1200
Asp Glu Glu Ser Ile Leu Thr Leu Leu Thr Ser Arg Ser Asn Ala Gln
385                 390                 395                 400 cgc cag gaa atc tct gca gct ttt aag act ctg ttt ggc agg gat ctt      1248
Arg Gln Glu Ile Ser Ala Ala Phe Lys Thr Leu Phe Gly Arg Asp Leu
                405                 410                 415 ctg gat gac ctg aaa tca gaa cta act gga aaa ttt gaa aaa tta att      1296
Leu Asp Asp Leu Lys Ser Glu Leu Thr Gly Lys Phe Glu Lys Leu Ile
            420                 425                 430 gtg gct ctg atg aaa ccc tct cgg ctt tat gat gct tat gaa ctg aaa      1344
Val Ala Leu Met Lys Pro Ser Arg Leu Tyr Asp Ala Tyr Glu Leu Lys
        435                 440                 445 cat gcc ttg aag gga gct gga aca aat gaa aaa gta ctg aca gaa att      1392
His Ala Leu Lys Gly Ala Gly Thr Asn Glu Lys Val Leu Thr Glu Ile
    450                 455                 460 att gct tca agg aca cct gaa gaa ctg aga gcc atc aaa caa gtt tat      1440
Ile Ala Ser Arg Thr Pro Glu Glu Leu Arg Ala Ile Lys Gln Val Tyr
465                 470                 475                 480 gaa gaa gaa tat ggc tca agc ctg gaa gat gac gtg gtg ggg gac act      1488
Glu Glu Glu Tyr Gly Ser Ser Leu Glu Asp Asp Val Val Gly Asp Thr
                485                 490                 495 tca ggg tac tac cag cgg atg ttg gtg gtt ctc ctt cag gct aac aga      1536
Ser Gly Tyr Tyr Gln Arg Met Leu Val Val Leu Leu Gln Ala Asn Arg
            500                 505                 510 gac cct gat gct gga att gat gaa gct caa gtt gaa caa gat gct cag      1584
Asp Pro Asp Ala Gly Ile Asp Glu Ala Gln Val Glu Gln Asp Ala Gln
```

```
                515                 520                 525
gct tta ttt cag gct gga gaa ctt aaa tgg ggg aca gat gaa gaa aag   1632
Ala Leu Phe Gln Ala Gly Glu Leu Lys Trp Gly Thr Asp Glu Glu Lys
    530                 535                 540 ttt atc acc atc ttt gga aca cga agt gtg tct cat ttg aga aag gtg   1680
Phe Ile Thr Ile Phe Gly Thr Arg Ser Val Ser His Leu Arg Lys Val
545                 550                 555                 560 ttt gac aag tac atg act ata tca gga ttt caa att gag gaa acc att   1728
Phe Asp Lys Tyr Met Thr Ile Ser Gly Phe Gln Ile Glu Glu Thr Ile
                565                 570                 575 gac cgc gag act tct ggc aat tta gag caa cta ctc ctt gct gtt gtg   1776
Asp Arg Glu Thr Ser Gly Asn Leu Glu Gln Leu Leu Leu Ala Val Val
            580                 585                 590 aaa tct att cga agt ata cct gcc tac ctt gca gag acc ctc tat tat   1824
Lys Ser Ile Arg Ser Ile Pro Ala Tyr Leu Ala Glu Thr Leu Tyr Tyr
        595                 600                 605 gct atg aag gga gct ggg aca gat gat cat acc ctc atc aga gtc atg   1872
Ala Met Lys Gly Ala Gly Thr Asp Asp His Thr Leu Ile Arg Val Met
    610                 615                 620 gtt tcc agg agt gag att gat ctg ttt aac atc agg aag gag ttt agg   1920
Val Ser Arg Ser Glu Ile Asp Leu Phe Asn Ile Arg Lys Glu Phe Arg
625                 630                 635                 640 aag aat ttt gcc acc tct ctt tat tcc atg att aag gga gat aca tct   1968
Lys Asn Phe Ala Thr Ser Leu Tyr Ser Met Ile Lys Gly Asp Thr Ser
                645                 650                 655 ggg gac tat aag aaa gct ctt ctg ctg ctc tgt gga gaa gat gac taa   2016
Gly Asp Tyr Lys Lys Ala Leu Leu Leu Leu Cys Gly Glu Asp Asp
            660                 665                 670 taa taa                                                           2022
```

<210> SEQ ID NO 6
<211> LENGTH: 671
<212> TYPE: PRT
<213> ORGANISM: Artificial sequence
<220> FEATURE:
<221> NAME/KEY: misc_feature
<222> LOCATION: (15)..(15)
<223> OTHER INFORMATION: The 'Xaa' at location 15 stands for Ser.
<220> FEATURE:
<221> NAME/KEY: misc_feature
<222> LOCATION: (335)..(335)
<223> OTHER INFORMATION: The 'Xaa' at location 335 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (352)..(352)
<223> OTHER INFORMATION: The 'Xaa' at location 352 stands for Lys, Asn,
      Arg, Ser, Thr, Ile, Met, Glu, Asp, Gly, Ala, Val, Gln, His, Pro,
      Leu, Tyr, Trp, Cys, or Phe.
<220> FEATURE:
<223> OTHER INFORMATION: Synthetic Construct

<400> SEQUENCE: 6

```
Met Asp Tyr Lys Asp Asp Asp Lys Leu Ala Ala Ala Asn Xaa Ala
1               5                   10                  15

Gln Val Leu Arg Gly Thr Val Thr Asp Phe Pro Gly Phe Asp Glu Arg
            20                  25                  30

Ala Asp Ala Glu Thr Leu Arg Lys Ala Met Lys Gly Leu Gly Thr Asp
        35                  40                  45

Glu Glu Ser Ile Leu Thr Leu Leu Thr Ser Arg Ser Asn Ala Gln Arg
    50                  55                  60

Gln Glu Ile Ser Ala Ala Phe Lys Thr Leu Phe Gly Arg Asp Leu Leu
```

-continued

```
            65                  70                  75                  80
Asp Asp Leu Lys Ser Glu Leu Thr Gly Lys Phe Glu Lys Leu Ile Val
                    85                  90                  95
Ala Leu Met Lys Pro Ser Arg Leu Tyr Asp Ala Tyr Glu Leu Lys His
                    100                 105                 110
Ala Leu Lys Gly Ala Gly Thr Asn Glu Lys Val Leu Thr Glu Ile Ile
                    115                 120                 125
Ala Ser Arg Thr Pro Glu Glu Leu Arg Ala Ile Lys Gln Val Tyr Glu
            130                 135                 140
Glu Glu Tyr Gly Ser Ser Leu Glu Asp Val Val Gly Asp Thr Ser
145                 150                 155                 160
Gly Tyr Tyr Gln Arg Met Leu Val Val Leu Gln Ala Asn Arg Asp
                    165                 170                 175
Pro Asp Ala Gly Ile Asp Glu Ala Gln Val Glu Gln Asp Ala Gln Ala
                    180                 185                 190
Leu Phe Gln Ala Gly Glu Leu Lys Trp Gly Thr Asp Glu Glu Lys Phe
                    195                 200                 205
Ile Thr Ile Phe Gly Thr Arg Ser Val Ser His Leu Arg Lys Val Phe
            210                 215                 220
Asp Lys Tyr Met Thr Ile Ser Gly Phe Gln Ile Glu Glu Thr Ile Asp
225                 230                 235                 240
Arg Glu Thr Ser Gly Asn Leu Glu Gln Leu Leu Leu Ala Val Val Lys
                    245                 250                 255
Ser Ile Arg Ser Ile Pro Ala Tyr Leu Ala Glu Thr Leu Tyr Tyr Ala
                    260                 265                 270
Met Lys Gly Ala Gly Thr Asp Asp His Thr Leu Ile Arg Val Met Val
                    275                 280                 285
Ser Arg Ser Glu Ile Asp Leu Phe Asn Ile Arg Lys Glu Phe Arg Lys
            290                 295                 300
Asn Phe Ala Thr Ser Leu Tyr Ser Met Ile Lys Gly Asp Thr Ser Gly
305                 310                 315                 320
Asp Tyr Lys Lys Ala Leu Leu Leu Leu Cys Gly Glu Asp Asp Xaa Arg
                    325                 330                 335
Ser Arg Ser Gly Leu Glu Val Leu Phe Gln Gly Pro Gly Ser Thr Xaa
                    340                 345                 350
Ala Gln Val Leu Arg Gly Thr Val Thr Asp Phe Pro Gly Phe Asp Glu
            355                 360                 365
Arg Ala Asp Ala Glu Thr Leu Arg Lys Ala Met Lys Gly Leu Gly Thr
            370                 375                 380
Asp Glu Glu Ser Ile Leu Thr Leu Leu Thr Ser Arg Ser Asn Ala Gln
385                 390                 395                 400
Arg Gln Glu Ile Ser Ala Ala Phe Lys Thr Leu Phe Gly Arg Asp Leu
                    405                 410                 415
Leu Asp Asp Leu Lys Ser Glu Leu Thr Gly Lys Phe Glu Lys Leu Ile
                    420                 425                 430
Val Ala Leu Met Lys Pro Ser Arg Leu Tyr Asp Ala Tyr Glu Leu Lys
                    435                 440                 445
His Ala Leu Lys Gly Ala Gly Thr Asn Glu Lys Val Leu Thr Glu Ile
            450                 455                 460
Ile Ala Ser Arg Thr Pro Glu Glu Leu Arg Ala Ile Lys Gln Val Tyr
465                 470                 475                 480
Glu Glu Glu Tyr Gly Ser Ser Leu Glu Asp Asp Val Val Gly Asp Thr
                    485                 490                 495
```

```
Ser Gly Tyr Tyr Gln Arg Met Leu Val Val Leu Leu Gln Ala Asn Arg
            500                 505                 510

Asp Pro Asp Ala Gly Ile Asp Glu Ala Gln Val Glu Gln Asp Ala Gln
        515                 520                 525

Ala Leu Phe Gln Ala Gly Glu Leu Lys Trp Gly Thr Asp Glu Glu Lys
    530                 535                 540

Phe Ile Thr Ile Phe Gly Thr Arg Ser Val Ser His Leu Arg Lys Val
545                 550                 555                 560

Phe Asp Lys Tyr Met Thr Ile Ser Gly Phe Gln Ile Glu Glu Thr Ile
                565                 570                 575

Asp Arg Glu Thr Ser Gly Asn Leu Glu Gln Leu Leu Leu Ala Val Val
            580                 585                 590

Lys Ser Ile Arg Ser Ile Pro Ala Tyr Leu Ala Glu Thr Leu Tyr Tyr
        595                 600                 605

Ala Met Lys Gly Ala Gly Thr Asp Asp His Thr Leu Ile Arg Val Met
    610                 615                 620

Val Ser Arg Ser Glu Ile Asp Leu Phe Asn Ile Arg Lys Glu Phe Arg
625                 630                 635                 640

Lys Asn Phe Ala Thr Ser Leu Tyr Ser Met Ile Lys Gly Asp Thr Ser
                645                 650                 655

Gly Asp Tyr Lys Lys Ala Leu Leu Leu Leu Cys Gly Glu Asp Asp
            660                 665                 670

<210> SEQ ID NO 7
<211> LENGTH: 30
<212> TYPE: DNA
<213> ORGANISM: Artificial sequence
<220> FEATURE:
<223> OTHER INFORMATION: primer
<220> FEATURE:
<221> NAME/KEY: misc_feature
<222> LOCATION: (1)..(30)
<223> OTHER INFORMATION: primer

<400> SEQUENCE: 7
acctgagtag tcgccatggc acaggttctc                                      30

<210> SEQ ID NO 8
<211> LENGTH: 36
<212> TYPE: DNA
<213> ORGANISM: Artificial sequence
<220> FEATURE:
<223> OTHER INFORMATION: primer

<400> SEQUENCE: 8
cccgaattca cgttagtcat cttctccaca gagcag                               36

<210> SEQ ID NO 9
<211> LENGTH: 8
<212> TYPE: PRT
<213> ORGANISM: Artificial sequence
<220> FEATURE:
<223> OTHER INFORMATION: purification tag

<400> SEQUENCE: 9

Asp Tyr Leu Asp Asp Asp Asp Leu
  1               5

<210> SEQ ID NO 10
<211> LENGTH: 966
<212> TYPE: DNA
```

<213> ORGANISM: Homo sapiens

<400> SEQUENCE: 10

```
atggccatgg caaccaaagg aggtactgtc aaagctgctt caggattcaa tgccatggaa    60
gatgcccaga ccctgaggaa ggccatgaaa gggctcggca ccgatgaaga cgccattatt   120
agcgtccttg cctaccgcaa caccgcccag cgccaggaga tcaggacagc ctacaagagc   180
accatcggca gggacttgat agacgacctg aagtcagaac tgagtggcaa cttcgagcag   240
gtgattgtgg ggatgatgac gcccacggtg ctgtatgacg tgcaagagct gcgaagggcc   300
atgaagggag ccggcactga tgagggctgc ctaattgaga tcctggcctc ccggacccct   360
gaggagatcc ggcgcataag ccaaacctac cagcagcaat atggacggag ccttgaagat   420
gacattcgct ctgacacatc gttcatgttc agcgagtgc tggtgtctct gtcagctggt   480
gggagggatg aaggaaatta tctggacgat gctctcgtga cagggatgc ccaggacctg   540
tatgaggctg agagaagaa atgggggaca atgaggtga aatttctaac tgttctctgt   600
tcccggaacc gaaatcacct gttgcatgtg tttgatgaat acaaaaggat atcacagaag   660
gatattgaac agagtattaa atctgaaaca tctggtagct ttgaagatgc tctgctggct   720
atagtaaagt gcatgaggaa caaatctgca tattttgctg aaaagctcta taatcgatg   780
aagggcttgg gcaccgatga taacacccte atcagagtga tggtttctcg agcagaaatt   840
gacatgttgg atatccgggc acacttcaag agactctatg aaagtctct gtactcgttc   900
atcaagggtg acacatctgg agactacagg aaagtactgc ttgttctctg tggaggagat   960
gattaa                                                               966
```

<210> SEQ ID NO 11
<211> LENGTH: 966
<212> TYPE: DNA
<213> ORGANISM: Homo sapiens
<220> FEATURE:
<221> NAME/KEY: CDS
<222> LOCATION: (1)..(966)

<400> SEQUENCE: 11

```
atg gcc atg gca acc aaa gga ggt act gtc aaa gct gct tca gga ttc     48
Met Ala Met Ala Thr Lys Gly Gly Thr Val Lys Ala Ala Ser Gly Phe
1               5                   10                  15 aat gcc atg gaa gat gcc cag acc ctg agg aag gcc atg aaa ggg ctc     96
Asn Ala Met Glu Asp Ala Gln Thr Leu Arg Lys Ala Met Lys Gly Leu
            20                  25                  30 ggc acc gat gaa gac gcc att att agc gtc ctt gcc tac cgc aac acc    144
Gly Thr Asp Glu Asp Ala Ile Ile Ser Val Leu Ala Tyr Arg Asn Thr
        35                  40                  45 gcc cag cgc cag gag atc agg aca gcc tac aag agc acc atc ggc agg    192
Ala Gln Arg Gln Glu Ile Arg Thr Ala Tyr Lys Ser Thr Ile Gly Arg
    50                  55                  60 gac ttg ata gac gac ctg aag tca gaa ctg agt ggc aac ttc gag cag    240
Asp Leu Ile Asp Asp Leu Lys Ser Glu Leu Ser Gly Asn Phe Glu Gln
65                  70                  75                  80 gtg att gtg ggg atg atg acg ccc acg gtg ctg tat gac gtg caa gag    288
Val Ile Val Gly Met Met Thr Pro Thr Val Leu Tyr Asp Val Gln Glu
                85                  90                  95 ctg cga agg gcc atg aag gga gcc ggc act gat gag ggc tgc cta att    336
Leu Arg Arg Ala Met Lys Gly Ala Gly Thr Asp Glu Gly Cys Leu Ile
            100                 105                 110 gag atc ctg gcc tcc cgg acc cct gag gag atc cgg cgc ata agc caa    384
Glu Ile Leu Ala Ser Arg Thr Pro Glu Glu Ile Arg Arg Ile Ser Gln
```

```
            115                 120                 125
acc tac cag cag caa tat gga cgg agc ctt gaa gat gac att cgc tct      432
Thr Tyr Gln Gln Gln Tyr Gly Arg Ser Leu Glu Asp Asp Ile Arg Ser
    130                 135                 140 gac aca tcg ttc atg ttc cag cga gtg ctg gtg tct ctg tca gct ggt      480
Asp Thr Ser Phe Met Phe Gln Arg Val Leu Val Ser Leu Ser Ala Gly
145                 150                 155                 160 ggg agg gat gaa gga aat tat ctg gac gat gct ctc gtg aga cag gat      528
Gly Arg Asp Glu Gly Asn Tyr Leu Asp Asp Ala Leu Val Arg Gln Asp
                165                 170                 175 gcc cag gac ctg tat gag gct gga gag aag aaa tgg ggg aca gat gag      576
Ala Gln Asp Leu Tyr Glu Ala Gly Glu Lys Lys Trp Gly Thr Asp Glu
            180                 185                 190 gtg aaa ttt cta act gtt ctc tgt tcc cgg aac cga aat cac ctg ttg      624
Val Lys Phe Leu Thr Val Leu Cys Ser Arg Asn Arg Asn His Leu Leu
        195                 200                 205 cat gtg ttt gat gaa tac aaa agg ata tca cag aag gat att gaa cag      672
His Val Phe Asp Glu Tyr Lys Arg Ile Ser Gln Lys Asp Ile Glu Gln
    210                 215                 220 agt att aaa tct gaa aca tct ggt agc ttt gaa gat gct ctg ctg gct      720
Ser Ile Lys Ser Glu Thr Ser Gly Ser Phe Glu Asp Ala Leu Leu Ala
225                 230                 235                 240 ata gta aag tgc atg agg aac aaa tct gca tat ttt gct gaa aag ctc      768
Ile Val Lys Cys Met Arg Asn Lys Ser Ala Tyr Phe Ala Glu Lys Leu
                245                 250                 255 tat aaa tcg atg aag ggc ttg ggc acc gat gat aac acc ctc atc aga      816
Tyr Lys Ser Met Lys Gly Leu Gly Thr Asp Asp Asn Thr Leu Ile Arg
            260                 265                 270 gtg atg gtt tct cga gca gaa att gac atg ttg gat atc cgg gca cac      864
Val Met Val Ser Arg Ala Glu Ile Asp Met Leu Asp Ile Arg Ala His
        275                 280                 285 ttc aag aga ctc tat gga aag tct ctg tac tcg ttc atc aag ggt gac      912
Phe Lys Arg Leu Tyr Gly Lys Ser Leu Tyr Ser Phe Ile Lys Gly Asp
    290                 295                 300 aca tct gga gac tac agg aaa gta ctg ctt gtt ctc tgt gga gga gat      960
Thr Ser Gly Asp Tyr Arg Lys Val Leu Leu Val Leu Cys Gly Gly Asp
305                 310                 315                 320 gat taa                                                              966
Asp

<210> SEQ ID NO 12
<211> LENGTH: 321
<212> TYPE: PRT
<213> ORGANISM: Homo sapiens

<400> SEQUENCE: 12

Met Ala Met Ala Thr Lys Gly Gly Thr Val Lys Ala Ala Ser Gly Phe
1               5                   10                  15

Asn Ala Met Glu Asp Ala Gln Thr Leu Arg Lys Ala Met Lys Gly Leu
            20                  25                  30

Gly Thr Asp Glu Asp Ala Ile Ile Ser Val Leu Ala Tyr Arg Asn Thr
        35                  40                  45

Ala Gln Arg Gln Glu Ile Arg Thr Ala Tyr Lys Ser Thr Ile Gly Arg
    50                  55                  60

Asp Leu Ile Asp Asp Leu Lys Ser Glu Leu Ser Gly Asn Phe Glu Gln
65                  70                  75                  80

Val Ile Val Gly Met Met Thr Pro Thr Val Leu Tyr Asp Val Gln Glu
                85                  90                  95
```

```
Leu Arg Arg Ala Met Lys Gly Ala Gly Thr Asp Glu Gly Cys Leu Ile
            100                 105                 110

Glu Ile Leu Ala Ser Arg Thr Pro Glu Glu Ile Arg Arg Ile Ser Gln
        115                 120                 125

Thr Tyr Gln Gln Gln Tyr Gly Arg Ser Leu Glu Asp Asp Ile Arg Ser
    130                 135                 140

Asp Thr Ser Phe Met Phe Gln Arg Val Leu Val Ser Leu Ser Ala Gly
145                 150                 155                 160

8Gly Arg Asp Glu Gly Asn Tyr Leu Asp Asp Ala Leu Val Arg Gln Asp
                165                 170                 175

Ala Gln Asp Leu Tyr Glu Ala Gly Glu Lys Lys Trp Gly Thr Asp Glu
            180                 185                 190

Val Lys Phe Leu Thr Val Leu Cys Ser Arg Asn Arg Asn His Leu Leu
        195                 200                 205

His Val Phe Asp Glu Tyr Lys Arg Ile Ser Gln Lys Asp Ile Glu Gln
    210                 215                 220

Ser Ile Lys Ser Glu Thr Ser Gly Ser Phe Glu Asp Ala Leu Leu Ala
225                 230                 235                 240

Ile Val Lys Cys Met Arg Asn Lys Ser Ala Tyr Phe Ala Glu Lys Leu
                245                 250                 255

Tyr Lys Ser Met Lys Gly Leu Gly Thr Asp Asp Asn Thr Leu Ile Arg
            260                 265                 270

Val Met Val Ser Arg Ala Glu Ile Asp Met Leu Asp Ile Arg Ala His
        275                 280                 285

Phe Lys Arg Leu Tyr Gly Lys Ser Leu Tyr Ser Phe Ile Lys Gly Asp
    290                 295                 300

Thr Ser Gly Asp Tyr Arg Lys Val Leu Leu Val Leu Cys Gly Gly Asp
305                 310                 315                 320

Asp

<210> SEQ ID NO 13
<211> LENGTH: 984
<212> TYPE: DNA
<213> ORGANISM: Homo sapiens

<400> SEQUENCE: 13
atggcctggt ggaaagcctg gattgaacag gagggtgtca cagtgaagag cagctcccac      60
ttcaacccag accctgatgc agagaccctc tacaaagcca tgaagggat cgggaccaac     120 gagcaggcta tcatcgatgt gctcaccaag agaagcaaca cgcagcggca gcagatcgcc     180
aagtccttca ggctcagtt cggcaaggac ctcactgaga ccttgaagtc tgagctcagt     240
ggcaagtttg agaggctcat tgtggccctt atgtatccgc atacagata cgaagccaag     300 gagctgcatg acgccatgaa gggcttagga accaaggagg tgtcatcat tgagatcctg     360 gcctctcgga ccaagaacca gctgcgggag ataatgaagg cgtatgagga agactatggg     420
tccagcctgg aggaggacat ccaagcagac acaagtggct acctggagag gatcctggtg     480
tgcctcctgc agggcagcag ggatgatgtg agcagctttg tggacccggc actggccctc     540
caagacgcac aggatctgta tcggcaggc gagaagattc gtgggactga tgagatgaaa     600
ttcatcacca tcctgtgcac gcgcagtgcc actcacctgc tgagagtgtt tgaagagtat     660
gagaaaattg ccaacaagag cattgaggac agcatcaaga gtgagaccca tggctcactg     720
gaggaggcca tgctcactgt ggtgaaatgc acccaaaacc tccacagcta ctttgcagag     780
agactctact atgccatgaa gggagcaggg acgcgtgatg ggaccctgat aagaaacatc     840
```

-continued

```
gtttcaagga gcgagattga cttaaatctt atcaaatgtc acttcaagaa gatgtacggc      900
aagaccctca gcagcatgat catggaagac accagcggcg actacaagaa cgccctgctg      960
agcctggtgg gcagcgaccc ctga                                              984
```

<210> SEQ ID NO 14
<211> LENGTH: 984
<212> TYPE: DNA
<213> ORGANISM: Homo sapiens
<220> FEATURE:
<221> NAME/KEY: CDS
<222> LOCATION: (1)..(984)

<400> SEQUENCE: 14

```
atg gcc tgg tgg aaa gcc tgg att gaa cag gag ggt gtc aca gtg aag       48
Met Ala Trp Trp Lys Ala Trp Ile Glu Gln Glu Gly Val Thr Val Lys
1               5                   10                  15 agc agc tcc cac ttc aac cca gac cct gat gca gag acc ctc tac aaa       96
Ser Ser Ser His Phe Asn Pro Asp Pro Asp Ala Glu Thr Leu Tyr Lys
            20                  25                  30 gcc atg aag ggg atc ggg acc aac gag cag gct atc atc gat gtg ctc      144
Ala Met Lys Gly Ile Gly Thr Asn Glu Gln Ala Ile Ile Asp Val Leu
        35                  40                  45 acc aag aga agc aac acg cag cgg cag cag atc gcc aag tcc ttc aag      192
Thr Lys Arg Ser Asn Thr Gln Arg Gln Gln Ile Ala Lys Ser Phe Lys
    50                  55                  60 gct cag ttc ggc aag gac ctc act gag acc ttg aag tct gag ctc agt      240
Ala Gln Phe Gly Lys Asp Leu Thr Glu Thr Leu Lys Ser Glu Leu Ser
65                  70                  75                  80 ggc aag ttt gag agg ctc att gtg gcc ctt atg tat ccg cca tac aga      288
Gly Lys Phe Glu Arg Leu Ile Val Ala Leu Met Tyr Pro Pro Tyr Arg
                85                  90                  95 tac gaa gcc aag gag ctg cat gac gcc atg aag ggc tta gga acc aag      336
Tyr Glu Ala Lys Glu Leu His Asp Ala Met Lys Gly Leu Gly Thr Lys
            100                 105                 110 gag ggt gtc atc att gag atc ctg gcc tct cgg acc aag aac cag ctg      384
Glu Gly Val Ile Ile Glu Ile Leu Ala Ser Arg Thr Lys Asn Gln Leu
        115                 120                 125 cgg gag ata atg aag gcg tat gag gaa gac tat ggg tcc agc ctg gag      432
Arg Glu Ile Met Lys Ala Tyr Glu Glu Asp Tyr Gly Ser Ser Leu Glu
    130                 135                 140 gag gac atc caa gca gac aca agt ggc tac ctg gag agg atc ctg gtg      480
Glu Asp Ile Gln Ala Asp Thr Ser Gly Tyr Leu Glu Arg Ile Leu Val
145                 150                 155                 160 tgc ctc ctg cag ggc agc agg gat gat gtg agc agc ttt gtg gac ccg      528
Cys Leu Leu Gln Gly Ser Arg Asp Asp Val Ser Ser Phe Val Asp Pro
                165                 170                 175 gca ctg gcc ctc caa gac gca cag gat ctg tat gcg gca ggc gag aag      576
Ala Leu Ala Leu Gln Asp Ala Gln Asp Leu Tyr Ala Ala Gly Glu Lys
            180                 185                 190 att cgt ggg act gat gag atg aaa ttc atc acc atc ctg tgc acg cgc      624
Ile Arg Gly Thr Asp Glu Met Lys Phe Ile Thr Ile Leu Cys Thr Arg
        195                 200                 205 agt gcc act cac ctg ctg aga gtg ttt gaa gag tat gag aaa att gcc      672
Ser Ala Thr His Leu Leu Arg Val Phe Glu Glu Tyr Glu Lys Ile Ala
    210                 215                 220 aac aag agc att gag gac agc atc aag agt gag acc cat ggc tca ctg      720
Asn Lys Ser Ile Glu Asp Ser Ile Lys Ser Glu Thr His Gly Ser Leu
225                 230                 235                 240 gag gag gcc atg ctc act gtg gtg aaa tgc acc caa aac ctc cac agc      768
```

```
Glu Glu Ala Met Leu Thr Val Val Lys Cys Thr Gln Asn Leu His Ser
            245                 250                 255 tac ttt gca gag aga ctc tac tat gcc atg aag gga gca ggg acg cgt        816
Tyr Phe Ala Glu Arg Leu Tyr Tyr Ala Met Lys Gly Ala Gly Thr Arg
        260                 265                 270 gat ggg acc ctg ata aga aac atc gtt tca agg agc gag att gac tta        864
Asp Gly Thr Leu Ile Arg Asn Ile Val Ser Arg Ser Glu Ile Asp Leu
            275                 280                 285 aat ctt atc aaa tgt cac ttc aag aag atg tac ggc aag acc ctc agc        912
Asn Leu Ile Lys Cys His Phe Lys Lys Met Tyr Gly Lys Thr Leu Ser
        290                 295                 300 agc atg atc atg gaa gac acc agc ggc gac tac aag aac gcc ctg ctg        960
Ser Met Ile Met Glu Asp Thr Ser Gly Asp Tyr Lys Asn Ala Leu Leu
305                 310                 315                 320 agc ctg gtg ggc agc gac ccc tga                                         984
Ser Leu Val Gly Ser Asp Pro
                325

<210> SEQ ID NO 15
<211> LENGTH: 327
<212> TYPE: PRT
<213> ORGANISM: Homo sapiens

<400> SEQUENCE: 15

Met Ala Trp Trp Lys Ala Trp Ile Glu Gln Glu Gly Val Thr Val Lys
1               5                   10                  15

Ser Ser Ser His Phe Asn Pro Asp Pro Asp Ala Glu Thr Leu Tyr Lys
            20                  25                  30

Ala Met Lys Gly Ile Gly Thr Asn Glu Gln Ala Ile Ile Asp Val Leu
        35                  40                  45

Thr Lys Arg Ser Asn Thr Gln Arg Gln Gln Ile Ala Lys Ser Phe Lys
    50                  55                  60

Ala Gln Phe Gly Lys Asp Leu Thr Glu Thr Leu Lys Ser Glu Leu Ser
65                  70                  75                  80

Gly Lys Phe Glu Arg Leu Ile Val Ala Leu Met Tyr Pro Pro Tyr Arg
                85                  90                  95

Tyr Glu Ala Lys Glu Leu His Asp Ala Met Lys Gly Leu Gly Thr Lys
            100                 105                 110

Glu Gly Val Ile Ile Glu Ile Leu Ala Ser Arg Thr Lys Asn Gln Leu
        115                 120                 125

Arg Glu Ile Met Lys Ala Tyr Glu Glu Asp Tyr Gly Ser Ser Leu Glu
    130                 135                 140

Glu Asp Ile Gln Ala Asp Thr Ser Gly Tyr Leu Glu Arg Ile Leu Val
145                 150                 155                 160

Cys Leu Leu Gln Gly Ser Arg Asp Asp Val Ser Ser Phe Val Asp Pro
                165                 170                 175

Ala Leu Ala Leu Gln Asp Ala Gln Asp Leu Tyr Ala Ala Gly Glu Lys
            180                 185                 190

Ile Arg Gly Thr Asp Glu Met Lys Phe Ile Thr Ile Leu Cys Thr Arg
        195                 200                 205

Ser Ala Thr His Leu Leu Arg Val Phe Glu Glu Tyr Glu Lys Ile Ala
    210                 215                 220

Asn Lys Ser Ile Glu Asp Ser Ile Lys Ser Glu Thr His Gly Ser Leu
225                 230                 235                 240

Glu Glu Ala Met Leu Thr Val Val Lys Cys Thr Gln Asn Leu His Ser
                245                 250                 255
```

```
Tyr Phe Ala Glu Arg Leu Tyr Tyr Ala Met Lys Gly Ala Gly Thr Arg
                260                 265                 270

Asp Gly Thr Leu Ile Arg Asn Ile Val Ser Arg Ser Glu Ile Asp Leu
            275                 280                 285

Asn Leu Ile Lys Cys His Phe Lys Lys Met Tyr Gly Lys Thr Leu Ser
        290                 295                 300

Ser Met Ile Met Glu Asp Thr Ser Gly Asp Tyr Lys Asn Ala Leu Leu
305                 310                 315                 320

Ser Leu Val Gly Ser Asp Pro
                325

<210> SEQ ID NO 16
<211> LENGTH: 7221
<212> TYPE: DNA
<213> ORGANISM: Artificial sequence
<220> FEATURE:
<223> OTHER INFORMATION: plasmid

<400> SEQUENCE: 16
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aacccatatct cggtctattc     360 ttttgattta agggatttt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga tcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
cccttgtatt actgtttatg taagcagaca gttttattgt tcatgaccaa atcccttaa     1440 cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttttc cgaaggtaac tggcttcagc    1620
```

```
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980
ccaggggaaa acgcctggta tctttatagt cctgtcgggt ttcgccacct ctgacttgag    2040
cgtcgatttt tgtgatgctc gtcagggggg cggagcctat ggaaaaacgc cagcaacgcg    2100 gccttttac ggttcctggc cttttgctgg cctttgctc acatgttctt cctgcgtta     2160 tccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280 tatttctcc ttacgcatct gtgcggtatt tcacaccgca tatatggtgc actctcagta   2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatccgga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagacttta    3000
cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
atcccactac cgagatgtcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccagacgc agacgcgccg    4020
```

```
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa agacaccgg    4560 catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg cgatataggg cgccagcaac cgcacctgtg   4920
gcgccggtga tgccggccac gatgcgtccg gcgtagagga tcgagatcga tctcgatccc   4980
gcgaaattaa tacgactcac tataggggaa ttgtgagcgg ataacaattc ccctctagaa   5040
ataattttgt ttaactttaa gaaggagata tacatatggc catggcaacc aaaggaggta   5100
ctgtcaaagc tgcttcagga ttcaatgcca tggaagatgc ccagaccctg aggaaggcca   5160
tgaaagggct cggcaccgat gaagacgcca ttattagcgt ccttgcctac cgcaacaccg   5220
cccagcgcca ggagatcagg acagcctaca agagcaccat cggcagggac ttgatagacg   5280
acctgaagtc agaactgagt ggcaacttcg agcaggtgat tgtggggatg atgacgccca   5340
cggtgctgta tgacgtgcaa gagctgcgaa gggccatgaa gggagccggc actgatgagg   5400
gctgcctaat tgagatcctg gcctcccgga cccctgagga gatccggcgc ataagccaaa   5460
cctaccagca gcaatatgga cggaggcttg aagatgacat tcgctctgac acatcgttca   5520
tgttccagcg agtgctggtg tctctgtcag ctggtgggag ggatgaagga aattatctgg   5580
acgatgctct cgtgagacag gatgcccagg acctgtatga ggctggagag aagaaatggg   5640
ggacagatga ggtgaaattt ctaactgttc tctgttcccg gaaccgaaat cacctgttgc   5700
atgtgtttga tgaatacaaa aggatatcac agaaggatat tgaacagagt attaaatctg   5760
aaacatctgg tagctttgaa gatgctctgc tggctatagt aaagtgcatg aggaacaaat   5820
ctgcatattt tgctgaaaag ctctataaat cgatgaaggg cttgggcacc gatgataaca   5880
ccctcatcag agtgatggtt tctcgagcag aaattgacat gttggatatc cgggcacact   5940
tcaagagact ctatggaaag tctctgtact cgttcatcaa gggtgacaca tctggagact   6000
acaggaaagt actgcttgtt ctctgtggag gagatgatgg atccctggag gtgctgttcc   6060
agggcccctc cgggaagctt gccatggcaa ccaaggagg tactgtcaaa gctgcttcag    6120
gattcaatgc catggaagat gcccagaccc tgaggaaggc catgaaaggg ctcggcaccg   6180
atgaagacgc cattattagc gtccttgcct accgcaacac cgcccagcgc caggagatca   6240
ggacagccta caagagcacc atcggcaggg acttgataga cgacctgaag tcagaactga   6300
gtggcaactt cgagcaggtg attgtgggga tgatgacgcc cacggtgctg tatgacgtgc   6360
```

```
aagagctgcg aagggccatg aagggagccg gcactgatga gggctgccta attgagatcc    6420
tggcctcccg gacccctgag gagatccggc gcataagcca aacctaccag cagcaatatg    6480
gacggaggct tgaagatgac attcgctctg acacatcgtt catgttccag cgagtgctgg    6540
tgtctctgtc agctggtggg agggatgaag gaaattatct ggacgatgct ctcgtgagac    6600
aggatgccca ggacctgtat gaggctgag agaagaaatg ggggacagat gaggtgaaat    6660
ttctaactgt tctctgttcc cggaaccgaa atcacctgtt gcatgtgttt gatgaataca    6720
aaaggatatc acagaaggat attgaacaga gtattaaatc tgaaacatct ggtagctttg    6780
aagatgctct gctggctata gtaaagtgca tgaggaacaa atctgcatat tttgctgaaa    6840
agctctataa atcgatgaag ggcttgggca ccgatgataa caccctcatc agagtgatgg    6900
tttctcgagc agaaattgac atgttggata tccgggcaca cttcaagaga ctctatggaa    6960
agtctctgta ctcgttcatc aagggtgaca catctggaga ctacaggaaa gtactgcttg    7020
ttctctgtgg aggagatgat taatagtaag cggccgcact cgagcaccac caccaccacc    7080
actgagatcc ggctgctaac aaagcccgaa aggaagctga gttggctgct gccaccgctg    7140
agcaataact agcataaccc cttggggcct ctaaacgggt cttgaggggt tttttgctga    7200
aaggaggaac tatatccgga t                                              7221

<210> SEQ ID NO 17
<211> LENGTH: 1974
<212> TYPE: DNA
<213> ORGANISM: Artificial sequence
<220> FEATURE:
<223> OTHER INFORMATION: plasmid

<400> SEQUENCE: 17
atggccatgg caaccaaagg aggtactgtc aaagctgctt caggattcaa tgccatggaa      60
gatgcccaga ccctgaggaa ggccatgaaa gggctcggca ccgatgaaga cgccattatt     120
agcgtccttg cctaccgcaa caccgcccag cgccaggaga tcaggacagc ctacaagagc     180
accatcggca gggacttgat agacgacctg aagtcagaac tgagtggcaa cttcgagcag     240
gtgattgtgg ggatgatgac gcccacggtg ctgtatgacg tgcaagagct gcgaagggcc     300
atgaagggag ccggcactga tgagggctgc ctaattgaga tcctggcctc ccggacccct     360
gaggagatcc ggcgcataag ccaaacctac cagcagcaat atggacggag gcttgaagat     420
gacattcgct ctgacacatc gttcatgttc agcgagtgc tggtgtctct gtcagctggt     480
gggagggatg aaggaaatta tctggacgat gctctcgtga gacaggatgc ccaggacctg     540
tatgaggctg agagaagaa atgggggaca gatgaggtga atttctaac tgttctctgt     600 tcccggaacc gaaatcacct gttgcatgtg tttgatgaat acaaaaggat atcacagaag     660
gatattgaac agagtattaa atctgaaaca tctggtagct ttgaagatgc tctgctggct     720
atagtaaagt gcatgaggaa caaatctgca tattttgctg aaaagctcta taatcgatg     780 aagggcttgg gcaccgatga taacaccctc atcagagtga tggtttctcg agcagaaatt     840
gacatgttgg atatccgggc acacttcaag agactctatg gaaagtctct gtactcgttc     900
atcaagggtg acacatctgg agactacagg aaagtactgc ttgttctctg tggaggagat     960 gatgatccc tggaggtgct gttccaggc ccctccggga agcttgccat ggcaaccaaa      1020
ggaggtactg tcaaagctgc ttcaggattc aatgccatgg aagatgccca gaccctgagg     1080
aaggccatga aagggctcgg caccgatgaa gacgccatta ttagcgtcct tgcctaccgc     1140
aacaccgccc agcgccagga gatcaggaca gcctacaaga gcaccatcgg cagggacttg     1200
```

```
atagacgacc tgaagtcaga actgagtggc aacttcgagc aggtgattgt ggggatgatg    1260
acgcccacgg tgctgtatga cgtgcaagag ctgcgaaggg ccatgaaggg agccggcact    1320
gatgagggct gcctaattga gatcctggcc tcccggaccc ctgaggagat ccggcgcata    1380
agccaaacct accagcagca atatggacgg aggcttgaag atgacattcg ctctgacaca    1440
tcgttcatgt tccagcgagt gctggtgtct ctgtcagctg gtggagggga tgaaggaaat    1500
tatctggacg atgctctcgt gagacaggat gcccaggacc tgtatgaggc tggagagaag    1560
aaatggggga cagatgaggt gaaatttcta actgttctct gttcccggaa ccgaaatcac    1620
ctgttgcatg tgtttgatga atacaaaagg atatcacaga aggatattga acagagtatt    1680
aaatctgaaa catctggtag ctttgaagat gctctgctgg ctatagtaaa gtgcatgagg    1740
aacaaatctg catattttgc tgaaaagctc tataaatcga tgaagggctt gggcaccgat    1800
gataacaccc tcatcagagt gatggttttct cgagcagaaa ttgacatgtt ggatatccgg    1860
gcacacttca agagactcta tggaaagtct ctgtactcgt tcatcaaggg tgacacatct    1920
ggagactaca ggaaagtact gcttgttctc tgtggaggag atgattaata gtaa          1974

<210> SEQ ID NO 18
<211> LENGTH: 1974
<212> TYPE: DNA
<213> ORGANISM: Artificial sequence
<220> FEATURE:
<223> OTHER INFORMATION: plasmid
<220> FEATURE:
<221> NAME/KEY: CDS
<222> LOCATION: (1)..(1974)

<400> SEQUENCE: 18 atg gcc atg gca acc aaa gga ggt act gtc aaa gct gct tca gga ttc     48
Met Ala Met Ala Thr Lys Gly Gly Thr Val Lys Ala Ala Ser Gly Phe
1               5                  10                  15 aat gcc atg gaa gat gcc cag acc ctg agg aag gcc atg aaa ggg ctc     96
Asn Ala Met Glu Asp Ala Gln Thr Leu Arg Lys Ala Met Lys Gly Leu
            20                  25                  30 ggc acc gat gaa gac gcc att att agc gtc ctt gcc tac cgc aac acc    144
Gly Thr Asp Glu Asp Ala Ile Ile Ser Val Leu Ala Tyr Arg Asn Thr
        35                  40                  45 gcc cag cgc cag gag atc agg aca gcc tac aag agc acc atc ggc agg    192
Ala Gln Arg Gln Glu Ile Arg Thr Ala Tyr Lys Ser Thr Ile Gly Arg
    50                  55                  60 gac ttg ata gac gac ctg aag tca gaa ctg agt ggc aac ttc gag cag    240
Asp Leu Ile Asp Asp Leu Lys Ser Glu Leu Ser Gly Asn Phe Glu Gln
65                  70                  75                  80 gtg att gtg ggg atg atg acg ccc acg gtg ctg tat gac gtg caa gag    288
Val Ile Val Gly Met Met Thr Pro Thr Val Leu Tyr Asp Val Gln Glu
                85                  90                  95 ctg cga agg gcc atg aag gga gcc ggc act gat gag ggc tgc cta att    336
Leu Arg Arg Ala Met Lys Gly Ala Gly Thr Asp Glu Gly Cys Leu Ile
            100                 105                 110 gag atc ctg gcc tcc cgg acc cct gag gag atc cgg cgc ata agc caa    384
Glu Ile Leu Ala Ser Arg Thr Pro Glu Glu Ile Arg Arg Ile Ser Gln
        115                 120                 125 acc tac cag cag caa tat gga cgg agg ctt gaa gat gac att cgc tct    432
Thr Tyr Gln Gln Gln Tyr Gly Arg Arg Leu Glu Asp Asp Ile Arg Ser
    130                 135                 140 gac aca tcg ttc atg ttc cag cga gtg ctg gtg tct ctg tca gct ggt    480
Asp Thr Ser Phe Met Phe Gln Arg Val Leu Val Ser Leu Ser Ala Gly
145                 150                 155                 160
```

-continued

| | |
|---|---|
| ggg agg gat gaa gga aat tat ctg gac gat gct ctc gtg aga cag gat<br>Gly Arg Asp Glu Gly Asn Tyr Leu Asp Asp Ala Leu Val Arg Gln Asp<br>165                     170                     175 | 528 |
| gcc cag gac ctg tat gag gct gga gag aag aaa tgg ggg aca gat gag<br>Ala Gln Asp Leu Tyr Glu Ala Gly Glu Lys Lys Trp Gly Thr Asp Glu<br>180                     185                     190 | 576 |
| gtg aaa ttt cta act gtt ctc tgt tcc cgg aac cga aat cac ctg ttg<br>Val Lys Phe Leu Thr Val Leu Cys Ser Arg Asn Arg Asn His Leu Leu<br>195                     200                     205 | 624 |
| cat gtg ttt gat gaa tac aaa agg ata tca cag aag gat att gaa cag<br>His Val Phe Asp Glu Tyr Lys Arg Ile Ser Gln Lys Asp Ile Glu Gln<br>210                     215                     220 | 672 |
| agt att aaa tct gaa aca tct ggt agc ttt gaa gat gct ctg ctg gct<br>Ser Ile Lys Ser Glu Thr Ser Gly Ser Phe Glu Asp Ala Leu Leu Ala<br>225                     230                     235                     240 | 720 |
| ata gta aag tgc atg agg aac aaa tct gca tat ttt gct gaa aag ctc<br>Ile Val Lys Cys Met Arg Asn Lys Ser Ala Tyr Phe Ala Glu Lys Leu<br>                     245                     250                     255 | 768 |
| tat aaa tcg atg aag ggc ttg ggc acc gat gat aac acc ctc atc aga<br>Tyr Lys Ser Met Lys Gly Leu Gly Thr Asp Asp Asn Thr Leu Ile Arg<br>           260                     265                     270 | 816 |
| gtg atg gtt tct cga gca gaa att gac atg ttg gat atc cgg gca cac<br>Val Met Val Ser Arg Ala Glu Ile Asp Met Leu Asp Ile Arg Ala His<br>275                     280                     285 | 864 |
| ttc aag aga ctc tat gga aag tct ctg tac tcg ttc atc aag ggt gac<br>Phe Lys Arg Leu Tyr Gly Lys Ser Leu Tyr Ser Phe Ile Lys Gly Asp<br>           290                     295                     300 | 912 |
| aca tct gga gac tac agg aaa gta ctg ctt gtt ctc tgt gga gga gat<br>Thr Ser Gly Asp Tyr Arg Lys Val Leu Leu Val Leu Cys Gly Gly Asp<br>305                     310                     315                     320 | 960 |
| gat gga tcc ctg gag gtg ctg ttc cag ggc ccc tcc ggg aag ctt gcc<br>Asp Gly Ser Leu Glu Val Leu Phe Gln Gly Pro Ser Gly Lys Leu Ala<br>                     325                     330                     335 | 1008 |
| atg gca acc aaa gga ggt act gtc aaa gct gct tca gga ttc aat gcc<br>Met Ala Thr Lys Gly Gly Thr Val Lys Ala Ala Ser Gly Phe Asn Ala<br>           340                     345                     350 | 1056 |
| atg gaa gat gcc cag acc ctg agg aag gcc atg aaa ggg ctc ggc acc<br>Met Glu Asp Ala Gln Thr Leu Arg Lys Ala Met Lys Gly Leu Gly Thr<br>           355                     360                     365 | 1104 |
| gat gaa gac gcc att att agc gtc ctt gcc tac cgc aac acc gcc cag<br>Asp Glu Asp Ala Ile Ile Ser Val Leu Ala Tyr Arg Asn Thr Ala Gln<br>370                     375                     380 | 1152 |
| cgc cag gag atc agg aca gcc tac aag agc acc atc ggc agg gac ttg<br>Arg Gln Glu Ile Arg Thr Ala Tyr Lys Ser Thr Ile Gly Arg Asp Leu<br>385                     390                     395                     400 | 1200 |
| ata gac gac ctg aag tca gaa ctg agt ggc aac ttc gag cag gtg att<br>Ile Asp Asp Leu Lys Ser Glu Leu Ser Gly Asn Phe Glu Gln Val Ile<br>                     405                     410                     415 | 1248 |
| gtg ggg atg atg acg ccc acg gtg ctg tat gac gtg caa gag ctg cga<br>Val Gly Met Met Thr Pro Thr Val Leu Tyr Asp Val Gln Glu Leu Arg<br>           420                     425                     430 | 1296 |
| agg gcc atg aag gga gcc ggc act gat gag ggc tgc cta att gag atc<br>Arg Ala Met Lys Gly Ala Gly Thr Asp Glu Gly Cys Leu Ile Glu Ile<br>           435                     440                     445 | 1344 |
| ctg gcc tcc cgg acc cct gag gag atc cgg cgc ata agc caa acc tac<br>Leu Ala Ser Arg Thr Pro Glu Glu Ile Arg Arg Ile Ser Gln Thr Tyr<br>450                     455                     460 | 1392 |
| cag cag caa tat gga cgg agg ctt gaa gat gac att cgc tct gac aca<br>Gln Gln Gln Tyr Gly Arg Arg Leu Glu Asp Asp Ile Arg Ser Asp Thr | 1440 |

```
                465                 470                 475                 480
tcg ttc atg ttc cag cga gtg ctg gtg tct ctg tca gct ggt ggg agg         1488
Ser Phe Met Phe Gln Arg Val Leu Val Ser Leu Ser Ala Gly Gly Arg
                    485                 490                 495 gat gaa gga aat tat ctg gac gat gct ctc gtg aga cag gat gcc cag         1536
Asp Glu Gly Asn Tyr Leu Asp Asp Ala Leu Val Arg Gln Asp Ala Gln
                500                 505                 510 gac ctg tat gag gct gga gag aag aaa tgg ggg aca gat gag gtg aaa         1584
Asp Leu Tyr Glu Ala Gly Glu Lys Lys Trp Gly Thr Asp Glu Val Lys
            515                 520                 525 ttt cta act gtt ctc tgt tcc cgg aac cga aat cac ctg ttg cat gtg         1632
Phe Leu Thr Val Leu Cys Ser Arg Asn Arg Asn His Leu Leu His Val
        530                 535                 540 ttt gat gaa tac aaa agg ata tca cag aag gat att gaa cag agt att         1680
Phe Asp Glu Tyr Lys Arg Ile Ser Gln Lys Asp Ile Glu Gln Ser Ile
545                 550                 555                 560 aaa tct gaa aca tct ggt agc ttt gaa gat gct ctg ctg gct ata gta         1728
Lys Ser Glu Thr Ser Gly Ser Phe Glu Asp Ala Leu Leu Ala Ile Val
                565                 570                 575 aag tgc atg agg aac aaa tct gca tat ttt gct gaa aag ctc tat aaa         1776
Lys Cys Met Arg Asn Lys Ser Ala Tyr Phe Ala Glu Lys Leu Tyr Lys
                580                 585                 590 tcg atg aag ggc ttg ggc acc gat gat aac acc ctc atc aga gtg atg         1824
Ser Met Lys Gly Leu Gly Thr Asp Asp Asn Thr Leu Ile Arg Val Met
            595                 600                 605 gtt tct cga gca gaa att gac atg ttg gat atc cgg gca cac ttc aag         1872
Val Ser Arg Ala Glu Ile Asp Met Leu Asp Ile Arg Ala His Phe Lys
        610                 615                 620 aga ctc tat gga aag tct ctg tac tcg ttc atc aag ggt gac aca tct         1920
Arg Leu Tyr Gly Lys Ser Leu Tyr Ser Phe Ile Lys Gly Asp Thr Ser
625                 630                 635                 640 gga gac tac agg aaa gta ctg ctt gtt ctc tgt gga gga gat gat taa         1968
Gly Asp Tyr Arg Lys Val Leu Leu Val Leu Cys Gly Gly Asp Asp
                645                 650                 655 tag taa                                                                 1974

<210> SEQ ID NO 19
<211> LENGTH: 655
<212> TYPE: PRT
<213> ORGANISM: Artificial sequence
<220> FEATURE:
<223> OTHER INFORMATION: Synthetic Construct

<400> SEQUENCE: 19

Met Ala Met Ala Thr Lys Gly Gly Thr Val Lys Ala Ala Ser Gly Phe
1               5                   10                  15

Asn Ala Met Glu Asp Ala Gln Thr Leu Arg Lys Ala Met Lys Gly Leu
                20                  25                  30

Gly Thr Asp Glu Asp Ala Ile Ile Ser Val Leu Ala Tyr Arg Asn Thr
            35                  40                  45

Ala Gln Arg Gln Glu Ile Arg Thr Ala Tyr Lys Ser Thr Ile Gly Arg
        50                  55                  60

Asp Leu Ile Asp Asp Leu Lys Ser Glu Leu Ser Gly Asn Phe Glu Gln
65                  70                  75                  80

Val Ile Val Gly Met Met Thr Pro Thr Val Leu Tyr Asp Val Gln Glu
                85                  90                  95

Leu Arg Arg Ala Met Lys Gly Ala Gly Thr Asp Glu Gly Cys Leu Ile
            100                 105                 110
```

-continued

```
Glu Ile Leu Ala Ser Arg Thr Pro Glu Glu Ile Arg Arg Ile Ser Gln
            115                 120                 125
Thr Tyr Gln Gln Gln Tyr Gly Arg Arg Leu Glu Asp Asp Ile Arg Ser
        130                 135                 140
Asp Thr Ser Phe Met Phe Gln Arg Val Leu Val Ser Leu Ser Ala Gly
145                 150                 155                 160
Gly Arg Asp Glu Gly Asn Tyr Leu Asp Asp Ala Leu Val Arg Gln Asp
                165                 170                 175
Ala Gln Asp Leu Tyr Glu Ala Gly Glu Lys Lys Trp Gly Thr Asp Glu
            180                 185                 190
Val Lys Phe Leu Thr Val Leu Cys Ser Arg Asn Arg Asn His Leu Leu
        195                 200                 205
His Val Phe Asp Glu Tyr Lys Arg Ile Ser Gln Lys Asp Ile Glu Gln
210                 215                 220
Ser Ile Lys Ser Glu Thr Ser Gly Ser Phe Glu Asp Ala Leu Leu Ala
225                 230                 235                 240
Ile Val Lys Cys Met Arg Asn Lys Ser Ala Tyr Phe Ala Glu Lys Leu
                245                 250                 255
Tyr Lys Ser Met Lys Gly Leu Gly Thr Asp Asp Asn Thr Leu Ile Arg
            260                 265                 270
Val Met Val Ser Arg Ala Glu Ile Asp Met Leu Asp Ile Arg Ala His
        275                 280                 285
Phe Lys Arg Leu Tyr Gly Lys Ser Leu Tyr Ser Phe Ile Lys Gly Asp
290                 295                 300
Thr Ser Gly Asp Tyr Arg Lys Val Leu Leu Val Leu Cys Gly Gly Asp
305                 310                 315                 320
Asp Gly Ser Leu Glu Val Leu Phe Gln Gly Pro Ser Gly Lys Leu Ala
                325                 330                 335
Met Ala Thr Lys Gly Gly Thr Val Lys Ala Ala Ser Gly Phe Asn Ala
            340                 345                 350
Met Glu Asp Ala Gln Thr Leu Arg Lys Ala Met Lys Gly Leu Gly Thr
        355                 360                 365
Asp Glu Asp Ala Ile Ile Ser Val Leu Ala Tyr Arg Asn Thr Ala Gln
370                 375                 380
Arg Gln Glu Ile Arg Thr Ala Tyr Lys Ser Thr Ile Gly Arg Asp Leu
385                 390                 395                 400
Ile Asp Asp Leu Lys Ser Glu Leu Ser Gly Asn Phe Glu Gln Val Ile
                405                 410                 415
Val Gly Met Met Thr Pro Thr Val Leu Tyr Asp Val Gln Glu Leu Arg
            420                 425                 430
Arg Ala Met Lys Gly Ala Gly Thr Asp Glu Gly Cys Leu Ile Glu Ile
        435                 440                 445
Leu Ala Ser Arg Thr Pro Glu Glu Ile Arg Arg Ile Ser Gln Thr Tyr
450                 455                 460
Gln Gln Gln Tyr Gly Arg Arg Leu Glu Asp Asp Ile Arg Ser Asp Thr
465                 470                 475                 480
Ser Phe Met Phe Gln Arg Val Leu Val Ser Leu Ser Ala Gly Gly Arg
                485                 490                 495
Asp Glu Gly Asn Tyr Leu Asp Asp Ala Leu Val Arg Gln Asp Ala Gln
            500                 505                 510
Asp Leu Tyr Glu Ala Gly Glu Lys Lys Trp Gly Thr Asp Glu Val Lys
        515                 520                 525
Phe Leu Thr Val Leu Cys Ser Arg Asn Arg Asn His Leu Leu His Val
```

```
              530                 535                 540
Phe Asp Glu Tyr Lys Arg Ile Ser Gln Lys Asp Ile Glu Gln Ser Ile
545                 550                 555                 560

Lys Ser Glu Thr Ser Gly Ser Phe Glu Asp Ala Leu Leu Ala Ile Val
                565                 570                 575

Lys Cys Met Arg Asn Lys Ser Ala Tyr Phe Ala Glu Lys Leu Tyr Lys
                580                 585                 590

Ser Met Lys Gly Leu Gly Thr Asp Asp Asn Thr Leu Ile Arg Val Met
                595                 600                 605

Val Ser Arg Ala Glu Ile Asp Met Leu Asp Ile Arg Ala His Phe Lys
610                 615                 620

Arg Leu Tyr Gly Lys Ser Leu Tyr Ser Phe Ile Lys Gly Asp Thr Ser
625                 630                 635                 640

Gly Asp Tyr Arg Lys Val Leu Leu Val Leu Cys Gly Gly Asp Asp
                645                 650                 655

<210> SEQ ID NO 20
<211> LENGTH: 7257
<212> TYPE: DNA
<213> ORGANISM: Artificial sequence
<220> FEATURE:
<223> OTHER INFORMATION: plasmid

<400> SEQUENCE: 20
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta atcggggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta agggatttt gccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttatttttc taaatacatt caaatatgta     540
tccgctcatg aattaattct tagaaaaact catcgagcat caaatgaaac tgcaatttat     600
tcatatcagg attatcaata ccatattttt gaaaaagccg tttctgtaat gaaggagaaa     660
actcaccgag gcagttccat aggatggcaa gatcctggta tcggtctgcg attccgactc     720
gtccaacatc aatacaacct attaatttcc cctcgtcaaa aataaggtta tcaagtgaga     780
aatcaccatg agtgacgact gaatccggtg agaatggcaa aagtttatgc atttctttcc     840
agacttgttc aacaggccag ccattacgct cgtcatcaaa atcactcgca tcaaccaaac     900
cgttattcat tcgtgattgc gcctgagcga cgaaatac gcgatcgctg ttaaaaggac     960
aattacaaac aggaatcgaa tgcaaccggc gcaggaacac tgccagcgca tcaacaatat    1020
tttcacctga tcaggatat tcttctaata cctggaatgc tgttttcccg gggatcgcag    1080
tggtgagtaa ccatgcatca tcaggagtac ggataaaatg cttgatggtc ggaagaggca    1140
taaattccgt cagccagttt agtctgacca tctcatctgt aacatcattg gcaacgctac    1200
ctttgccatg tttcagaaac aactctggcg catcgggctt cccatacaat cgatagattg    1260
tcgcacctga ttgcccgaca ttatcgcgag cccatttata cccatataaa tcagcatcca    1320
tgttggaatt taatcgcggc ctagagcaag acgtttcccg ttgaatatgg ctcataacac    1380
```

```
cccttgtatt actgtttatg taagcagaca gttttattgt tcatgaccaa aatcccttaa    1440
cgtgagtttt cgttccactg agcgtcagac cccgtagaaa agatcaaagg atcttcttga    1500
gatccttttt ttctgcgcgt aatctgctgc ttgcaaacaa aaaaaccacc gctaccagcg    1560
gtggtttgtt tgccggatca agagctacca actcttttc cgaaggtaac tggcttcagc     1620
agagcgcaga taccaaatac tgtccttcta gtgtagccgt agttaggcca ccacttcaag    1680
aactctgtag caccgcctac atacctcgct ctgctaatcc tgttaccagt ggctgctgcc    1740
agtggcgata agtcgtgtct taccgggttg gactcaagac gatagttacc ggataaggcg    1800
cagcggtcgg gctgaacggg gggttcgtgc acacagccca gcttggagcg aacgacctac    1860
accgaactga gatacctaca gcgtgagcta tgagaaagcg ccacgcttcc cgaagggaga    1920
aaggcggaca ggtatccggt aagcggcagg gtcggaacag gagagcgcac gagggagctt    1980 ccaggggaa acgcctggta tctttatagt cctgtcgggt ttcgccacct ctgacttgag     2040
cgtcgatttt tgtgatgctc gtcagggggg cggagcctat ggaaaaacgc cagcaacgcg    2100
gcctttttac ggttcctggc cttttgctgg ccttttgctc acatgttctt tcctgcgtta    2160
tcccctgatt ctgtggataa ccgtattacc gcctttgagt gagctgatac cgctcgccgc    2220
agccgaacga ccgagcgcag cgagtcagtg agcgaggaag cggaagagcg cctgatgcgg    2280
tattttctcc ttacgcatct gtgcggtatt tcacaccgca tatatggtgc actctcagta    2340
caatctgctc tgatgccgca tagttaagcc agtatacact ccgctatcgc tacgtgactg    2400
ggtcatggct gcgccccgac acccgccaac acccgctgac gcgccctgac gggcttgtct    2460
gctcccggca tccgcttaca gacaagctgt gaccgtctcc gggagctgca tgtgtcagag    2520
gttttcaccg tcatcaccga aacgcgcgag gcagctgcgg taaagctcat cagcgtggtc    2580
gtgaagcgat tcacagatgt ctgcctgttc atccgcgtcc agctcgttga gtttctccag    2640
aagcgttaat gtctggcttc tgataaagcg ggccatgtta agggcggttt tttcctgttt    2700
ggtcactgat gcctccgtgt aagggggatt tctgttcatg ggggtaatga taccgatgaa    2760
acgagagagg atgctcacga tacgggttac tgatgatgaa catgcccggt tactggaacg    2820
ttgtgagggt aaacaactgg cggtatggat gcggcgggac cagagaaaaa tcactcaggg    2880
tcaatgccag cgcttcgtta atacagatgt aggtgttcca cagggtagcc agcagcatcc    2940
tgcgatgcag atccggaaca taatggtgca gggcgctgac ttccgcgttt ccagactta     3000 cgaaacacgg aaaccgaaga ccattcatgt tgttgctcag gtcgcagacg ttttgcagca    3060
gcagtcgctt cacgttcgct cgcgtatcgg tgattcattc tgctaaccag taaggcaacc    3120
ccgccagcct agccgggtcc tcaacgacag gagcacgatc atgcgcaccc gtggggccgc    3180
catgccggcg ataatggcct gcttctcgcc gaaacgtttg gtggcgggac cagtgacgaa    3240
ggcttgagcg agggcgtgca agattccgaa taccgcaagc gacaggccga tcatcgtcgc    3300
gctccagcga aagcggtcct cgccgaaaat gacccagagc gctgccggca cctgtcctac    3360
gagttgcatg ataaagaaga cagtcataag tgcggcgacg atagtcatgc cccgcgccca    3420
ccggaaggag ctgactgggt tgaaggctct caagggcatc ggtcgagatc ccggtgccta    3480
atgagtgagc taacttacat taattgcgtt gcgctcactg cccgctttcc agtcgggaaa    3540
cctgtcgtgc cagctgcatt aatgaatcgg ccaacgcgcg gggagaggcg gtttgcgtat    3600
tgggcgccag ggtggttttt cttttcacca gtgagacggg caacagctga ttgcccttca    3660
ccgcctggcc ctgagagagt tgcagcaagc ggtccacgct ggtttgcccc agcaggcgaa    3720
aatcctgttt gatggtggtt aacggcggga tataacatga gctgtcttcg gtatcgtcgt    3780
```

```
atcccactac cgagatgtcc gcaccaacgc gcagcccgga ctcggtaatg gcgcgcattg   3840
cgcccagcgc catctgatcg ttggcaacca gcatcgcagt gggaacgatg ccctcattca   3900
gcatttgcat ggtttgttga aaaccggaca tggcactcca gtcgccttcc cgttccgcta   3960
tcggctgaat ttgattgcga gtgagatatt tatgccagcc agccagacgc agacgcgccg   4020
agacagaact taatgggccc gctaacagcg cgatttgctg gtgacccaat gcgaccagat   4080
gctccacgcc cagtcgcgta ccgtcttcat gggagaaaat aatactgttg atgggtgtct   4140
ggtcagagac atcaagaaat aacgccggaa cattagtgca ggcagcttcc acagcaatgg   4200
catcctggtc atccagcgga tagttaatga tcagcccact gacgcgttgc gcgagaagat   4260
tgtgcaccgc cgctttacag gcttcgacgc cgcttcgttc taccatcgac accaccacgc   4320
tggcacccag ttgatcggcg cgagatttaa tcgccgcgac aatttgcgac ggcgcgtgca   4380
gggccagact ggaggtggca acgccaatca gcaacgactg tttgcccgcc agttgttgtg   4440
ccacgcggtt gggaatgtaa ttcagctccg ccatcgccgc ttccactttt tcccgcgttt   4500
tcgcagaaac gtggctggcc tggttcacca cgcgggaaac ggtctgataa agacaccgg    4560 catactctgc gacatcgtat aacgttactg gtttcacatt caccaccctg aattgactct   4620
cttccgggcg ctatcatgcc ataccgcgaa aggttttgcg ccattcgatg gtgtccggga   4680
tctcgacgct ctcccttatg cgactcctgc attaggaagc agcccagtag taggttgagg   4740
ccgttgagca ccgccgccgc aaggaatggt gcatgcaagg agatggcgcc caacagtccc   4800
ccggccacgg ggcctgccac catacccacg ccgaaacaag cgctcatgag cccgaagtgg   4860
cgagcccgat cttccccatc ggtgatgtcg gcgatatagg cgccagcaac cgcacctgtg   4920
gcgccggtga tgccggccac gatgcgtccg gcgtagagga tcgagatcga tctcgatccc   4980
gcgaaattaa tacgactcac tatagggaaa ttgtgagcgg ataacaattc ccctctagaa   5040
ataattttgt ttaactttaa gaaggagata tacatatggc ctggtggaaa gcctggattg   5100
aacaggaggg tgtcacagtg aagagcagct cccacttcaa cccagaccct gatgcagaga   5160
ccctctacaa agccatgaag gggatcggga ccaacgagca ggctatcatc gatgtgctca   5220
ccaagagaag caacacgcag cggcagcaga tcgccaagtc cttcaaggct cagttcggca   5280
aggacctcac tgagacctig aagtctgagc tcagtggcaa gtttgagagg ctcattgtgg   5340
cccttatgta cccgccatac agatacgaag ccaaggagct gcatgacgcc atgaagggct   5400
taggaaccaa ggagggtgtc atcattgaga tcctggcctc tcggaccaag aaccagctgc   5460
gggagataat gaaggcgtat gaggaagact atgggtccag cctggaggag gacatccaag   5520
cagacacaag tggctacctg gagaggatcc tggtgtgcct cctgcagggc agcagggatg   5580
atgtgagcag ctttgtggac ccggcactgg ccctccaaga cgcacaggat ctgtatgcgg   5640
caggcgagaa gattcgtggg actgatgaga tgaaattcat caccatcctg tgcacgcgca   5700
gtgccactca cctgctgaga gtgtttgaag agtatgagaa aattgccaac aagagcattg   5760
aggacagcat caagagtgag acccatggct cactggagga ggccatgctc actgtggtga   5820
aatgcaccca aaacctccac agctactttg cagagagact ctactatgcc atgaagggag   5880
cagggacgcg tgatgggacc ctgataagaa acatcgtttc aaggagcgag attgacttaa   5940
atcttatcaa atgtcacttc aagaagatgt acggcaagac cctcagcagc atgatcatgg   6000
aagacaccag cggcgactac aagaacgccc tgctgagcct ggtgggcagc gaccccggat   6060
ccctggaggt gctgttccag ggcccctccg ggaagcttgc ctggtggaaa gcctggattg   6120
```

```
aacaggaggg tgtcacagtg aagagcagct cccacttcaa cccagaccct gatgcagaga      6180
ccctctacaa agccatgaag gggatcggga ccaacgagca ggctatcatc gatgtgctca      6240
ccaagagaag caacacgcag cggcagcaga tcgccaagtc cttcaaggct cagttcggca      6300
aggacctcac tgagaccttg aagtctgagc tcagtggcaa gtttgagagg ctcattgtgg      6360
cccttatgta cccgccatac agatacgaag ccaaggagct gcatgacgcc atgaagggct      6420
taggaaccaa ggagggtgtc atcattgaga tcctggcctc tcggaccaag aaccagctgc      6480
gggagataat gaaggcgtat gaggaagact atgggtccag cctggaggag gacatccaag      6540
cagacacaag tggctacctg gagaggatcc tggtgtgcct cctgcagggc agcagggatg      6600
atgtgagcag ctttgtggac ccggcactgg ccctccaaga cgcacaggat ctgtatgcgg      6660
caggcgagaa gattcgtggg actgatgaga tgaaattcat caccatcctg tgcacgcgca      6720
gtgccactca cctgctgaga gtgtttgaag agtatgagaa aattgccaac aagagcattg      6780
aggacagcat caagagtgag acccatggct cactggagga ggccatgctc actgtggtga      6840
aatgcaccca aaacctccac agctactttg cagagagact ctactatgcc atgaagggag      6900
cagggacgcg tgatgggacc ctgataagaa acatcgtttc aaggagcgag attgacttaa      6960
atcttatcaa atgtcacttc aagaagatgt acggcaagac cctcagcagc atgatcatgg      7020
aagacaccag cggcgactac aagaacgccc tgctgagcct ggtgggcagc gaccctgat       7080 aataagcggc cgcactcgag caccaccacc accaccactg agatccggct gctaacaaag      7140
cccgaaagga agctgagttg gctgctgcca ccgctgagca ataactagca taaccccttg      7200
gggcctctaa acgggtcttg aggggttttt tgctgaaagg aggaactata tccggat         7257
```

<210> SEQ ID NO 21
<211> LENGTH: 2004
<212> TYPE: DNA
<213> ORGANISM: Artificial sequence
<220> FEATURE:
<223> OTHER INFORMATION: plasmid

<400> SEQUENCE: 21

```
atggcctggt ggaaagcctg gattgaacag gagggtgtca cagtgaagag cagctcccac        60
ttcaacccag accctgatgc agagaccctc tacaaagcca tgaagggggat cgggaccaac      120 gagcaggcta tcatcgatgt gctcaccaag agaagcaaca cgcagcggca gcagatcgcc      180
aagtccttca ggctcagtt cggcaaggac ctcactgaga ccttgaagtc tgagctcagt       240
ggcaagtttg agaggctcat tgtggccctt atgtacccgc catacagata cgaagccaag       300
gagctgcatg acgccatgaa gggcttagga accaaggagg gtgtcatcat tgagatcctg      360
gcctctcgga ccaagaacca gctgcgggag ataatgaagg cgtatgagga agactatggg       420
tccagcctgg aggaggacat ccaagcagac acaagtggct acctggagag gatcctggtg      480
tgcctcctgc agggcagcag ggatgatgtg agcagctttg tggacccggc actggccctc      540
caagacgcac aggatctgta tgcggcaggc gagaagattc gtgggactga tgagatgaaa      600
ttcatcacca tcctgtgcac gcgcagtgcc actcacctgc tgagagtgtt tgaagagtat      660
gagaaaattg ccaacaagag cattgaggac agcatcaaga gtgagaccca tggctcactg      720
gaggaggcca tgctcactgt ggtgaaatgc acccaaaacc tccacagcta ctttgcagag      780
agactctact atgccatgaa gggagcaggg acgcgtgatg ggaccctgat aagaaacatc      840
gtttcaagga gcgagattga cttaaatctt atcaaatgtc acttcaagaa gatgtacggc      900
aagaccctca gcagcatgat catggaagac accagcggcg actacaagaa cgccctgctg      960
```

-continued

```
agcctggtgg gcagcgaccc cggatccctg gaggtgctgt tccagggccc ctccgggaag    1020
cttgcctggt ggaaagcctg gattgaacag gagggtgtca cagtgaagag cagctcccac    1080
ttcaacccag accctgatgc agagaccctc tacaaagcca tgaagggat cgggaccaac     1140 gagcaggcta tcatcgatgt gctcaccaag agaagcaaca cgcagcggca gcagatcgcc    1200
aagtccttca ggctcagtt cggcaaggac ctcactgaga ccttgaagtc tgagctcagt     1260
ggcaagtttg agaggctcat tgtggccctt atgtacccgc catacagata cgaagccaag    1320
gagctgcatg acgccatgaa gggcttagga accaaggagg tgtcatcat tgagatcctg    1380 gcctctcgga ccaagaacca gctgcgggag ataatgaagg cgtatgagga agactatggg    1440
tccagcctgg aggaggacat ccaagcagac acaagtggct acctggagag gatcctggtg    1500
tgcctcctgc agggcagcag ggatgatgtg agcagctttg tggacccggc actggccctc    1560
caagacgcac aggatctgta tgcggcaggc gagaagattc gtgggactga tgagatgaaa    1620
ttcatcacca tcctgtgcac gcgcagtgcc actcacctgc tgagagtgtt tgaagagtat    1680
gagaaaattg ccaacaagag cattgaggac agcatcaaga gtgagaccca tggctcactg    1740
gaggaggcca tgctcactgt ggtgaaatgc acccaaaacc tccacagcta ctttgcagag    1800
agactctact atgccatgaa gggagcaggg acgcgtgatg ggaccctgat aagaaacatc    1860
gtttcaagga gcgagattga cttaaatctt atcaaatgtc acttcaagaa gatgtacggc    1920
aagaccctca gcagcatgat catggaagac accagcggcg actacaagaa cgccctgctg    1980
agcctggtgg gcagcgaccc ctga                                           2004
```

<210> SEQ ID NO 22
<211> LENGTH: 2004
<212> TYPE: DNA
<213> ORGANISM: Artificial sequence
<220> FEATURE:
<223> OTHER INFORMATION: plasmid
<220> FEATURE:
<221> NAME/KEY: CDS
<222> LOCATION: (1)..(2004)

<400> SEQUENCE: 22

```
atg gcc tgg tgg aaa gcc tgg att gaa cag gag ggt gtc aca gtg aag      48
Met Ala Trp Trp Lys Ala Trp Ile Glu Gln Glu Gly Val Thr Val Lys
1               5                   10                  15 agc agc tcc cac ttc aac cca gac cct gat gca gag acc ctc tac aaa      96
Ser Ser Ser His Phe Asn Pro Asp Pro Asp Ala Glu Thr Leu Tyr Lys
            20                  25                  30 gcc atg aag ggg atc ggg acc aac gag cag gct atc atc gat gtg ctc     144
Ala Met Lys Gly Ile Gly Thr Asn Glu Gln Ala Ile Ile Asp Val Leu
        35                  40                  45 acc aag aga agc aac acg cag cgg cag cag atc gcc aag tcc ttc aag     192
Thr Lys Arg Ser Asn Thr Gln Arg Gln Gln Ile Ala Lys Ser Phe Lys
    50                  55                  60 gct cag ttc ggc aag gac ctc act gag acc ttg aag tct gag ctc agt     240
Ala Gln Phe Gly Lys Asp Leu Thr Glu Thr Leu Lys Ser Glu Leu Ser
65                  70                  75                  80 ggc aag ttt gag agg ctc att gtg gcc ctt atg tac ccg cca tac aga     288
Gly Lys Phe Glu Arg Leu Ile Val Ala Leu Met Tyr Pro Pro Tyr Arg
                85                  90                  95 tac gaa gcc aag gag ctg cat gac gcc atg aag ggc tta gga acc aag     336
Tyr Glu Ala Lys Glu Leu His Asp Ala Met Lys Gly Leu Gly Thr Lys
            100                 105                 110 gag ggt gtc atc att gag atc ctg gcc tct cgg acc aag aac cag ctg     384
```

|     |     |     |     |     |     |     |     |     |     |     |     |     |     |     |     |
|---|---|---|---|---|---|---|---|---|---|---|---|---|---|---|---|
| | | Glu | Gly | Val | Ile | Ile | Glu | Ile | Leu | Ala | Ser | Arg | Thr | Lys | Asn Gln Leu |
| | | | | 115 | | | | 120 | | | | | 125 | | |

| cgg | gag | ata | atg | aag | gcg | tat | gag | gaa | gac | tat | ggg | tcc | agc | ctg | gag | 432 |
|---|---|---|---|---|---|---|---|---|---|---|---|---|---|---|---|---|
| Arg | Glu | Ile | Met | Lys | Ala | Tyr | Glu | Glu | Asp | Tyr | Gly | Ser | Ser | Leu | Glu | |
| | 130 | | | | 135 | | | | 140 | | | | | | | |

| gag | gac | atc | caa | gca | gac | aca | agt | ggc | tac | ctg | gag | agg | atc | ctg | gtg | 480 |
|---|---|---|---|---|---|---|---|---|---|---|---|---|---|---|---|---|
| Glu | Asp | Ile | Gln | Ala | Asp | Thr | Ser | Gly | Tyr | Leu | Glu | Arg | Ile | Leu | Val | |
| 145 | | | | | 150 | | | | | 155 | | | | | 160 | |

| tgc | ctc | ctg | cag | ggc | agc | agg | gat | gat | gtg | agc | agc | ttt | gtg | gac | ccg | 528 |
|---|---|---|---|---|---|---|---|---|---|---|---|---|---|---|---|---|
| Cys | Leu | Leu | Gln | Gly | Ser | Arg | Asp | Asp | Val | Ser | Ser | Phe | Val | Asp | Pro | |
| | | | | 165 | | | | | 170 | | | | | 175 | | |

| gca | ctg | gcc | ctc | caa | gac | gca | cag | gat | ctg | tat | gcg | gca | ggc | gag | aag | 576 |
|---|---|---|---|---|---|---|---|---|---|---|---|---|---|---|---|---|
| Ala | Leu | Ala | Leu | Gln | Asp | Ala | Gln | Asp | Leu | Tyr | Ala | Ala | Gly | Glu | Lys | |
| | | | 180 | | | | | 185 | | | | | 190 | | | |

| att | cgt | ggg | act | gat | gag | atg | aaa | ttc | atc | acc | atc | ctg | tgc | acg | cgc | 624 |
|---|---|---|---|---|---|---|---|---|---|---|---|---|---|---|---|---|
| Ile | Arg | Gly | Thr | Asp | Glu | Met | Lys | Phe | Ile | Thr | Ile | Leu | Cys | Thr | Arg | |
| | | 195 | | | | | 200 | | | | | 205 | | | | |

| agt | gcc | act | cac | ctg | ctg | aga | gtg | ttt | gaa | gag | tat | gag | aaa | att | gcc | 672 |
|---|---|---|---|---|---|---|---|---|---|---|---|---|---|---|---|---|
| Ser | Ala | Thr | His | Leu | Leu | Arg | Val | Phe | Glu | Glu | Tyr | Glu | Lys | Ile | Ala | |
| | 210 | | | | | 215 | | | | | 220 | | | | | |

| aac | aag | agc | att | gag | gac | agc | atc | aag | agt | gag | acc | cat | ggc | tca | ctg | 720 |
|---|---|---|---|---|---|---|---|---|---|---|---|---|---|---|---|---|
| Asn | Lys | Ser | Ile | Glu | Asp | Ser | Ile | Lys | Ser | Glu | Thr | His | Gly | Ser | Leu | |
| 225 | | | | | 230 | | | | | 235 | | | | | 240 | |

| gag | gag | gcc | atg | ctc | act | gtg | gtg | aaa | tgc | acc | caa | aac | ctc | cac | agc | 768 |
|---|---|---|---|---|---|---|---|---|---|---|---|---|---|---|---|---|
| Glu | Glu | Ala | Met | Leu | Thr | Val | Val | Lys | Cys | Thr | Gln | Asn | Leu | His | Ser | |
| | | | | 245 | | | | | 250 | | | | | 255 | | |

| tac | ttt | gca | gag | aga | ctc | tac | tat | gcc | atg | aag | gga | gca | ggg | acg | cgt | 816 |
|---|---|---|---|---|---|---|---|---|---|---|---|---|---|---|---|---|
| Tyr | Phe | Ala | Glu | Arg | Leu | Tyr | Tyr | Ala | Met | Lys | Gly | Ala | Gly | Thr | Arg | |
| | | | | 260 | | | | | 265 | | | | | 270 | | |

| gat | ggg | acc | ctg | ata | aga | aac | atc | gtt | tca | agg | agc | gag | att | gac | tta | 864 |
|---|---|---|---|---|---|---|---|---|---|---|---|---|---|---|---|---|
| Asp | Gly | Thr | Leu | Ile | Arg | Asn | Ile | Val | Ser | Arg | Ser | Glu | Ile | Asp | Leu | |
| | | | 275 | | | | | 280 | | | | | 285 | | | |

| aat | ctt | atc | aaa | tgt | cac | ttc | aag | aag | atg | tac | ggc | aag | acc | ctc | agc | 912 |
|---|---|---|---|---|---|---|---|---|---|---|---|---|---|---|---|---|
| Asn | Leu | Ile | Lys | Cys | His | Phe | Lys | Lys | Met | Tyr | Gly | Lys | Thr | Leu | Ser | |
| | 290 | | | | | 295 | | | | | 300 | | | | | |

| agc | atg | atc | atg | gaa | gac | acc | agc | ggc | gac | tac | aag | aac | gcc | ctg | ctg | 960 |
|---|---|---|---|---|---|---|---|---|---|---|---|---|---|---|---|---|
| Ser | Met | Ile | Met | Glu | Asp | Thr | Ser | Gly | Asp | Tyr | Lys | Asn | Ala | Leu | Leu | |
| 305 | | | | | 310 | | | | | 315 | | | | | 320 | |

| agc | ctg | gtg | ggc | agc | gac | ccc | gga | tcc | ctg | gag | gtg | ctg | ttc | cag | ggc | 1008 |
|---|---|---|---|---|---|---|---|---|---|---|---|---|---|---|---|---|
| Ser | Leu | Val | Gly | Ser | Asp | Pro | Gly | Ser | Leu | Glu | Val | Leu | Phe | Gln | Gly | |
| | | | | 325 | | | | | 330 | | | | | 335 | | |

| ccc | tcc | ggg | aag | ctt | gcc | tgg | tgg | aaa | gcc | tgg | att | gaa | cag | gag | ggt | 1056 |
|---|---|---|---|---|---|---|---|---|---|---|---|---|---|---|---|---|
| Pro | Ser | Gly | Lys | Leu | Ala | Trp | Trp | Lys | Ala | Trp | Ile | Glu | Gln | Glu | Gly | |
| | | | 340 | | | | | 345 | | | | | 350 | | | |

| gtc | aca | gtg | aag | agc | agc | tcc | cac | ttc | aac | cca | gac | cct | gat | gca | gag | 1104 |
|---|---|---|---|---|---|---|---|---|---|---|---|---|---|---|---|---|
| Val | Thr | Val | Lys | Ser | Ser | Ser | His | Phe | Asn | Pro | Asp | Pro | Asp | Ala | Glu | |
| | | 355 | | | | | 360 | | | | | 365 | | | | |

| acc | ctc | tac | aaa | gcc | atg | aag | ggg | atc | ggg | acc | aac | gag | cag | gct | atc | 1152 |
|---|---|---|---|---|---|---|---|---|---|---|---|---|---|---|---|---|
| Thr | Leu | Tyr | Lys | Ala | Met | Lys | Gly | Ile | Gly | Thr | Asn | Glu | Gln | Ala | Ile | |
| | 370 | | | | | 375 | | | | | 380 | | | | | |

| atc | gat | gtg | ctc | acc | aag | aga | agc | aac | acg | cag | cgg | cag | cag | atc | gcc | 1200 |
|---|---|---|---|---|---|---|---|---|---|---|---|---|---|---|---|---|
| Ile | Asp | Val | Leu | Thr | Lys | Arg | Ser | Asn | Thr | Gln | Arg | Gln | Gln | Ile | Ala | |
| 385 | | | | | 390 | | | | | 395 | | | | | 400 | |

| aag | tcc | ttc | aag | gct | cag | ttc | ggc | aag | gac | ctc | act | gag | acc | ttg | aag | 1248 |
|---|---|---|---|---|---|---|---|---|---|---|---|---|---|---|---|---|
| Lys | Ser | Phe | Lys | Ala | Gln | Phe | Gly | Lys | Asp | Leu | Thr | Glu | Thr | Leu | Lys | |
| | | | | 405 | | | | | 410 | | | | | 415 | | |

| tct | gag | ctc | agt | ggc | aag | ttt | gag | agg | ctc | att | gtg | gcc | ctt | atg | tac | 1296 |
|---|---|---|---|---|---|---|---|---|---|---|---|---|---|---|---|---|
| Ser | Glu | Leu | Ser | Gly | Lys | Phe | Glu | Arg | Leu | Ile | Val | Ala | Leu | Met | Tyr | |
| | | | 420 | | | | | 425 | | | | | 430 | | | |

```
ccg cca tac aga tac gaa gcc aag gag ctg cat gac gcc atg aag ggc    1344
Pro Pro Tyr Arg Tyr Glu Ala Lys Glu Leu His Asp Ala Met Lys Gly
        435                 440                 445 tta gga acc aag gag ggt gtc atc att gag atc ctg gcc tct cgg acc    1392
Leu Gly Thr Lys Glu Gly Val Ile Ile Glu Ile Leu Ala Ser Arg Thr
    450                 455                 460 aag aac cag ctg cgg gag ata atg aag gcg tat gag gaa gac tat ggg    1440
Lys Asn Gln Leu Arg Glu Ile Met Lys Ala Tyr Glu Glu Asp Tyr Gly
465                 470                 475                 480 tcc agc ctg gag gag gac atc caa gca gac aca agt ggc tac ctg gag    1488
Ser Ser Leu Glu Glu Asp Ile Gln Ala Asp Thr Ser Gly Tyr Leu Glu
                485                 490                 495 agg atc ctg gtg tgc ctc ctg cag ggc agc agg gat gat gtg agc agc    1536
Arg Ile Leu Val Cys Leu Leu Gln Gly Ser Arg Asp Asp Val Ser Ser
            500                 505                 510 ttt gtg gac ccg gca ctg gcc ctc caa gac gca cag gat ctg tat gcg    1584
Phe Val Asp Pro Ala Leu Ala Leu Gln Asp Ala Gln Asp Leu Tyr Ala
        515                 520                 525 gca ggc gag aag att cgt ggg act gat gag atg aaa ttc atc acc atc    1632
Ala Gly Glu Lys Ile Arg Gly Thr Asp Glu Met Lys Phe Ile Thr Ile
    530                 535                 540 ctg tgc acg cgc agt gcc act cac ctg ctg aga gtg ttt gaa gag tat    1680
Leu Cys Thr Arg Ser Ala Thr His Leu Leu Arg Val Phe Glu Glu Tyr
545                 550                 555                 560 gag aaa att gcc aac aag agc att gag gac agc atc aag agt gag acc    1728
Glu Lys Ile Ala Asn Lys Ser Ile Glu Asp Ser Ile Lys Ser Glu Thr
                565                 570                 575 cat ggc tca ctg gag gag gcc atg ctc act gtg gtg aaa tgc acc caa    1776
His Gly Ser Leu Glu Glu Ala Met Leu Thr Val Val Lys Cys Thr Gln
            580                 585                 590 aac ctc cac agc tac ttt gca gag aga ctc tac tat gcc atg aag gga    1824
Asn Leu His Ser Tyr Phe Ala Glu Arg Leu Tyr Tyr Ala Met Lys Gly
        595                 600                 605 gca ggg acg cgt gat ggg acc ctg ata aga aac atc gtt tca agg agc    1872
Ala Gly Thr Arg Asp Gly Thr Leu Ile Arg Asn Ile Val Ser Arg Ser
    610                 615                 620 gag att gac tta aat ctt atc aaa tgt cac ttc aag aag atg tac ggc    1920
Glu Ile Asp Leu Asn Leu Ile Lys Cys His Phe Lys Lys Met Tyr Gly
625                 630                 635                 640 aag acc ctc agc agc atg atc atg gaa gac acc agc ggc gac tac aag    1968
Lys Thr Leu Ser Ser Met Ile Met Glu Asp Thr Ser Gly Asp Tyr Lys
                645                 650                 655 aac gcc ctg ctg agc ctg gtg ggc agc gac ccc tga                    2004
Asn Ala Leu Leu Ser Leu Val Gly Ser Asp Pro
            660                 665
```

<210> SEQ ID NO 23
<211> LENGTH: 667
<212> TYPE: PRT
<213> ORGANISM: Artificial sequence
<220> FEATURE:
<223> OTHER INFORMATION: Synthetic Construct

<400> SEQUENCE: 23

```
Met Ala Trp Trp Lys Ala Trp Ile Glu Gln Glu Gly Val Thr Val Lys
1               5                   10                  15

Ser Ser Ser His Phe Asn Pro Asp Pro Asp Ala Glu Thr Leu Tyr Lys
                20                  25                  30

Ala Met Lys Gly Ile Gly Thr Asn Glu Gln Ala Ile Ile Asp Val Leu
            35                  40                  45
```

-continued

```
Thr Lys Arg Ser Asn Thr Gln Arg Gln Gln Ile Ala Lys Ser Phe Lys
 50                  55                  60

Ala Gln Phe Gly Lys Asp Leu Thr Glu Thr Leu Lys Ser Glu Leu Ser
 65                  70                  75                  80

Gly Lys Phe Glu Arg Leu Ile Val Ala Leu Met Tyr Pro Pro Tyr Arg
                 85                  90                  95

Tyr Glu Ala Lys Glu Leu His Asp Ala Met Lys Gly Leu Gly Thr Lys
                100                 105                 110

Glu Gly Val Ile Ile Glu Ile Leu Ala Ser Arg Thr Lys Asn Gln Leu
                115                 120                 125

Arg Glu Ile Met Lys Ala Tyr Glu Glu Asp Tyr Gly Ser Ser Leu Glu
130                 135                 140

Glu Asp Ile Gln Ala Asp Thr Ser Gly Tyr Leu Glu Arg Ile Leu Val
145                 150                 155                 160

Cys Leu Leu Gln Gly Ser Arg Asp Asp Val Ser Ser Phe Val Asp Pro
                165                 170                 175

Ala Leu Ala Leu Gln Asp Ala Gln Asp Leu Tyr Ala Ala Gly Glu Lys
                180                 185                 190

Ile Arg Gly Thr Asp Glu Met Lys Phe Ile Thr Ile Leu Cys Thr Arg
                195                 200                 205

Ser Ala Thr His Leu Leu Arg Val Phe Glu Glu Tyr Glu Lys Ile Ala
210                 215                 220

Asn Lys Ser Ile Glu Asp Ser Ile Lys Ser Glu Thr His Gly Ser Leu
225                 230                 235                 240

Glu Glu Ala Met Leu Thr Val Val Lys Cys Thr Gln Asn Leu His Ser
                245                 250                 255

Tyr Phe Ala Glu Arg Leu Tyr Tyr Ala Met Lys Gly Ala Gly Thr Arg
                260                 265                 270

Asp Gly Thr Leu Ile Arg Asn Ile Val Ser Arg Ser Glu Ile Asp Leu
                275                 280                 285

Asn Leu Ile Lys Cys His Phe Lys Lys Met Tyr Gly Lys Thr Leu Ser
290                 295                 300

Ser Met Ile Met Glu Asp Thr Ser Gly Asp Tyr Lys Asn Ala Leu Leu
305                 310                 315                 320

Ser Leu Val Gly Ser Asp Pro Gly Ser Leu Glu Val Leu Phe Gln Gly
                325                 330                 335

Pro Ser Gly Lys Leu Ala Trp Trp Lys Ala Trp Ile Glu Gln Glu Gly
                340                 345                 350

Val Thr Val Lys Ser Ser His Phe Asn Pro Asp Pro Asp Ala Glu
                355                 360                 365

Thr Leu Tyr Lys Ala Met Lys Gly Ile Gly Thr Asn Glu Gln Ala Ile
                370                 375                 380

Ile Asp Val Leu Thr Lys Arg Ser Asn Thr Gln Arg Gln Gln Ile Ala
385                 390                 395                 400

Lys Ser Phe Lys Ala Gln Phe Gly Lys Asp Leu Thr Glu Thr Leu Lys
                405                 410                 415

Ser Glu Leu Ser Gly Lys Phe Glu Arg Leu Ile Val Ala Leu Met Tyr
                420                 425                 430

Pro Pro Tyr Arg Tyr Glu Ala Lys Glu Leu His Asp Ala Met Lys Gly
                435                 440                 445

Leu Gly Thr Lys Glu Gly Val Ile Ile Glu Ile Leu Ala Ser Arg Thr
                450                 455                 460

Lys Asn Gln Leu Arg Glu Ile Met Lys Ala Tyr Glu Glu Asp Tyr Gly
```

-continued

```
465                 470                 475                 480
Ser Ser Leu Glu Glu Asp Ile Gln Ala Asp Thr Ser Gly Tyr Leu Glu
                485                 490                 495
Arg Ile Leu Val Cys Leu Leu Gln Gly Ser Arg Asp Asp Val Ser Ser
                500                 505                 510
Phe Val Asp Pro Ala Leu Ala Leu Gln Asp Ala Gln Asp Leu Tyr Ala
                515                 520                 525
Ala Gly Glu Lys Ile Arg Gly Thr Asp Glu Met Lys Phe Ile Thr Ile
        530                 535                 540
Leu Cys Thr Arg Ser Ala Thr His Leu Leu Arg Val Phe Glu Glu Tyr
545                 550                 555                 560
Glu Lys Ile Ala Asn Lys Ser Ile Glu Asp Ser Ile Lys Ser Glu Thr
                565                 570                 575
His Gly Ser Leu Glu Glu Ala Met Leu Thr Val Val Lys Cys Thr Gln
                580                 585                 590
Asn Leu His Ser Tyr Phe Ala Glu Arg Leu Tyr Tyr Ala Met Lys Gly
        595                 600                 605
Ala Gly Thr Arg Asp Gly Thr Leu Ile Arg Asn Ile Val Ser Arg Ser
        610                 615                 620
Glu Ile Asp Leu Asn Leu Ile Lys Cys His Phe Lys Lys Met Tyr Gly
625                 630                 635                 640
Lys Thr Leu Ser Ser Met Ile Met Glu Asp Thr Ser Gly Asp Tyr Lys
                645                 650                 655
Asn Ala Leu Leu Ser Leu Val Gly Ser Asp Pro
                660                 665
```

MODIFIED ANNEXIN PROTEINS AND METHODS FOR THEIR USE IN ORGAN TRANSPLANTATION

CROSS-REFERENCE TO RELATED APPLICATIONS

This application is a continuation in part of U.S. application Ser. No. 11/078,231, "Modified Annexin Proteins and Methods for Preventing Thrombosis," filed Mar. 10, 2005, which is a continuation in part of U.S. application Ser. No. 10/080,370, "Modified Annexin Proteins and Methods for Preventing Thrombosis," filed Feb. 21, 2002, now U.S. Pat. No. 6,962,903 which claims the benefit under 35 U.S.C. § 119 of U.S. Provisional Application No. 60/270,402, "Optimizing the Annexin Molecule for Preventing Thrombosis," filed Feb. 21, 2001, and U.S. Provisional Application No. 60/332,582, "Modified Annexin Molecule for Preventing Thrombosis and Reperfusion Injury," filed Nov. 21, 2001. U.S. application Ser. No. 11/078,231 also claims the benefit, under 35 U.S.C. § 119, of U.S. Provisional application No. 60/552,428, "The Use Of Modified Annexin To Attenuate Reperfusion Injury," filed Mar. 11, 2004, and U.S. Provisional application No. 60/579,589 "Use of a Modified Annexin to Attenuate Reperfusion Injury," filed Jun. 14, 2004. The disclosure of each of the foregoing patent applications is hereby incorporated by reference herein in their entirety.

FIELD OF THE INVENTION

The present invention relates generally to methods and compositions for treating ischemia-reperfusion injury in organ transplantation and in other medical and surgical disorders. More particularly, it relates to modified annexin proteins and methods for their use.

BACKGROUND OF THE INVENTION

Thrombosis—the formation, development, or presence of a blood clot (thrombus) in a blood vessel—is the most common severe medical disorder. The most frequent example of arterial thrombosis is coronary thrombosis, which leads to occlusion of the coronary arteries and often to myocardial infarction (heart attack). More than 1.3 million patients are admitted to the hospital for myocardial infarction each year in North America. The standard therapy is administration of a thrombolytic protein by infusion. Thrombolytic treatment of acute myocardial infarction is estimated to save 30 lives per 1000 patients treated; nevertheless the 30-day mortality for this disorder remains substantial (Mehta et al., Lancet 356: 449-454 (2000)). The disclosure of Mehta, et al., and the disclosure of all other patents, patent applications and publications referred to herein, are incorporated herein by reference in their entirety). It would be convenient to administer antithrombotic and thrombolytic agents by bolus injection, since they might be used before admission to hospital with additional benefit (Rawles, J. Am. Coll. Cardiol. 30:1181-1186 (1997), incorporated herein by reference). However, bolus injection (as opposed to a more gradual intravenous infusion) significantly increases the risk of cerebral hemorrhage (Mehta et al., 2000). The development of an agent able to prevent thrombosis and/or increase thrombolysis, without augmenting the risk of bleeding, would be desirable.

Unstable angina, caused by inadequate oxygen delivery to the heart due to coronary occlusion, is the most common cause of admission to hospital, with 1.5 million cases a year in the United States alone. When patients with occlusion of coronary arteries are treated with angioplasty and stenting, the use of an antibody against platelet gp IIb/IIIa decreases the likelihood of restenosis. However, the same antibody has shown no benefit in unstable angina without angioplasty, and a better method for preventing coronary occlusion in these patients is needed.

Another important example of arterial thrombosis is cerebral thrombosis. Intravenous recombinant tissue plasminogen activator (rtPA) is the only treatment for acute ischemic stroke that is approved by the Food and Drug Administration. The earlier it is administered the better (Ernst et al., Stroke 31:2552-2557 (2000), incorporated herein by reference). However, intravenous rtPA administration is associated with increased risk of intracerebral hemorrhage. Full-blown strokes are often preceded by transient ischemic attacks (TIA), and it is estimated that about 300,000 persons suffer TIA every year in the United States. It would be desirable to have a safe and effective agent that could be administered as a bolus and would for several days prevent recurrence of cerebral thrombosis without increasing the risk of cerebral hemorrhage. Thrombosis also contributes to peripheral arterial occlusion in diabetics and other patients, and an efficacious and safe antithrombotic agent for use in such patients is needed.

Venous thrombosis is a frequent complication of surgical procedures such as hip and knee arthroplasties. It would be desirable to prevent thrombosis without increasing hemorrhage into the field of operation. Similar considerations apply to venous thrombosis associated with pregnancy and parturition. Some persons are prone to repeated venous thrombotic events and are currently treated by antithrombotic agents such as coumarin-type drugs. The dose of such drugs must be titrated in each patient, and the margin between effective antithrombotic doses and those increasing hemorrhage is small. Having a treatment with better separation of antithrombotic activity from increased risk of bleeding is desirable. All of the recently introduced antithrombotic therapies, including ligands of platelet gp IIb/IIIa, low molecular weight heparins, and a pentasaccharide inhibitor of factor Xa, carry an increased risk of bleeding (Levine et al., Chest 119:108S-121S (2001), incorporated herein by reference). Hence there is a need to explore alternative strategies for preventing arterial and venous thrombosis without augmenting the risk of hemorrhage.

To inhibit the extension of arterial or venous thrombi without increasing hemorrhage, it is necessary to exploit potential differences between mechanisms involved in hemostasis and those involved in thrombosis in large blood vessels. Primary hemostatic mechanisms include the formation of platelet microaggregates, which plug capillaries and accumulate over damaged or activated endothelial cells in small blood vessels. Inhibitors of platelet aggregation, including agents suppressing the formation or action of thromboxane $A_2$, ligands of gp IIa/IIIb, and drugs acting on ADP receptors such as clopidogrel (Hallopeter, Nature 409:202-207 (2001), incorporated herein by reference), interfere with this process and therefore increase the risk of bleeding (Levine et al., 2001). In contrast to microaggregate formation, occlusion by an arterial or venous thrombus requires the continued recruitment and incorporation of platelets into the thrombus. To overcome detachment by shear forces in large blood vessels, platelets must be bound tightly to one another and to the fibrin network deposited around them.

Evidence has accumulated that the formation of tight macroaggregates of platelets is facilitated by a cellular and a humoral amplification mechanism, which reinforce each other. In the cellular mechanism, the formation of relatively loose microaggregates of platelets, induced by moderate concentrations of agonists such as ADP, thromboxane $A_2$, or collagen, is accompanied by the release from platelet α-granules of the 85-kD protein Gas6 (Angelillo-Scherrer et al., *Nature Medicine* 7:215-221 (2001), incorporated herein by reference). Binding of released Gas6 to receptor tyrosine kinases (Axl, Sky, Mer) expressed on the surface of platelets induces complete degranulation and the formation of tight macroaggregates of these cells. In the humoral amplification mechanism, a prothrombinase complex is formed on the surface of activated platelets and microvesicles. This generates thrombin and fibrin. Thrombin is itself a potent platelet activator and inducer of the release of Gas6 (Ishimoto and Nakano, *FEBS Lett.* 446:197-199 (2000), incorporated herein by reference). Fully activated platelets bind tightly to the fibrin network deposited around them. Histological observations show that both platelets and fibrin are necessary for the formation of a stable coronary thrombus in humans (Falk et al. Interrelationship between atherosclerosis and thrombosis. In Vanstraete et al. (editors), *Cardiovascular Thrombosis: Thrombocardiology and Thromboneurology.* Philadelphia: Lipincott-Raven Publishers (1998), pp. 45-58, incorporated herein by reference). Another platelet adhesion molecule, amphoterin, is translocated to the platelet surface during activation, and binds anionic phospholipid (Rouhainen et al., *Thromb. Hemost.* 84:1087-1094 (2000), incorporated herein by reference). Like Gas6, amphoterin could form a bridge during platelet aggregation.

The question arises whether it is possible to inhibit these amplification mechanisms but not the initial platelet aggregation step, thereby preventing thrombosis without increasing hemorrhage. The importance of cellular amplification has recently been established by studies of mice with targeted inactivation of Gas6 (Angelillo-Scherrer et al., 2001). The Gas6-/- mice were found to be protected against thrombosis and embolism induced by collagen and epinephrine. However, the Gas6-/- mice did not suffer from spontaneous hemorrhage and had normal bleeding after tail clipping. Furthermore, antibodies against Gas6 inhibited platelet aggregation in vitro as well as thrombosis induced in vivo by collagen and epinephrine. In principle, such antibodies, or ligands competing for Gas6 binding to receptor tyrosine kinases, might be used to inhibit thrombosis. However, in view of the potency of humoral amplification, it might be preferable to inhibit that step. Ideally such an inhibitor would also have additional suppressive activity on the Gas6-mediated cellular amplification mechanism.

A strategy for preventing both cellular and humoral amplification of platelet aggregation is provided by the annexins, a family of highly homologous antithrombotic proteins of which ten are expressed in several human tissues (Benz and Hofmann, *Biol. Chem.* 378:177-183 (1997), incorporated herein be reference). Annexins share the property of binding calcium and negatively charged phospholipids, both of which are required for blood coagulation. Under physiological conditions, negatively charged phospholipid is mainly supplied by phosphatidylserine (PS) in activated or damaged cell membranes. In intact cells, PS is confined to the inner leaflet of the plasma membrane bilayer and is not accessible on the surface. When platelets are activated, the amounts of PS accessible on their surface, and therefore the extent of annexin binding, are greatly increased (Sun et al., *Thrombosis Res.* 69:289-296 (1993), incorporated herein by reference). During activation of platelets, microvesicles are released from their surfaces, greatly increasing the surface area expressing anionic phospholipids with procoagulant activity (Merten et al., *Circulation* 99:2577-2582 (1999); Chow et al., *J. Lab. Clin. Med.* 135:66-72 (2000), both incorporated herein by reference). These may play an important role in the propagation of platelet-mediated arterial thrombi.

Proteins involved in the blood coagulation cascade (factors X, Xa, and Va) bind to membranes bearing PS on their surfaces, and to one another, forming a stable, tightly bound prothrombinase complex. Several annexins, including I, II, IV, V, and VIII, bind PS with high affinity, thereby preventing the formation of a prothrombinase complex and exerting antithrombotic activity. Annexin V binds PS with very high affinity ($K_d$=1.7 nmol/L), greater than the affinity of factors X, Xa, and Va for negatively charged phospholipids (Thiagarajan and Tait, *J. Biol. Chem.* 265:17420-17423 (1990), incorporated herein by reference). Tissue factor-dependent blood coagulation on the surface of activated or damaged endothelial cells also requires surface expression of PS, and annexin V can inhibit this process (van Heerde et al., *Arterioscl. Thromb.* 14:824-830 (1994), incorporated herein by reference), although annexin is less effective in this activity than in inhibition of prothrombinase generation (Rao et al., *Thromb. Res.* 62:517-531 (1992), incorporated herein by reference).

The binding of annexin V to activated platelets and to damaged cells probably explains the selective retention of the protein in thrombi. This has been shown in experimental animal models of venous and arterial thrombosis (Stratton et al., *Circulation* 92:3113-3121 (1995); Thiagarajan and Benedict, *Circulation* 96:2339-2347 (1997), both incorporated herein by reference), and labeled annexin has been proposed for medical imaging of vascular thrombi in humans, with reduced noise and increased safety (Reno and Kasina, International Patent Application PCT/US95/07599 (WO 95/34315) (published Dec. 21, 1995), incorporated herein by reference). The binding to thrombi of a potent antithrombotic agent such as annexin V provides a strategy for preventing the extension or recurrence of thrombosis. Transient myocardial ischemia also increases annexin V binding (Dumont et al., *Circulation* 102:1564-1568 (2000), incorporated herein by reference). Annexin V imaging in humans has shown increased binding of the protein in transplanted hearts when endomyocardial biopsy has demonstrated vascular rejection (Acio et al., *J. Nuclear Med.* 41 (5 Suppl.):127P (2000), incorporated herein by reference). This binding is presumably due to PS exteriorized on the surface of damaged endothelial cells, as well as of apoptotic myocytes in hearts that are being rejected. It follows that administration of annexin after myocardial infarction should prevent the formation of prothrombotic complexes on both platelets and endothelial cells, thereby preventing the extension or recurrence of thrombosis. Annexin V binding is also augmented following cerebral hypoxia in humans (D'Arceuil et al., *Stroke* 2000: 2692-2700 (2000), incorporated herein by reference), which supports the hypothesis that administration of annexin following TIA may decrease the likelihood of developing a full-blown stroke.

Annexins have shown anticoagulant activity in several in vitro thrombin-dependent assays, as well as in experimental animal models of venous thrombosis (Römisch et al., *Thrombosis Res.* 61:93-104 (1991); Van Ryn-McKenna et al., *Thrombosis Hemostasis* 69:227-230 (1993), both incorporated herein by reference) and arterial thrombosis (Thiagarajan and Benedict, 1997). Remarkably, annexin in antithrombotic doses had no demonstrable effect on traditional ex vivo clotting tests in treated rabbits (Thiagarajan and Benedict, 1997) and did not significantly prolong bleeding times of treated rats (Van Ryn-McKenna et al., 1993). In treated rabbits annexin did not increase bleeding into a surgical incision (Thiagarajan and Benedict, 1997). Thus, uniquely among all the agents so far investigated, annexins exert antithrombotic activity without increasing hemorrhage. Annexins do not inhibit platelet aggregation triggered by collagen or thrombin (Sun, et al., *Thrombosis Res.* 69: 281, 1993)), and platelet aggregation is the primary hemostatic mechanism. In the walls of damaged blood vessels and in extravascular tissues, the tissue factor/VIIa complex also exerts hemostatic effects, and this system is less susceptible to inhibition by annexin V than is the prothrombinase complex (Rao et al., 1992). This is one argument for confining administered annexin V to the vascular compartment as far as possible; the risk of hemorrhage is likely to be reduced.

Despite such promising results for preventing thrombosis, a major problem associated with the therapeutic use of annexins is their short half-life in the circulation, estimated in experimental animals to be 5 to 15 minutes (Römisch et al., 1991; Stratton et al., 1995; Thiagarajan and Benedict, 1997); annexin V also has a short half-life in the circulation of humans (Strauss et al., *J. Nuclear Med.* 41 (5 Suppl.): 149P (2000), incorporated herein by reference). Most of the annexin is lost into the urine, as expected of a 36 kDa protein (Thiagarajan and Benedict, 1997). There is a need, therefore, for a method of preventing annexin loss from the vascular compartment into the extravascular compartment and urine, thereby prolonging antithrombotic activity following a single injection.

Organ transplantation is a widely used procedure in many countries. It allows survival of patients who would otherwise die of heart, liver or lung disease, and provides a better quality of life for patients on renal dialysis. Because there is a shortage of organs for transplantation, it would be advantageous if organs from non-ideal, extended-criteria donors could be transplanted successfully. Pretransplant correlates of diminished graft survival include advanced donor age, longstanding donor hypertension or diabetes mellitus, non-heartbeating cadaver donors and prolonged cold preservation time (A. O. Ojo et al. J. Am. Soc. Nephrol. 2001; 12: 589). The outcome of liver transplants is less successful if the donor organs are steatotic (Amersi et al. Proc. Natl. Acad. Sci. U.S.A. 2002; 99: 8915). Accumulation of fat in the liver is common, especially among ageing donors.

Despite advances in surgical technique, patient management and immunosuppression, ischemia-reperfusion injury (IRI) remains an important clinical problem. During recovery and preservation organs are anoxic, as they are in ischemia, and following transplantation they are reperfused. This results in IRI, which is estimated to account for as much as 10% of early graft loss in the case of transplanted livers (Amersi et al. J. Clin. Invest. 1999; 104: 1631). In addition, ischemia of longer than 12 hours is highly correlated with primary nonfunction of transplanted livers, as well as an increase incidence of both acute and chronic rejection (Fellstrom et al. Transplant Proc. 1998; 30: 4278).

Despite many attempts, reviewed by Selzner et al. (Gastroenterology 2003; 125: 917), no method for decreasing IRI has become widely used in organ grafting. It would be desirable to develop a therapeutic agent or procedure which attenuates IRI following organ transplantation.

SUMMARY OF THE INVENTION

The present invention provides compounds and methods for preventing arterial or venous thrombosis. Recombinant human annexins are modified in such a way that its half-life in the vascular compartment is prolonged. This can be achieved in a variety of ways; three embodiments are an annexin coupled to polyethylene glycol, a homopolymer or heteropolymer of annexin, and a fusion protein of annexin with another protein (e.g., the Fc portion of immunoglobulin). The modified annexin binds with high affinity to phosphatidylserine on the surface of activated platelets or injured cells, thereby preventing the binding of Gas6 as well as procoagulant proteins and the formation of a prothrombinase complex. Modified annexin therefore inhibits both the cellular and humoral mechanisms by which platelet aggregation is amplified, thereby preventing thrombosis.

In one embodiment, the present invention provides an isolated modified annexin protein containing an annexin protein, preferably annexin V, coupled to polyethylene glycol (PEG). Preferably, at least two PEG chains are coupled to a single annexin molecule, with each PEG having a molecular weight of at least 5 kDa, more preferably at least 10 kDa, and most preferably at least 15 kDa. In an alternative embodiment, an isolated modified annexin protein contains an annexin protein coupled to at least one additional protein, such as an additional annexin protein (forming a homodimer) or the Fc portion of immunoglobulin. The additional protein preferably has a molecular weight of at least 30 kDa. Also provided by the present invention are pharmaceutical compositions containing an antithrombotically effective amount of any of the modified annexin proteins of the invention.

In methods of the invention, the modified annexin is administered to a subject at risk of thrombosis in a pharmaceutical composition having an antithrombotically effective amount of any one of the modified annexin proteins of the present invention. For example, the pharmaceutical composition can be administered after an arterial thrombosis such as coronary thrombosis, cerebral thrombosis, or a transient cerebral ischemic attack. It can also be administered after a surgical operation associated with venous thrombosis. Additionally, it can be administered to subjects having conditions subject to arterial or venous thrombosis, such as diabetes, pregnancy, or parturition.

Also provided by the present invention are an isolated nucleic acid molecule encoding a homodimer of annexin, a recombinant molecule containing at least a portion of the nucleic acid molecule, and a recombinant cell containing at least a portion of the nucleic acid molecule. The recombinant cell is cultured under suitable conditions in a method of the invention to produce a homodimer of annexin.

The present invention also provides a method for screening for a modified annexin protein that modulates thrombosis using a thrombosis test system. In some embodiments, the test system is an in vitro coagulation assay (Kuypers et al., Blood 104, 441a, 2004). In this embodiment, the assay comprises human cells with externalized PS to which purified human blood coagulation proteins bind and generate a prothrombin complex. The modified annexin binds to PS, competing with the coagulation proteins, and thereby inhibits thrombin generation.

Also provided by the present invention is a method for in vivo screening for a modified annexin protein. In this method, a thrombosis animal model is contacted with a test modified annexin protein, after which the in vivo anticoagulation activity and increase in hemorrhage of the test modified annexin protein is assessed. The anticoagulation activity and time are compared with the anticoagulation activity and time of annexin, and the amount of hemorrhage is compared with hemorrhage in the animal model in the absence of the test modified annexin protein.

Thus the invention provides a method of treating a subject at risk of thrombosis comprising administering to said subject an antithrombotically effective amount of an isolated modified annexin protein comprising an annexin dimer. The isolated modified annexin protein is administered after coronary thrombosis, after an overt cerebral thrombosis, after transient cerebral ischemic attack, after a surgical operation associated with venous thrombosis, wherein said subject is diabetic and said thrombosis is arterial thrombosis, or during a condition selected from the group consisting of pregnancy and parturition. The isolated modified annexin protein is administered in a range from 0.1 mg/kg to 1.0 mg/kg.

The present invention also provides a method of inhibiting the attachment of leukocytes to endothelial cells comprising administering an effective amount of an isolated modified annexin protein comprising an annexin dimer to a patient in need thereof. In some embodiments, the method further comprises reducing endothelial cell damage.

The present invention also provides a method of treating a subject at risk of thrombosis comprising administering to said subject an antithrombotically effective amount of a protein having an affinity for phosphatidylserine that is at least 10% of the affinity of annexin V for phosphatidylserine, including wherein said protein is a monoclonal or polyclonal antibody.

The present invention provides a method of protecting organs or tissue susceptible to IRI, comprising contacting said organs or tissue with isolated modified annexin protein comprising an annexin dimer. In some embodiments, said organs or tissue are contacted with said isolated modified annexin protein comprising an annexin dimer by administering to a patient who is a recipient of an organ transplant, a therapeutic composition comprising isolated modified annexin protein comprising an annexin dimer. In some embodiments, the annexin dimer is administered in an intravascular dose of 10 to 1000 µg/kg. In other embodiments, the annexin dimer is administered in an intravascular dose of 100 to 500 µg/kg.

In some embodiments, the therapeutic composition is administered to the recipient patient up to six hours prior to the reperfusion period. In other embodiments, the therapeutic composition is administered to the recipient patient up to one hour after the reperfusion period. In other embodiments, the therapeutic composition is intravenously administered to the recipient patient during the transplantation. In some embodiments the therapeutic composition is administered to a patient with coronary, cerebral or other thrombosis as soon as possible after the vaso-occlusive event. In another embodiment, the therapeutic composition is administered during a surgical operation to decrease the likelihood of thrombosis and/or embolism. In yet another embodiment the therapeutic composition is administered to an organ graft recipient before, during or after the operation to attenuate ischemia-reperfusion injury.

In some embodiments, an isolated modified annexin protein comprising an annexin dimer comprises SEQ ID NO:6, SEQ ID NO:13, or SEQ ID NO:23.

In still other embodiments, the organs or tissue comprise organ or tissue transplants which are contacted with an isolated modified annexin protein comprising an annexin dimer by perfusing or flushing them ex vivo with a solution containing isolated modified annexin protein comprising an annexin dimer in a concentration of about 0.1 to 1 mg/l. In some embodiments, wherein said organs or tissue are perfused with a solution containing, in addition to isolated modified annexin protein comprising an annexin dimer, at least one component selected from the group consisting of electrolytes and cell-protecting agents.

The present invention also provides a method of protecting organ or tissue transplants against reperfusion injury and dysfunction, comprising contacting said organ or tissue with a preservation fluid for perfusion and storage or rinsing of the organ, or tissue transplants prior to the implantation of said organ or tissue in a patient requiring such implantation, wherein said preservation fluid contains an isolated modified annexin protein comprising an annexin dimer in a concentration sufficient to prevent IRI after ischemia.

In some embodiments, the isolated modified annexin protein comprising an annexin dimer is added in a concentration of about 0.1 to 1 mg/l of preservation or rinse fluid.

In other embodiments, the isolated modified annexin protein comprising an annexin dimer comprises SEQ ID NO:6, SEQ ID NO:13, or SEQ ID NO:17.

The present invention also provides method of protecting organs against IRI comprising administering an effective amount of an isolated modified annexin protein comprising an annexin dimer, individually or in combination to a patient undergoing surgical operation.

The present invention further provides a method of protecting organs or tissue susceptible to IRI, comprising contacting said organs or tissue with an effective amount of a protein having an affinity for phosphatidylserine that is at least 10% of the affinity of annexin V for phosphatidylserine. In some embodiments, the protein is a monoclonal or polyclonal antibody.

The present invention also provides an isolated polynucleotide selected from the group consisting of: (a) an isolated polynucleotide comprising a polynucleotide sequence having at least 95% identity to the polynucleotide sequence of SEQ ID NO: 17 or SEQ ID NO:23; (b) an isolated polynucleotide comprising the polynucleotide of SEQ ID NO:17 or SEQ ID NO:23; (c) an isolated polynucleotide having at least 95% identity to the polynucleotide of SEQ ID NO:17 or SEQ ID NO:23; (d) the isolated polynucleotide of SEQ ID NO:17 or SEQ ID NO:23; (e) an isolated polynucleotide comprising a polynucleotide sequence encoding a polypeptide sequence having at least 95% identity to the polypeptide sequence of SEQ ID NO:19 or SEQ ID NO:23; (f) an isolated polynucleotide comprising a polynucleotide sequence encoding the polypeptide of SEQ ID NO:19 or SEQ ID NO:23; (g) an isolated polynucleotide having a polynucleotide sequence encoding a polypeptide sequence having at least 95% identity to the polypeptide sequence of SEQ ID NO:19 or SEQ ID NO:23; (h) an isolated polynucleotide encoding the polypeptide of SEQ ID NO:19 or SEQ ID NO:23; (i) a polynucleotide which is the RNA equivalent of a polynucleotide of (a) to (h); and (j) a polynucleotide sequence complementary to a polynucleotide of (a) to (i), wherein the polynucleotides of (a)-(k) encode a polypeptide having the ability to bind phosphatidylserine on cell surfaces.

The present invention also provides an isolated polypeptide selected from the group consisting of: (a) an isolated polypeptide encoded by a polynucleotide comprising the sequence of SEQ ID NO:19 or SEQ ID NO:23; (b) an isolated polypeptide comprising a polypeptide sequence having at least 95% identity to the polypeptide sequence of SEQ ID NO:19 or SEQ ID NO:23; (c) an isolated polypeptide comprising the polypeptide sequence of SEQ ID NO:19 or SEQ ID NO:23; (d) an isolated polypeptide having at least 95% identity to the polypeptide sequence of SEQ ID NO:19 or SEQ ID NO:23; and (e) the polypeptide sequence of SEQ ID NO:19 or SEQ ID NO:23; wherein the polypeptides of (a)-(e) bind phosphatidylserine on cell surfaces.

In still further embodiments, the present invention provides a method of increasing the duration of survival of blood platelets, comprising adding an isolated modified annexin protein comprising an annexin dimer to stored platelets. The addition may be in a platelet storage medium. The addition may also be in a patient to whom platelets were administered, including the case where the patient is the recipient of a liver graft, including a thrombocytopenic liver graft patient.

BRIEF DESCRIPTION OF THE FIGURES

FIGS. 1A-C show the structural scheme of two modified annexin embodiments. FIG. 1A shows the structural scheme of human annexin V homodimer with a His-tag; FIG. 1B shows the structural scheme of the human annexin V homodimer without a His-tag. FIG. 1C shows a DNA construct for making a homodimer of annexin V (SEQ ID NO: 28 represents the start codon, FLAG epitope. and three restriction sites; SEQ ID NO: 29 represents the nucleic acid sequence linking a first annexin nucleic acid sequence and second annexin nucleic acid sequence).

FIGS. 3A-B show serum samples recovered 5 minutes and 20 minutes after injection of AV into mice, respectively. FIGS. 3C-E show serum samples recovered 5 minutes, 25 minutes and 120 minutes after injection of annexin V homodimer (DAV) into mice, respectively.

FIG. 4 shows $PLA_2$-induced hemolysis of PS-exposing RBC. A mixture of normal ($1\times10^7$/ml) and PS exposing ($1\times10^7$/ml) RBCs was incubated with 100 ng/ml pancreatic $PLA_2$ ($pPLA_2$) or secretory $PLA_2$ ($sPLA_2$). Hemolysis was measured as a function of time and expressed relative to 100% hemolysis induced by osmotic shock. The percentage of PS-exposing cells was determined by flow cytometry of the cell suspension after labeling with biotinylated DAV and R-phycoerythrein-conjugated streptavidin.

DETAILED DESCRIPTION OF THE INVENTION

Figure 2A:
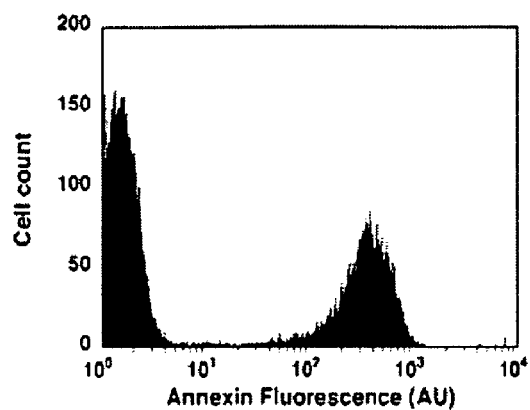
FIGS. 2A-D show the results of flowcytometric analysis of a mixture of normal ($1\times10^7$/ml) and PS exposing ($1\times10^7$/ml) RBCs incubated with 0.2 μg/ml biotinylated AV (FIG. 2A); 0.2 μg/ml biotinylated DAV (FIG. 2B); 0.2 μg/ml biotinylated AV and 0.2 μg/ml nonbiotinylated DAV (FIG. 2C); and 0.2 μg/ml biotinylated DAV and 0.2 μg/ml nonbiotinylated AV (FIG. 2D), in each case, followed by R-phycoerythrein-conjugated streptavidin.
Figure 2B:
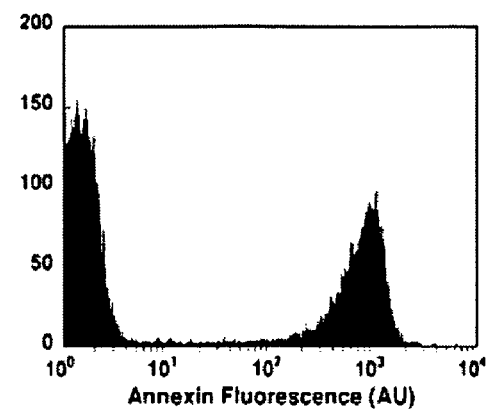
Figure 2C:
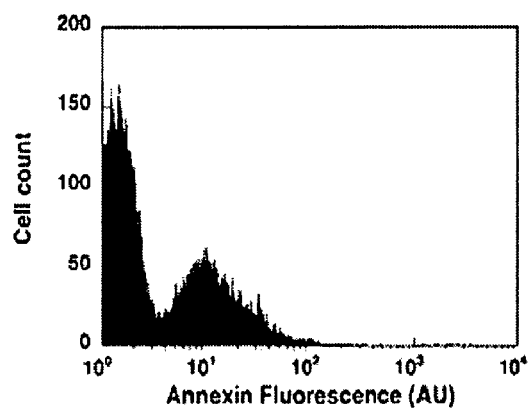
Figure 2D:
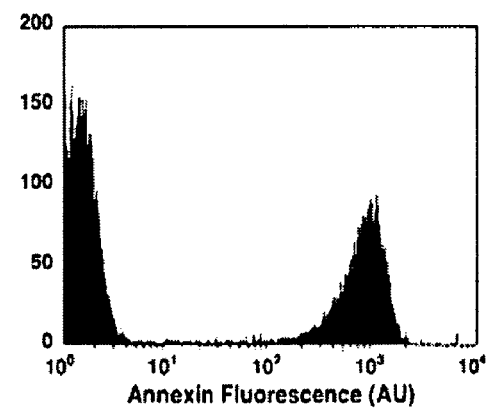

The present invention provides compounds and methods for preventing thrombosis in mammals without increasing hemorrhage. The invention relies in part on the recognition that the primary mechanisms of platelet aggregation are different from the mechanisms of amplifying platelet aggregation, which are required for the formation of an arterial or venous thrombus. By inhibiting thrombus formation but not primary platelet aggregation, thrombosis can be prevented without increasing hemorrhage.

Compounds of the invention include any product containing annexin amino acid sequences that have been modified to increase the half-life of the product in humans or other mammals. Where "amino acid sequence" is recited herein to refer to an amino acid sequence of a naturally-occurring protein molecule, "amino acid sequence" and like terms, such as "polypeptide" or "protein," are not meant to limit the amino acid sequence to the complete, native amino acid sequence associated with the recited proteins. The annexins are a family of homologous phospholipid-binding membrane proteins, of which ten represent distinct gene products expressed in mammals (Benz and Hofmann, 1997). Crystallographic analysis has revealed a common tertiary structure for all the family members so far studied, exemplified by annexin V (Huber et al., *EMBO Journal* 9:3867 (1990), incorporated herein by reference). The core domain is a concave discoid structure that can be closely apposed to phospholipid membranes. It contains four subdomains, each consisting of a 70-amino-acid annexin repeat made up of five α-helices. The annexins also have a more hydrophilic tail domain that varies in length and amino acid sequence among the different annexins. The sequences of genes encoding annexins are well known (e.g., Funakoshi et al., *Biochemistry* 26:8087-8092 (1987) (annexin V), incorporated herein by reference).

Annexin proteins include proteins of the annexin family, such as Annexin II (lipocortin 2, calpactin 1, protein I, p36, chromobindin 8), Annexin III (lipocortin 3, PAP-III), Annexin IV (lipocortin 4, endonexin I, protein II, chromobindin 4), Annexin V (Lipocortin 5, Endonexin 2, VAC-alpha, Anchorin CII, PAP-I), Annexin VI (Lipocortin 6, Protein III, Chromobindin 20, p68, p70), Annexin VII (Synexin), Annexin VIII (VAC-beta), Annexin XI (CAP-50), and Annexin XIII (ISA), Annexin IV shares many of the same properties of Annexin V. Like annexin V, Annexin IV binds to acidic phospholipid membranes in the presence of calcium. Annexin IV is a close structural homologue of Annexin V. The sequence of Annexin IV is known. Hamman et al., Biochem. Biophys. Res. Comm., 156:660-667 (1988). Annexin IV belongs to the annexin family of calcium-dependent phospholipid binding proteins. Its functions are still not clearly defined.

Annexin IV (endonexin) is a 32 kDa, calcium-dependent membrane-binding protein. The translated amino acid sequence of Annexin IV shows the four domain structure characteristic of proteins in this class. Annexin IV has 45-59% identity with other members of its family and shares a similar size and exon-intron organization. Isolated from human placenta, Annexin IV encodes a protein that has in vitro anticoagulant activity and inhibits phospholipase $A_2$ activity. Annexin IV is almost exclusively expressed in epithelial cells.

Annexin VIII belongs to the family of $CA^{2+}$ dependent phospholipid binding proteins (annexins) and has high sequence identity to Annexin V (56%). Hauptmann, et al., Eur J Biochem. 1989 Oct 20; 185(1):63-71. It was initially isolated as a 2.2 kb vascular anticoagulant-beta. Annexin VIII is neither an extracellular protein nor associated with the cell surface. It may not play a role in blood coagulation in vivo. Its physiological role remains unknown. It is expressed at low levels in human placenta and shows restricted expression in lung, endothelia and skin, liver and kidney.

In the present invention, annexin proteins are modified to increase their half-life in humans or other mammals. In some embodiments, the annexin protein is annexin V, annexin IV or annexin VIII. One suitable modification of annexin is an increase in its effective size, which prevents loss from the vascular compartment into the extravascular compartment and urine, thereby prolonging antithrombotic activity following a single injection. Any increase in effective size that maintains a sufficient binding affinity with phosphatidylserine is within the scope of the present invention.

In one embodiment of the invention, a modified annexin contains a recombinant human annexin protein coupled to polyethylene glycol (PEG) in such a way that the modified annexin is capable of performing the function of annexin in a phosphatidylserine (PS)-binding assay. The antithrombotic action of the intravenously administered annexin-PEG conjugate is prolonged as compared with that of the free annexin. The recombinant annexin protein coupled to PEG can be annexin V protein or another annexin protein. In one embodiment, the annexin protein is annexin V, annexin IV or annexin VIII.

PEG consists of repeating units of ethylene oxide that terminate in hydroxyl groups on either end of a linear or, in some cases, branched chain. The size and molecular weight of the coupled PEG chain depend upon the number of ethylene oxide units it contains, which can be selected. For the present invention, any size of PEG and number of PEG chains per annexin molecule can be used such that the half-life of the modified annexin is increased, relative to annexin, while preserving the function of binding of the modified molecule to PS. As stated above, sufficient binding includes binding that is diminished from that of the unmodified annexin, but still competitive with the binding of Gas6 and factors of the prothrombinase complex and therefore able to prevent thrombosis. The optimal molecular weight of the conjugated PEG varies with the number of PEG chains. In one embodiment, two PEG molecules of molecular weight of at least about 15 kDa each are coupled to each annexin molecule. The PEG molecules can be linear or branched. The calcium-dependent binding of annexins to PS is affected not only by the size of the coupled PEG molecules, but also the sites on the protein to which PEG is bound. Optimal selection ensures that desirable properties are retained. Selection of PEG attachment sites is facilitated by knowledge of the three-dimensional structure of the molecule and by mutational and crystallographic analyses of the interaction of the molecule with phospholipid membranes (Campos et al., *Biochemistry* 37:8004-8008 (1998), incorporated herein by reference).

In the area of drug delivery, PEG derivatives have been widely used in covalent attachment (referred to as pegylation) to proteins to enhance solubility, as well as to reduce immunogenicity, proteolysis, and kidney clearance. The superior clinical efficacy of recombinant products coupled to PEG is well established. For example, PEG-interferon alpha-2a administered once weekly is significantly more effective against hepatitis C virus than three weekly doses of the free interferon (Heathcote et al., *N. Engl. J. Med.* 343:1673-1680 (2000), incorporated herein by reference). Coupling to PEG has been used to prolong the half-life of recombinant proteins in vivo (Knauf et al., *J. Biol. Chem.* 266:2796-2804 (1988), incorporated herein by reference), as well as to prevent the enzymatic degradation of recombinant proteins and to decrease the immunogenicity sometimes observed with homologous products (references in Hermanson, Bioconjugate techniques. New York, Academic Press (1996), pp. 173-176, incorporated herein by reference).

In another embodiment of the invention, the modified annexin protein is a polymer of annexin proteins that has an increased effective size. It is believed that the increase in effective size results in prolonged half-life in the vascular compartment and prolonged antithrombotic activity. One such modified annexin is a dimer of annexin proteins. In one embodiment, the dimer of annexin is a homodimer of annexin V, annexin IV or annexin VIII. In another embodiment, the dimer of annexin is a heterodimer of annexin V and other annexin protein (e.g., annexin IV or annexin VIII), annexin IV and another annexin protein (e.g., annexin V or annexin VIII) or annexin VIII and another annexin protein (e.g., annexin V or annexin IV). Another such polymer is the heterotetramer of annexin II with p11, a member of the S100 family of calcium-binding proteins. The binding of an S100 protein to an annexin increases the affinity of the annexin for $Ca^{2+}$. The annexin homopolymer or heterotetramer can be produced by bioconjugate methods or recombinant methods, and be administered by itself or in a PEG-conjugated form.

In some embodiments, the modified annexins have increased affinity for PS. As described in Example 4, a homodimer of human annexin V (DAV) was prepared in using well-established methods of recombinant DNA technology. The annexin molecules of the homodimer are joined through peptide bonds to a flexible linker (FIG. 1). In some embodiments, the flexible linker contains a sequence of amino acids flanked by a glycine and a serine residue at either end to serve as swivels. The linker preferably comprises one or more such "swivels." Preferably, the linker comprises 2 swivels which may be separated by at least 2 amino acids, more particularly by at least 4 amino acids, more particularly by at least 6 amino acids, more particularly by at least 8 amino acids, more particularly by at least 10 amino acids. Preferably, the overall length of the linker is 5-30 amino acids, 5-20 amino acids, 5-10 amino acids, 10-15 amino acids, or 10-20 amino acids. The dimer can fold in such a way that the convex surfaces of the monomer, which bind $Ca^{2+}$ and PS, can both gain access to externalized PS. Flexible linkers are known in the art, for example, (GGGGS)(n) SEQ ID NO: 24 (n=3-4), and helical linkers, (EAAAK)(n) SEQ ID NO: 25 (n=2-5), described in Arai, et al., Proteins. 2004 Dec. 1; 57(4):829-38. As described in Example II, the annexin V homodimer out-competes annexin monomer in binding to PS on cell surfaces (FIG. 2).

In another embodiment of the invention, recombinant annexin is expressed with, or chemically coupled to, another protein such as the Fc portion of immunoglobulin. Such expression or coupling increases the effective size of the molecule, preventing the loss of annexin from the vascular compartment and prolonging its anticoagulant action.

Preferably, a modified annexin protein of the invention is an isolated modified annexin protein. The modified annexin protein can contain annexin II, annexin IV, annexin V, or annexin VIII. In some embodiments, the protein is modified human annexin. In some embodiments, the modified annexin contains recombinant human annexin. According to the present invention, an isolated or biologically pure protein is a protein that has been removed from its natural environment. As such, "isolated" and "biologically pure" do not necessarily reflect the extent to which the protein has been purified. An isolated modified annexin protein of the present invention can be obtained from its natural source, can be produced using recombinant DNA technology, or can be produced by chemical synthesis. As used herein, an isolated modified annexin protein can be a full-length modified protein or any homologue of such a protein. It can also be (e.g., for a pegylated protein) a modified full-length protein or a modified homologue of such a protein.

The minimal size of a protein homologue of the present invention is a size sufficient to be encoded by a nucleic acid molecule capable of forming a stable hybrid with the complementary sequence of a nucleic acid molecule encoding the corresponding natural protein. As such, the size of the nucleic acid molecule encoding such a protein homologue is dependent on nucleic acid composition and percent homology between the nucleic acid molecule and complementary sequence as well as upon hybridization conditions per se (e.g., temperature, salt concentration, and formamide concentration). The minimal size of such nucleic acid molecules is typically at least about 12 to about 15 nucleotides in length if the nucleic acid molecules are GC-rich and at least about 15 to about 17 bases in length if they are AT-rich. As such, the minimal size of a nucleic acid molecule used to encode a protein homologue of the present invention is from about 12 to about 18 nucleotides in length. There is no limit on the maximal size of such a nucleic acid molecule in that the nucleic acid molecule can include a portion of a gene, an entire gene, or multiple genes or portions thereof. Similarly, the minimal size of an annexin protein homologue or a modified annexin protein homologue of the present invention is from about 4 to about 6 amino acids in length, with sizes depending on whether a full-length, multivalent (i.e., fusion protein having more than one domain, each of which has a function) protein, or functional portions of such proteins are desired. Annexin and modified annexin homologues of the present invention preferably have activity corresponding to the natural subunit, such as being able to perform the activity of the annexin protein in preventing thrombus formation.

Annexin protein and modified annexin homologues can be the result of natural allelic variation or natural mutation. The protein homologues of the present invention can also be produced using techniques known in the art, including, but not limited to, direct modifications to the protein or modifications to the gene encoding the protein using, for example, classic or recombinant DNA techniques to effect random or targeted mutagenesis.

Also included is a modified annexin protein containing an amino acid sequence that is at least about 75%, more preferably at least about 80%, more preferably at least about 85%, more preferably at least about 90%, more preferably at least about 95%, and most preferably at least about 98% identical to amino acid sequence SEQ ID NO:3, SEQ ID NO:6, SEQ ID NO:12, SEQ ID NO:15, SEQ ID NO:19, SEQ ID NO:23 or a protein encoded by an allelic variant of a nucleic acid molecule encoding a protein containing any of these sequences. Also included is a modified annexin protein comprising more than one of SEQ ID NO:3, SEQ ID NO:6, SEQ ID NO:12, SEQ ID NO:15; SEQ ID NO:19, or SEQ ID NO:23; for example, a protein comprising SEQ ID NO:3 and SEQ ID NO:12 and separated by a linker. Methods to determine percent identities between amino acid sequences and between nucleic acid sequences are known to those skilled in the art. Methods to determine percent identities between sequences include computer programs such as the GCG® Wisconsin package™ (available from Accelrys Corporation), the DNAsis™ program (available from Hitachi Software, San Bruno, Calif.), the Vector NTI Suite (available from Informax, Inc., North Bethesda, Md.), or the BLAST software available on the NCBI website.

In one embodiment, a modified annexin protein includes an amino acid sequence of at least about 5 amino acids, preferably at least about 50 amino acids, more preferably at least about 100 amino acids, more preferably at least about 200 amino acids, more preferably at least about 250 amino acids, more preferably at least about 275 amino acids, more preferably at least about 300 amino acids, and most preferably at least about 319 amino acids or the full-length annexin protein, whichever is shorter. In another embodiment, annexin proteins contain full-length proteins, i.e., proteins encoded by full-length coding regions, or post-translationally modified proteins thereof, such as mature proteins from which initiating methionine and/or signal sequences or "pro" sequences have been removed.

A fragment of a modified annexin protein of the present invention preferably contains at least about 5 amino acids, more preferably at least about 10 amino acids, more preferably at least about 15 amino acids, more preferably at least about 20 amino acids, more preferably at least about 25 amino acids, more preferably at least about 30 amino acids, more preferably at least about 35 amino acids, more preferably at least about 40 amino acids, more preferably at least about 45 amino acids, more preferably at least about 50 amino acids, more preferably at least about 55 amino acids, more preferably at least about 60 amino acids, more preferably at least about 65 amino acids, more preferably at least about 70 amino acids, more preferably at least about 75 amino acids, more preferably at least about 80 amino acids, more preferably at least about 85 amino acids, more preferably at least about 90 amino acids, more preferably at least about 95 amino acids, and even more preferably at least about 100 amino acids in length.

In one embodiment, an isolated modified annexin protein of the present invention contains a protein encoded by a nucleic acid molecule having the nucleic acid sequence SEQ ID NO:4, SEQ ID NO:17 or SEQ ID NO:21. Alternatively, the modified annexin protein contains a protein encoded by a nucleic acid molecule having the nucleic acid sequence SEQ ID NO:1 or by an allelic variant of a nucleic acid molecule having one of these sequences. Alternatively, the modified annexin protein contains more than one protein sequence encoded by a nucleic acid molecule having the nucleic acid sequence SEQ ID NO:1, SEQ ID NO:10, SEQ ID NO:13 or by an allelic variant of a nucleic acid molecule having this sequence.

In one embodiment, an isolated modified annexin protein of the present invention contains a protein encoded by a nucleic acid molecule having the nucleic acid sequence SEQ ID NO:10 or by an allelic variant of a nucleic acid molecule having this sequence. Alternatively, the modified annexin protein contains more than one protein sequence encoded by a nucleic acid molecule having the nucleic acid sequence SEQ ID NO:10 or by an allelic variant of a nucleic acid molecule having this sequence (e.g., SEQ ID NO: 12-linker-SEQ ID NO: 12; SEQ ID NO:19).

In another embodiment, an isolated modified annexin protein of the present invention is a modified protein encoded by a nucleic acid molecule having the nucleic acid sequence SEQ ID NO:13 or by an allelic variant of a nucleic acid molecule having this sequence. Alternatively, the modified annexin protein contains more than one protein sequence encoded by a nucleic acid molecule having the nucleic acid sequence SEQ ID NO:13 or by an allelic variant of a nucleic acid molecule having this sequence (e.g., SEQ ID NO: 15-linker-SEQ ID NO: 15; SEQ ID NO:23).

In another embodiment, an isolated modified annexin protein of the present invention is a modified protein which contains a protein encoded by a nucleic acid molecule having the nucleic acid sequence SEQ ID NO:1 and a protein encoded by a nucleic acid molecule having the nucleic acid sequence SEQ ID NO:10, or by allelic variants of these nucleic acid molecules (e.g., SEQ ID NO: 3-linker-SEQ ID NO:12 or SEQ ID NO:12-linker-SEQ ID NO:3).

In another embodiment, an isolated modified annexin protein of the present invention is a modified protein which contains a protein encoded by a nucleic acid molecule having the nucleic acid sequence SEQ ID NO:1 and a protein encoded by a nucleic acid molecule having the nucleic acid sequence SEQ ID NO:13, or by allelic variants of these nucleic acid molecules (e.g., SEQ ID NO:3-linker-SEQ ID NO:15 or SEQ ID NO:15-linker-SEQ ID NO:3).

In another embodiment, an isolated modified annexin protein of the present invention is a modified protein which contains a protein encoded by a nucleic acid molecule having the nucleic acid sequence SEQ ID NO:10 and a protein encoded by a nucleic acid molecule having the nucleic acid sequence SEQ ID NO:13, or by allelic variants of these nucleic acid molecules (e.g., SEQ ID NO:12-linker-SEQ ID NO:15 or SEQ ID NO:15-linker-SEQ ID NO:12).

One embodiment of the present invention includes a non-native modified annexin protein encoded by a nucleic acid molecule that hybridizes under stringent hybridization conditions with an annexin gene. As used herein, stringent hybridization conditions refer to standard hybridization conditions under which nucleic acid molecules, including oligonucleotides, are used to identify molecules having similar nucleic acid sequences. Such standard conditions are disclosed, for example, in Sambrook et al., *Molecular Cloning: A Laboratory Manual, Cold Spring Harbor Labs Press* (1989), incorporated herein by reference. Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., *Anal. Biochem.* 138:267-284 (1984), incorporated herein by reference. In some embodiments, hybridization conditions will permit isolation of nucleic acid molecules having at least about 80% nucleic acid sequence identity with the nucleic acid molecule being used to probe. In other embodiments, hybridization conditions will permit isolation of nucleic acid molecules having at least about 90% nucleic acid sequence identity with the nucleic acid molecule being used to probe. In still other embodiments, hybridization conditions will permit isolation of nucleic acid molecules having at least about 95% nucleic acid sequence identity with the nucleic acid molecule being used to probe.

A modified annexin protein includes a protein encoded by a nucleic acid molecule that is at least about 50 nucleotides and that hybridizes under conditions that preferably allow about 20% base pair mismatch, more preferably under conditions that allow about 15% base pair mismatch, more preferably under conditions that allow about 10% base pair mismatch, more preferably under conditions that allow about 5% base pair mismatch, and even more preferably under conditions that allow about 2% base pair mismatch with a nucleic acid molecule selected from the group consisting of SEQ ID NO:1, SEQ ID NO:4, SEQ ID NO:10, SEQ ID NO:13, SEQ ID NO:17, SEQ ID NO:21, or a complement of any of these nucleic acid molecules.

As used herein, an annexin gene includes all nucleic acid sequences related to a natural annexin gene such as regulatory regions that control production of the annexin protein encoded by that gene (such as, but not limited to, transcription, translation or post-translation control regions) as well as the coding region itself. In one embodiment, an annexin gene includes the nucleic acid sequence SEQ ID NO:1. In another embodiment, an annexin gene includes the nucleic acid sequence SEQ ID NO:10. In another embodiment, an annexin gene includes the nucleic acid sequence SEQ ID NO:13. In another embodiment, an annexin gene includes the nucleic acid sequence SEQ ID NO:17. In another embodiment, an annexin gene includes the nucleic acid sequence SEQ ID NO:21. It should be noted that since nucleic acid sequencing technology is not entirely error-free, SEQ ID NO:1 (as well as other sequences presented herein), at best, represents an apparent nucleic acid sequence of the nucleic acid molecule encoding an annexin protein of the present invention.

In another embodiment, an annexin gene can be an allelic variant that includes a similar but not identical sequence to SEQ ID NO:1. In another embodiment, an annexin gene can be an allelic variant that includes a similar but not identical sequence to SEQ ID NO:10. In another embodiment, an annexin gene can be an allelic variant that includes a similar but not identical sequence to SEQ ID NO:13. In another embodiment, an annexin gene can be an allelic variant that includes a similar but not identical sequence to SEQ ID NO:17. In another embodiment, an annexin gene can be an allelic variant that includes a similar but not identical sequence to SEQ ID NO:21. An allelic variant of an annexin gene including SEQ ID NO:1 is a gene that occurs at essentially the same locus (or loci) in the genome as the gene including SEQ ID NO:1, but which, due to natural variations caused by, for example, mutation or recombination, has a similar but not identical sequence. Allelic variants typically encode proteins having similar activity to that of the protein encoded by the gene to which they are being compared. Allelic variants can also comprise alterations in the 5' or 3' untranslated regions of the gene (e.g., in regulatory control regions). Allelic variants are well known to those skilled in the art and would be expected to be found within a given human since the genome is diploid and/or among a population comprising two or more humans.

An isolated modified annexin protein of the present invention can be obtained from its natural source, can be produced using recombinant DNA technology, or can be produced by chemical synthesis. As used herein, an isolated modified annexin protein can contain a full-length protein or any homologue of such a protein. Examples of annexin and modified annexin homologues include annexin and modified annexin proteins in which amino acids have been deleted (e.g., a truncated version of the protein, such as a peptide or by a protein splicing reaction when an intron has been removed or two exons are joined), inserted, inverted, substituted and/or derivatized (e.g., by glycosylation, phosphorylation, acetylation, methylation, myristylation, prenylation, palmitoylation, amidation and/or addition of glycerophosphatidyl inositol) such that the homologue includes at least one epitope capable of eliciting an immune response against an annexin protein. That is, when the homologue is administered to an animal as an immunogen, using techniques known to those skilled in the art, the animal will produce a humoral and/or cellular immune response against at least one epitope of an annexin protein. Annexin and modified annexin homologues can also be selected by their ability to selectively bind to immune serum. Methods to measure such activities are disclosed herein. Annexin and modified annexin homologues also include those proteins that are capable of performing the function of native annexin in a functional assay; that is, are capable of binding to phosphatidylserine or to activated platelets or exhibiting antithrombotic activity. Methods for such assays are described in the Examples section and elsewhere herein.

A modified annexin protein of the present invention may be identified by its ability to perform the function of an annexin protein in a functional assay. The phrase "capable of performing the function of that in a functional assay" means that the protein or modified protein has at least about 10% of the activity of the natural protein in the functional assay. In other embodiments, it has at least about 20% of the activity of the natural protein in the functional assay. In other embodiments, it has at least about 30% of the activity of the natural protein in the functional assay. In other embodiments, it has at least about 40% of the activity of the natural protein in the functional assay. In other embodiments, it has at least about 50% of the activity of the natural protein in the functional assay. In other embodiments, the protein or modified protein has at least about 60% of the activity of the natural protein in the functional assay. In still other embodiments, the protein or modified protein has at least about 70% of the activity of the natural protein in the functional assay. In yet other embodiments, the protein or modified protein has at least about 80% of the activity of the natural protein in the functional assay. In other embodiments, the protein or modified protein has at least about 90% of the activity of the natural protein in the functional assay. Examples of functional assays are described herein.

An isolated protein of the present invention can be produced in a variety of ways, including recovering such a protein from a bacterium and producing such a protein recombinantly. One embodiment of the present invention is a method to produce an isolated modified annexin protein of the present invention using recombinant DNA technology. Such a method includes the steps of (a) culturing a recombinant cell containing a nucleic acid molecule encoding a modified annexin protein of the present invention to produce the protein and (b) recovering the protein therefrom. Details on producing recombinant cells and culturing thereof are presented below. The phrase "recovering the protein" refers simply to collecting the whole fermentation medium containing the protein and need not imply additional steps of separation or purification. Proteins of the present invention can be purified using a variety of standard protein purification techniques.

Isolated proteins of the present invention are preferably retrieved in "substantially pure" form. As used herein, "substantially pure" refers to a purity that allows for the effective use of the protein in a functional assay.

Modified Annexin Nucleic Acid Molecules or Genes

Another embodiment of the present invention is an isolated nucleic acid molecule capable of hybridizing under stringent conditions with a gene encoding a modified annexin protein such as a homodimer of annexin V, a homodimer of annexin IV, a homodimer of annexin VIII, a heterodimer of annexin V and annexin VIII, a heterodimer of annexin V and annexin IV or a heterodimer of annexin IV and annexin VIII. Such a nucleic acid molecule is also referred to herein as a modified annexin nucleic acid molecule. Included is an isolated nucleic acid molecule that hybridizes under stringent conditions with a modified annexin gene. The characteristics of such genes are disclosed herein. In accordance with the present invention, an isolated nucleic acid molecule is a nucleic acid molecule that has been removed from its natural milieu (i.e., that has been subject to human manipulation). As such, "isolated" does not reflect the extent to which the nucleic acid molecule has been purified. An isolated nucleic acid molecule can include DNA, RNA, or derivatives of either DNA or RNA.

As stated above, a modified annexin gene includes all nucleic acid sequences related to a natural annexin gene, such as regulatory regions that control production of an annexin protein encoded by that gene (such as, but not limited to, transcriptional, translational, or post-translational control regions) as well as the coding region itself. A nucleic acid molecule of the present invention can be an isolated modified annexin nucleic acid molecule or a homologue thereof. A nucleic acid molecule of the present invention can include one or more regulatory regions, full-length or partial coding regions, or combinations thereof. The minimal size of a modified annexin nucleic acid molecule of the present invention is the minimal size capable of forming a stable hybrid under stringent hybridization conditions with a corresponding natural gene. Annexin nucleic acid molecules can also include a nucleic acid molecule encoding a hybrid protein, a fusion protein, a multivalent protein or a truncation fragment.

An isolated nucleic acid molecule of the present invention can be obtained from its natural source either as an entire (i.e., complete) gene or a portion thereof capable of forming a stable hybrid with that gene. As used herein, the phrase "at least a portion of" an entity refers to an amount of the entity that is at least sufficient to have the functional aspects of that entity. For example, at least a portion of a nucleic acid sequence, as used herein, is an amount of a nucleic acid sequence capable of forming a stable hybrid with the corresponding gene under stringent hybridization conditions.

An isolated nucleic acid molecule of the present invention can also be produced using recombinant DNA technology (e.g., polymerase chain reaction (PCR) amplification, cloning, etc.) or chemical synthesis. Isolated modified annexin nucleic acid molecules include natural nucleic acid molecules and homologues thereof, including, but not limited to, natural allelic variants and modified nucleic acid molecules in which nucleotides have been inserted, deleted, substituted, and/or inverted in such a manner that such modifications do not substantially interfere with the ability of the nucleic acid molecule to encode an annexin protein of the present invention or to form stable hybrids under stringent conditions with natural nucleic acid molecule isolates.

A modified annexin nucleic acid molecule homologue can be produced using a number of methods known to those skilled in the art (see, e.g., Sambrook et al., 1989). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures, and ligation of mixture groups to "build" a mixture of nucleic acid molecules and combinations thereof. Nucleic acid molecule homologues can be selected from a mixture of modified nucleic acids by screening for the function of the protein encoded by the nucleic acid (e.g., the ability of a homologue to elicit an immune response against an annexin protein and/ or to function in a clotting assay, or other functional assay), and/or by hybridization with isolated annexin-encoding nucleic acids under stringent conditions.

An isolated modified annexin nucleic acid molecule of the present invention can include a nucleic acid sequence that encodes at least one modified annexin protein of the present invention, examples of such proteins being disclosed herein. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a modified annexin protein.

One embodiment of the present invention is a modified annexin nucleic acid molecule that is capable of hybridizing under stringent conditions to a nucleic acid strand that encodes at least a portion of a modified annexin protein or a homologue thereof or to the complement of such a nucleic acid strand. A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand, that is represented by a SEQ ID NO, also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art. Included is a modified annexin nucleic acid molecule that includes a nucleic acid sequence having at least about 65 percent, preferably at least about 70 percent, more preferably at least about 75 percent, more preferably at least about 80 percent, more preferably at least about 85 percent, more preferably at least about 90 percent and even more preferably at least about 95 percent homology with the corresponding region(s) of the nucleic acid sequence encoding at least a portion of a modified annexin protein. Included is a modified annexin nucleic acid molecule capable of encoding a homodimer of an annexin protein or homologue thereof.

Annexin nucleic acid molecules include SEQ ID NO:4 and allelic variants of SEQ ID NO:4, SEQ ID NO:1 and an allelic variants of SEQ ID NO:1, SEQ ID NO:10 and an allelic variants of SEQ ID NO:10; SEQ ID NO:13 and an allelic variants of SEQ ID NO:13; SEQ ID NO:17 and an allelic variants of SEQ ID NO:17; and SEQ ID NO:21 and an allelic variants of SEQ ID NO:21.

Knowing a nucleic acid molecule of a modified annexin protein of the present invention allows one skilled in the art to make copies of that nucleic acid molecule as well as to obtain a nucleic acid molecule including additional portions of annexin protein-encoding genes (e.g., nucleic acid molecules that include the translation start site and/or transcription and/ or translation control regions), and/or annexin nucleic acid molecule homologues. Knowing a portion of an amino acid sequence of an annexin protein of the present invention allows one skilled in the art to clone nucleic acid sequences encoding such an annexin protein. In addition, a desired modified annexin nucleic acid molecule can be obtained in a variety of ways including screening appropriate expression libraries with antibodies that bind to annexin proteins of the present invention; traditional cloning techniques using oligonucleotide probes of the present invention to screen appropriate libraries or DNA; and PCR amplification of appropriate libraries, or RNA or DNA using oligonucleotide primers of the present invention (genomic and/or cDNA libraries can be used).

The present invention also includes nucleic acid molecules that are oligonucleotides capable of hybridizing, under stringent conditions, with complementary regions of other, preferably longer, nucleic acid molecules of the present invention that encode at least a portion of a modified annexin protein. Oligonucleotides of the present invention can be RNA, DNA, or derivatives of either. The minimal size of such oligonucleotides is the size required to form a stable hybrid between a given oligonucleotide and the complementary sequence on another nucleic acid molecule of the present invention. Minimal size characteristics are disclosed herein. The size of the oligonucleotide must also be sufficient for the use of the oligonucleotide in accordance with the present invention. Oligonucleotides of the present invention can be used in a variety of applications including, but not limited to, as probes to identify additional nucleic acid molecules, as primers to amplify or extend nucleic acid molecules or in therapeutic applications to modulate modified annexin production. Such therapeutic applications include the use of such oligonucleotides in, for example, antisense-, triplex formation-, ribozyme- and/or RNA drug-based technologies. The present invention, therefore, includes such oligonucleotides and methods to modulate the production of modified annexin proteins by use of one or more of such technologies.

Natural, Wild-Type Bacterial Cells and Recombinant Molecules and Cells

The present invention also includes a recombinant vector, which includes a modified annexin nucleic acid molecule of the present invention inserted into any vector capable of delivering the nucleic acid molecule into a host cell. Such a vector contains heterologous nucleic acid sequences, that is, nucleic acid sequences that are not naturally found adjacent to modified annexin nucleic acid molecules of the present invention. The vector can be either RNA or DNA, either prokaryotic or eukaryotic, and typically is a virus or a plasmid. Recombinant vectors can be used in the cloning, sequencing, and/or otherwise manipulating of modified annexin nucleic acid molecules of the present invention. One type of recombinant vector, herein referred to as a recombinant molecule and described in more detail below, can be used in the expression of nucleic acid molecules of the present invention. Some recombinant vectors are capable of replicating in the transformed cell. Nucleic acid molecules to include in recombinant vectors of the present invention are disclosed herein.

As heretofore disclosed, one embodiment of the present invention is a method to produce a modified annexin protein of the present invention by culturing a cell capable of expressing the protein under conditions effective to produce the protein, and recovering the protein. In an alternative embodiment, the method includes producing an annexin protein by culturing a cell capable of expressing the protein under conditions effective to produce the annexin protein, recovering the protein, and modifying the protein by coupling it to an agent that increases its effective size.

In one embodiment, the cell to culture is a natural bacterial cell, and modified annexin is isolated from these cells. In another embodiment, a cell to culture is a recombinant cell that is capable of expressing the modified annexin protein, the recombinant cell being produced by transforming a host cell with one or more nucleic acid molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Nucleic acid molecules with which to transform a host cell are disclosed herein.

Suitable host cells to transform include any cell that can be transformed and that can express the introduced modified annexin protein. Such cells are, therefore, capable of producing modified annexin proteins of the present invention after being transformed with at least one nucleic acid molecule of the present invention. Host cells can be either untransformed cells or cells that are already transformed with at least one nucleic acid molecule. Suitable host cells of the present invention can include bacterial, fungal (including yeast), insect, animal, and plant cells. Host cells include bacterial cells, with *E. Coli* cells being particularly preferred. Alternative host cells are untransformed (wild-type) bacterial cells producing cognate modified annexin proteins, including attenuated strains with reduced pathogenicity, as appropriate.

A recombinant cell is preferably produced by transforming a host cell with one or more recombinant molecules, each comprising one or more nucleic acid molecules of the present invention operatively linked to an expression vector containing one or more transcription control sequences. The phrase "operatively linked" refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, insect, animal, and/or plant cells. As such, nucleic acid molecules of the present invention can be operatively linked to expression vectors containing regulatory sequences such as promoters, operators, repressors, enhancers, termination sequences, origins of replication, and other regulatory sequences that are compatible with the recombinant cell and that control the expression of nucleic acid molecules of the present invention. As used herein, a transcription control sequence includes a sequence that is capable of controlling the initiation, elongation, and termination of transcription. Particularly important transcription control sequences are those that control transcription initiation, such as promoter, enhancer, operator and repressor sequences. Suitable transcription control sequences include any transcription control sequence that can function in at least one of the recombinant cells of the present invention. A variety of such transcription control sequences are known to the art. Transcription control sequences include those which function in bacterial, yeast, insect and mammalian cells, such as, but not limited to, tac, lac, tzp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SP01, metallothionein, alpha mating factor, *Pichia* alcohol oxidase, alphavirus subgenomic promoters (such as Sindbis virus subgenomic promoters), baculovirus, Heliothis zea insect virus, vaccinia virus, herpesvirus, poxvirus, adenovirus, simian virus 40, retrovirus actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins). Transcription control sequences of the present invention can also include naturally occurring transcription control sequences naturally associated with a DNA sequence encoding an annexin protein. One transcription control sequence is the Kozak strong promotor and initiation sequence.

Expression vectors of the present invention may also contain secretory signals (i.e., signal segment nucleic acid sequences) to enable an expressed annexin protein to be secreted from the cell that produces the protein. Suitable signal segments include an annexin protein signal segment or any heterologous signal segment capable of directing the secretion of an annexin protein, including fusion proteins, of the present invention. Signal segments include, but are not limited to, tissue plasminogen activator (t-PA), interferon, interleukin, growth hormone, histocompatibility and viral envelope glycoprotein signal segments.

Expression vectors of the present invention may also contain fusion sequences which lead to the expression of inserted nucleic acid molecules of the present invention as fusion proteins. Inclusion of a fusion sequence as part of a modified annexin nucleic acid molecule of the present invention can enhance the stability during production, storage and/or use of the protein encoded by the nucleic acid molecule. Furthermore, a fusion segment can function as a tool to simplify purification of a modified annexin protein, such as to enable purification of the resultant fusion protein using affinity chromatography. One fusion segment that can be used for protein purification is the 8-amino acid peptide sequence asp-tyr-lys-asp-asp-asp-asp-lys (SEQ ID NO:9).

A suitable fusion segment can be a domain of any size that has the desired function (e.g., increased stability and/or purification tool). It is within the scope of the present invention to use one or more fusion segments. Fusion segments can be joined to amino and/or carboxyl termini of an annexin protein. Another type of fusion protein is a fusion protein wherein the fusion segment connects two or more annexin proteins or modified annexin proteins. Linkages between fusion segments and annexin proteins can be constructed to be susceptible to cleavage to enable straightforward recovery of the annexin or modified annexin proteins. Fusion proteins are preferably produced by culturing a recombinant cell transformed with a fusion nucleic acid sequence that encodes a protein including the fusion segment attached to either the carboxyl and/or amino terminal end of an annexin protein.

A recombinant molecule of the present invention is a molecule that can include at least one of any nucleic acid molecule heretofore described operatively linked to at least one of any transcription control sequence capable of effectively regulating expression of the nucleic acid molecules in the cell to be transformed. A recombinant molecule includes one or more nucleic acid molecules of the present invention, including those that encode one or more modified annexin proteins. Recombinant molecules of the present invention and their production are described in the Examples section. Similarly, a recombinant cell includes one or more nucleic acid molecules of the present invention, with those that encode one or more annexin proteins. Recombinant cells of the present invention include those disclosed in the Examples section.

It may be appreciated by one skilled in the art that use of recombinant DNA technologies can improve expression of transformed nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, deletion of sequences that destabilize transcripts, and use of control signals that temporally separate recombinant cell growth from recombinant protein production during fermentation. The activity of an expressed recombinant protein of the present invention may be improved by fragmenting, modifying, or derivatizing the resultant protein.

In accordance with the present invention, recombinant cells can be used to produce annexin or modified annexin proteins of the present invention by culturing such cells under conditions effective to produce such a protein, and recovering the protein. Effective conditions to produce a protein include, but are not limited to, appropriate media, bioreactor, temperature, pH and oxygen conditions that permit protein production. An appropriate, or effective, medium refers to any medium in which a cell of the present invention, when cultured, is capable of producing an annexin or modified annexin protein. Such a medium is typically an aqueous medium comprising assimilable carbohydrate, nitrogen and phosphate sources, as well as appropriate salts, minerals, metals and other nutrients, such as vitamins. The medium may comprise complex, nutrients or may be a defined minimal medium.

Cells of the present invention can be cultured in conventional fermentation bioreactors, which include, but are not limited to, batch, fed-batch, cell recycle, and continuous fermentors. Culturing can also be conducted in shake flasks, test tubes, microtiter dishes, and petri plates. Culturing is carried out at a temperature, pH and oxygen content appropriate for the recombinant cell. Such culturing conditions are well within the expertise of one of ordinary skill in the art.

Depending on the vector and host system used for production, resultant annexin proteins may either remain within the recombinant cell; be secreted into the fermentation medium; be secreted into a space between two cellular membranes, such as the periplasmic space in *E. coli*; or be retained on the outer surface of a cell or viral membrane. Methods to purify such proteins are disclosed in the Examples section.

Antibodies

The present invention also includes isolated anti-modified annexin antibodies and their use. An anti-modified annexin antibody is an antibody capable of selectively binding to a modified annexin protein. Isolated antibodies are antibodies that have been removed from their natural milieu. The term "isolated" does not refer to the state of purity of such antibodies. As such, isolated antibodies can include anti-sera containing such antibodies, or antibodies that have been purified to varying degrees. As used herein, the term "selectively binds to" refers to the ability of such antibodies to preferentially bind to the protein against which the antibody was raised (i.e., to be able to distinguish that protein from unrelated components in a mixture). Binding affinities, commonly expressed as equilibrium association constants, typically range from about $10^3$ $M^{-1}$ to about $10^{12}$ $M^{-1}$. Binding can be measured using a variety of methods known to those skilled in the art including immunoblot assays, immunoprecipitation assays, radioimmunoassays, enzyme immunoassays (e.g., ELISA), immunofluorescent antibody assays and immuno-electron microscopy; see, e.g., Sambrook et al., 1989.

Antibodies of the present invention can be either polyclonal or monoclonal antibodies. Antibodies of the present invention include functional equivalents such as antibody fragments and genetically-engineered antibodies, including single chain antibodies, that are capable of selectively binding to at least one of the epitopes of the protein used to obtain the antibodies. Antibodies of the present invention also include chimeric antibodies that can bind to more than one epitope. Antibodies are raised in response to proteins that are encoded, at least in part, by a modified annexin nucleic acid molecule of the present invention.

Anti-modified annexin antibodies of the present invention include antibodies raised in an animal administered a modified annexin. Anti-modified annexin antibodies of the present invention also include antibodies raised in an animal against one or more modified annexin proteins of the present invention that are then recovered from the cell using techniques known to those skilled in the art. Yet additional antibodies of the present invention are produced recombinantly using techniques as heretofore disclosed for modified annexin proteins of the present invention. Antibodies produced against defined proteins can be advantageous because such antibodies are not substantially contaminated with antibodies against other substances that might otherwise cause interference in a diagnostic assay or side effects if used in a therapeutic composition.

Anti-modified annexin antibodies of the present invention have a variety of uses that are within the scope of the present invention. Anti-modified annexin antibodies can be used as tools to screen expression libraries and/or to recover desired proteins of the present invention from a mixture of proteins and other contaminants.

An anti-modified annexin antibody of the present invention can selectively bind to a modified annexin protein.

Therapeutic Methods

Any of the above-described modified annexin proteins is used in methods of the invention to treat arterial or venous thrombosis caused by any medical procedure or condition. Generally, the therapeutic agents used in the invention are administered to an animal in an effective amount. Generally, an effective amount is an amount effective either (1) to reduce the symptoms of the disease sought to be treated or (2) to induce a pharmacological change relevant to treating the disease sought to be treated.

For thrombosis, an effective amount includes an amount effective to exert prolonged antithrombotic activity without substantially increasing the risk of hemorrhage or to increase the life expectancy of the affected animal. As used herein, prolonged antithrombotic activity refers to the time of activity of the modified annexin protein with respect to the time of activity of the same amount (molar) of an unmodified annexin protein. Preferably, antithrombotic activity is prolonged by at least about a factor of two, more preferably by at least about a factor of five, and most preferably by at least about a factor of ten. Preferably, the effective amount does not substantially increase the risk of hemorrhage compared with the hemorrhage risk of the same subject to whom the modified annexin has not been administered. Preferably, the hemorrhage risk is very small and, at most, below that provided by alternative antithrombotic treatments available in the prior art. Therapeutically effective amounts of the therapeutic agents can be any amount or dose sufficient to bring about the desired antithrombotic effect and depends, in part, on the condition, type, and location of the thrombus, the size and condition of the patient, as well as other factors known to those skilled in the art. The dosages can be given as a single dose, or as several doses, for example, divided over the course of several weeks.

Administration preferably occurs by bolus injection or by intravenous infusion, either after thrombosis to prevent further thrombosis or under conditions in which the subject is susceptible to or at risk of thrombosis.

The therapeutic agents of the present invention can be administered by any suitable means, including, for example, parenteral or local administration, such as intravenous or subcutaneous injection, or by aerosol. A therapeutic composition can be administered in a variety of unit dosage forms depending upon the method of administration. Delivery methods for a therapeutic composition of the present invention include intravenous administration and local administration by, for example, injection. For particular modes of delivery, a therapeutic composition of the present invention can be formulated in an excipient of the present invention. A therapeutic agent of the present invention can be administered to any animal, preferably to mammals, and more preferably to humans.

One suitable administration time occurs following coronary thrombosis, thereby preventing the recurrence of thrombosis without substantially increasing the risk of hemorrhage. Bolus injection of the modified annexin is preferably performed soon after thrombosis, e.g., before admission to hospital. The modified annexin can be administered in conjunction with a thrombolytic therapeutic such as tissue plasminogen activator, urokinase, or a bacterial enzyme.

Methods of use of modified annexin proteins of the present invention include methods to treat cerebral thrombosis, including overt cerebral thrombosis or transient cerebral ischemic attacks, by administering an effective amount of modified annexin protein to a patient in need thereof. Transient cerebral ischemic attacks frequently precede full-blown strokes. The modified annexin can also be administered to diabetic and other patients who are at increased risk for thrombosis in peripheral arteries. Accordingly, the present invention provides a method for reducing the risk of thrombosis in a patient having an increased risk for thrombosis including administering an effective amount of a modified annexin protein to a patient in need thereof. For an adult patient, the modified annexin can be administered intravenously or as a bolus in the dosage range of about 1 to about 100 mg.

The present invention also provides a method for decreasing the risk of venous thrombosis associated with some surgical procedures, such as hip and knee arthroplasties, by administering an effective amount of a modified annexin protein of the present invention to a patient in need thereof. The modified annexin treatment can prevent thrombosis without increasing hemorrhage into the operating field. In another embodiment, the present invention provides a method for preventing thrombosis associated with pregnancy and parturition without increasing hemorrhage, by administering an effective amount of a modified annexin protein of the present invention to a patient in need thereof. In a further embodiment, the present invention provides a method for the treatment of recurrent venous thrombosis, by administering an effective amount of a modified annexin protein of the present invention to a patient in need thereof. For an adult patient, the modified annexin can be administered intravenously as a bolus in the dosage range of about 1 to about 100 mg.

The present invention also provides a method of screening for a modified annexin protein that modulates thrombosis, by contacting a thrombosis test system with at least one test modified annexin protein under conditions permissive for thrombosis, and comparing the antithrombotic activity in the presence of the test modified annexin protein with the antithrombotic activity in the absence of the test modified annexin protein, wherein a change in the antithrombotic activity in the presence of the test modified annexin protein is indicative of a modified annexin protein that modulates thrombotic activity. In one embodiment, the thrombosis test system is a system for measuring activated partial thromboplastin time. Also included within the scope of the present invention are modified annexin proteins that modulate thrombosis as identified by this method.

The present invention also provides a method for identifying a modified annexin protein for annexin activity, including contacting activated platelets with at least one test modified annexin protein under conditions permissive for binding, and comparing the test modified annexin-binding activity and protein S-binding activity of the platelets in the presence of the test modified annexin protein with the annexin-binding activity and protein S-binding activity in the presence of unmodified annexin protein, whereby a modified annexin protein with annexin activity may be identified. Also included within the scope of the invention are modified annexin proteins identified by the method.

In an additional embodiment, the present invention provides a method of screening for a modified annexin protein that modulates thrombosis, by contacting an in vivo thrombosis test system with at least one test modified annexin protein under conditions permissive for thrombosis, and comparing the antithrombotic activity in the presence of the test modified annexin protein with the antithrombotic activity in the absence of the test modified annexin protein. A change in the antithrombotic activity in the presence of the test modified annexin protein is indicative of a modified annexin protein that modulates thrombotic activity. Additionally, the time over which antithrombotic activity is sustained in the presence of the test modified annexin protein is compared with a time of antithrombotic activity in the presence of unmodified annexin to determine the prolongation of antithrombotic activity associated with the test modified annexin protein. The extent of hemorrhage in the presence of the test modified annexin protein is assessed, e.g., by measuring tail bleeding time, and compared with the extent of hemorrhage in the absence of the test modified annexin protein. In one embodiment, the in vivo thrombosis test system is a mouse model of photochemically-induced thrombus in cremaster muscles. Also included within the scope of the present invention are modified annexin proteins that modulate thrombosis as identified by this method.

In a further embodiment, the therapeutic agents of the present invention are useful for gene therapy. As used herein, the phrase "gene therapy" refers to the transfer of genetic material (e.g., DNA or RNA) of interest into a host to treat or prevent a genetic or acquired disease or condition. The genetic material of interest encodes a product (e.g., a protein polypeptide, peptide or functional RNA) whose production in vivo is desired. For example, the genetic material of interest can encode a hormone, receptor, enzyme or (poly)peptide of therapeutic value. In a specific embodiment, the subject invention utilizes a class of lipid molecules for use in non-viral gene therapy which can complex with nucleic acids as described in Hughes et al., U.S. Pat. No. 6,169,078, incorporated herein by reference, in which a disulfide linker is provided between a polar head group and a lipophilic tail group of a lipid.

These therapeutic compounds of the present invention effectively complex with DNA and facilitate the transfer of DNA through a cell membrane into the intracellular space of a cell to be transformed with heterologous DNA. Furthermore, these lipid molecules facilitate the release of heterologous DNA in the cell cytoplasm thereby increasing gene transfection during gene therapy in a human or animal.

Cationic lipid-polyanionic macromolecule aggregates may be formed by a variety of methods known in the art. Representative methods are disclosed by Felgner et al., *Proc. Natl. Acad. Sci. USA* 86: 7413-7417 (1987); Eppstein et al., U.S. Pat. No. 4,897,355; Behr et al., *Proc. Natl. Acad. Sci. USA* 86:6982-6986 (1989); Bangham et al., *J. Mol. Biol.* 23:238-252 (1965); Olson et al., *Biochim. Biophys. Acta* 557:9 (1979); Szoka, et al., *Proc. Natl. Acad. Sci.* 75:4194 (1978); Mayhew et al., *Biochim. Biophys. Acta* 775:169 (1984); Kim et al., *Biochim. Biophys. Acta* 728:339 (1983); and Fukunaga et al., *Endocrinol.* 115:757 (1984), all incorporated herein by reference. In general, aggregates may be formed by preparing lipid particles consisting of either (1) a cationic lipid or (2) a cationic lipid mixed with a colipid, followed by adding a polyanionic macromolecule to the lipid particles at about room temperature (about 18 to 26° C.). In general, conditions are chosen that are not conducive to deprotection of protected groups. In one embodiment, the mixture is then allowed to form an aggregate over a period of about 10 minutes to about 20 hours, with about 15 to 60 minutes most conveniently used. Other time periods may be appropriate for specific lipid types. The complexes may be formed over a longer period, but additional enhancement of transfection efficiency will not usually be gained by a longer period of complexing.

The compounds and methods of the subject invention can be used to intracellularly deliver a desired molecule, such as, for example, a polynucleotide, to a target cell. The desired polynucleotide can be composed of DNA or RNA or analogs thereof. The desired polynucleotides delivered using the present invention can be composed of nucleotide sequences that provide different functions or activities, such as nucleotides that have a regulatory function, e.g., promoter sequences, or that encode a polypeptide. The desired polynucleotide can also provide nucleotide sequences that are antisense to other nucleotide sequences in the cell. For example, the desired polynucleotide when transcribed in the cell can provide a polynucleotide that has a sequence that is antisense to other nucleotide sequences in the cell. The antisense sequences can hybridize to the sense strand sequences in the cell. Polynucleotides that provide antisense sequences can be readily prepared by the ordinarily skilled artisan. The desired polynucleotide delivered into the cell can also comprise a nucleotide sequence that is capable of forming a triplex complex with double-stranded DNA in the cell.

The present invention provides compounds and methods for preventing or attenuating reperfusion injury in mammals. Reperfusion injury (RI) occurs when the blood supply to an organ or tissue is cut off and after an interval restored. The loss of phospholipid asymmetry in endothelial cells and other cells is considered a significant event in the pathogenesis of RI. The PS exposed on the surfaces of these cells allows the binding of activated monocytes. This binding triggers a sequence of events leading to irreversible apoptosis of endothelial and other cells, another significant event in RI. In addition, PS on the surfaces of cells, and vesicles derived therefrom, is accessible to phospholipases that generate lipid mediators. These lipid mediators amplify the damage occurring by mechanisms described above and produce serious complications such as ventricular arrhythmia following acute myocardial infarction.

A recombinant human annexin, preferably annexin V, is modified in such a way that its half-life in the vascular compartment is prolonged. This can be achieved in a variety of ways; three embodiments are an annexin coupled to polyethylene glycol, a homopolymer or heteropolymer of annexin, and a fusion protein of annexin with another protein (e.g., the Fc portion of immunoglobulin). See Allison, "Modified Annexin Proteins and Methods for Preventing Thrombosis," U.S. patent application Ser. No. 10/080,370 (filed Feb. 21, 2002), now U.S. Pat. No. 6,962,903, and Allison, "Modified Annexin Proteins and Methods for Treating Vaso-Occlusive Sickle-Cell Disease," U.S. patent application Ser. No. 10/632, 694 (filed Aug. 1, 2003), now U.S. Pat. No. 6,982,154, both incorporated by reference herein in their entirety.

The modified annexin binds with high affinity to phosphatidylserine on the surface of epithelial and other cells, thereby preventing the binding of phagocytes and the operation of phospholipases, which release lipid mediators. The modified annexin therefore inhibits both cellular and humoral mechanisms of reperfusion injury.

In one embodiment, the present invention provides an isolated modified annexin protein containing an annexin protein coupled to at least one additional protein, such as an additional annexin protein (forming a homodimer), polyethylene glycol, or the Fc portion of immunoglobulin. The additional protein preferably has a molecular weight of at least 30 kDa. Also provided by the present invention are pharmaceutical compositions containing an amount of any of the modified annexin proteins of the invention that is effective for preventing or reducing reperfusion injury.

In some methods of the invention, the modified annexin is administered to a subject at risk of reperfusion injury in a pharmaceutical composition having an amount of any one of the modified annexin proteins of the present invention effective for preventing or attenuating reperfusion injury. For example, the pharmaceutical composition may be administered before and after organ transplantation, arthroplasty or other surgical procedure in which the blood supply to organ or tissue is cut off and after an interval restored. It can also be administered after a coronary or cerebral thrombosis.

The modified annexin binds PS accessible on cell surfaces (shielding the cells), thereby preventing the attachment of monocytes and the irreversible stage of apoptosis. In addition, the modified annexin inhibits the activity of phospholipases that generate lipid mediators that also contribute to RI. The modified annexin will be useful to prevent or attenuate RI and protect organs in organs transplanted from cadaver donors, in patients with coronary and cerebral thrombosis, in patients undergoing arthroplasties, and in other situations. In addition the modified annexin will exert prolonged antithrombotic activity without increasing hemorrhage. This combination of antithrombotic potency with capacity to attenuate RI presents a unique profile of desirable activities not displayed by any therapeutic agent currently used or known to be in development.

Figure 4A:
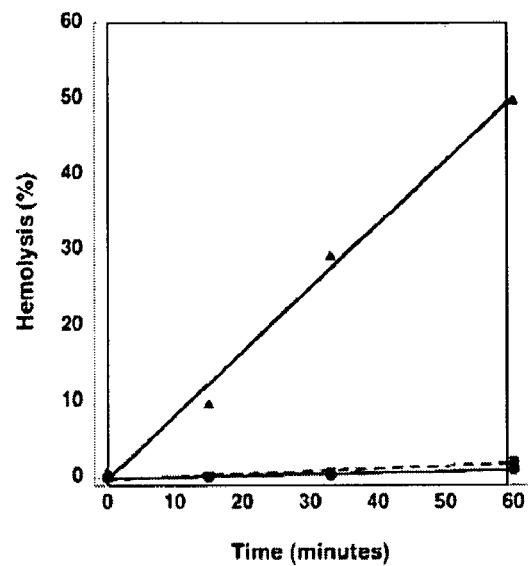
FIG. 4A shows hemolysis induced by 100 ng/ml $pPLA_2$ in absence (triangles) or presence of 2 μg/ml DAV (circles) or AV (squares).
Figure 4B:
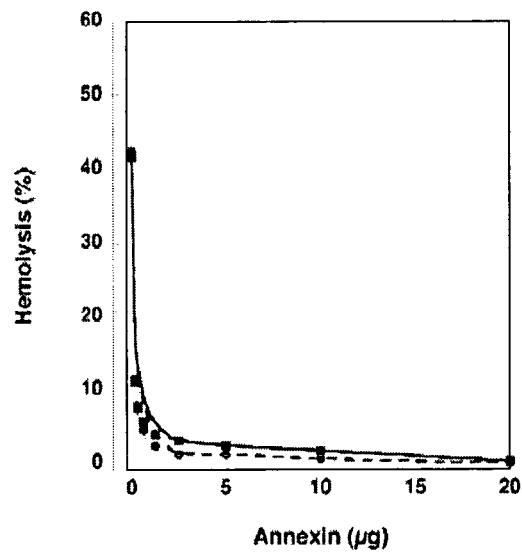
FIG. 4B shows hemolysis induced by 100 ng/ml $pPLA_2$ in the presence of various amounts of DAV (circles) or AV (squares).
Figure 4C:
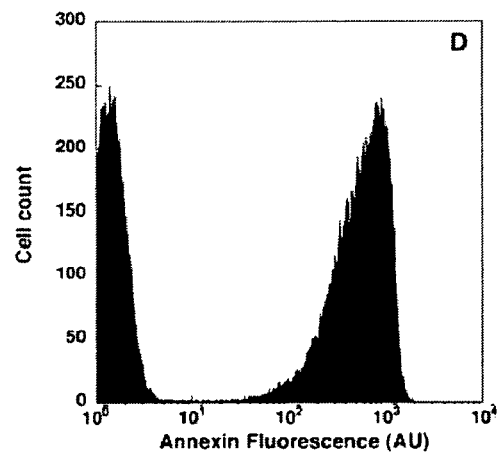
FIG. 4C shows PS-exposing cells in the cell suspension after 60 minutes incubation with 100 ng/ml $pPLA_2$ in the presence of 2 μg/ml DAV.

As described in Example 6, the annexin homodimer is a potent inhibitor of $sPLA_2$ (FIG. 4). Because annexin V binds to PS on cell surfaces with high affinity, it shields PS from degradation by $sPLA_2$ and other phospholipases.

Producing a homodimer of human annexin V both increased its affinity for PS, thereby improving its efficacy as a therapeutic agent; and augmented its size, thereby prolonging its survival in the circulation and duration of action. The 36 kDa monomer is lost rapidly from the blood stream into the kidneys. In the rabbit more than 80% of labeled annexin V injected into the circulation disappears in 7 minutes (Thiagarajan and Benedict, Circulation 96: 2339, 1997). In cynomolgus monkeys the half-life of injected annexin V was found to be 11 to 15 minutes (Romisch et al., Thrombosis Res., 61: 93, 1991). In humans injected with annexin V labeled with 99MTc, the half-life with respect to the major ($\alpha$) compartment was 24 minutes (Kemerink et al., J. Nucl. Med. 44: 947, 2003).

The annexin homodimer may be produced by any convenient method. In some embodiments, the annexin homodimer is produced by recombinant DNA technology as this avoids the necessity for post-translation procedures such as linkage to the one available sulfhydryl group in the monomer or coupling with polyethylene glycol. Recombinant homodimerization was achieved by the use of a flexible peptide linker attached to the amino terminus of one annexin monomer and the carboxy terminus of the other (FIG. 1). The three-dimensional structure of annexin V, and the residues binding $Ca^{2+}$ and PS, are known from X-ray crystallography and site-specific mutagenesis (Huber et al., J. Mol. Biol. 223: 683, 1992; Campos et al., 37: 8004, 1998). The $Ca^{2+}$- and PS-binding sites are on the convex surface of the molecule while the amino terminus forms a loose tail on the concave surface. The annexin V homodimer shown in FIG. 1 is designed so that the convex surfaces could fold in such a way that both could gain access to PS on cell surfaces. Thus, for this reason, the dimer would have a higher affinity for PS than that of the monomer. As reported in Example 4, this was verified experimentally. Another advantage of the homodimer of annexin V is that while a molecule of 36 kDa (the monomer) would be lost rapidly from circulation into the kidney, one of 73 kDa (the dimer), exceeding the renal filtration threshold, would not. Hence, the therapeutically useful activity would be prolonged in the dimer. This prediction was confirmed in experiments.

To prevent or attenuate reinfarction and RI, it is desirable, in some instances, to have a longer duration of activity. Increasing the molecular weight of annexin V by homodimerization to 76 kDa prevents renal loss and extends survival in the circulation. Accordingly, such modified annexins may effectively attenuate RI, even when administered several hours before the blood supply to an organ is cut off.

The teachings of the present invention are contrary to reports in the literature suggesting that annexin V does not inhibit RI. For example, d'Amico et al. report that annexin V did not inhibit RI in the rat heart whereas lipocortin I (annexin I) did (d'Amico et al., FASEB J. 14: 1867, 2000). A fragment of lipocortin I, injected into the cerebral ventricle of rats, was reported to decrease infarct size and cerebral edema after cerebral ischemia (Pelton et al., J. Exp. Med. 174: 305, 1991); these authors did not study reperfusion. In a comprehensive review of strategies to prevent ischemic injury of the liver (Selzner et al., Gastroenterology 15:917, 2003), annexin is not mentioned.

Figure 5:
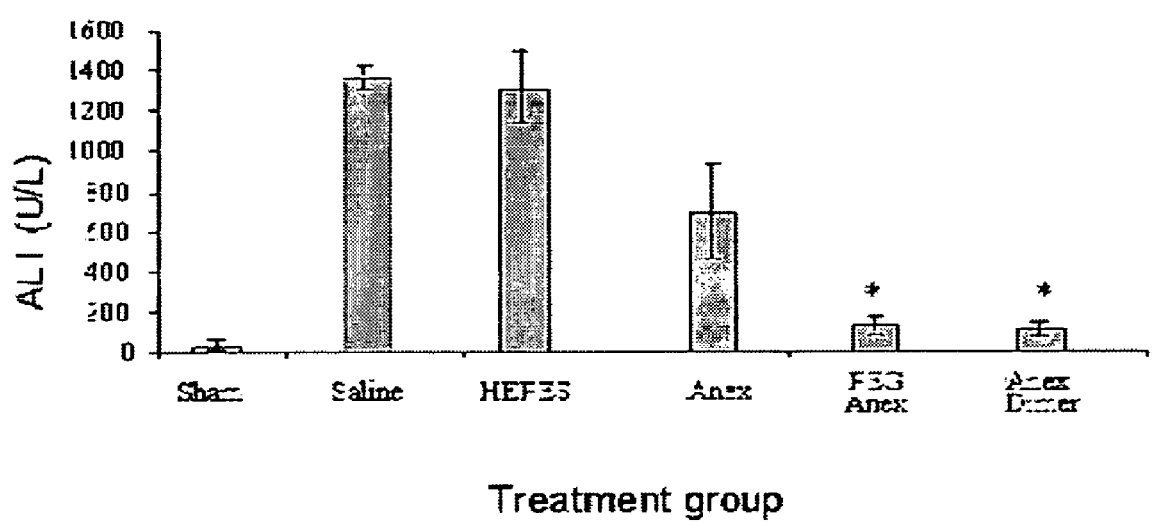
FIG. 5 shows serum alanine aminotransferase (ALT) levels in mice sham operated (Sham), mice given saline, mice given HEPES buffer 6 hrs. before clamping the hepatic artery, mice given pegylated annexin (PEG Anex) or annexin dimer 6 hrs. before clamping the artery, and mice given monomeric annexin (Anex). The asterisk above PEG ANNEX and ANNEX DIMER indicates p<0.001.

As described in Example 7, the ability of the annexin V homodimer to attenuate RI was tested in a mouse liver model (Teoh et al., Hepatology 36:94, 2002). In this model, the blood supply to the left lateral and median lobes of the liver is cut off for 90 minutes and then restored. After 24 hours, the severity of liver injury is assessed by serum levels of alanine aminotransferase (ALT) and hepatic histology. Both the annexin V homodimer (DAV), molecular weight 73 kDa, and annexin V coupled to polyethylene glycol (PEG-AV), molecular weight 57 kDa, injected 6 hours before clamping the hepatic arteries, were highly effective in attenuating RI as shown by serum ALT levels (FIG. 5) and hepatic histology. The annexin V monomer (AV) was less protective in this model. In Example 13, a similar procedure was performed in which the annexin V homodimer was administered at 10 minutes and 60 minutes after the commencement of reperfusion. Similar protection against IRI is found.

The experimental evidence therefore confirms that the modified annexins of the present invention will be useful to attenuate RI in subjects. As discussed above, similar pathogenetic mechanisms are involved in the forms of RI occurring in different organs, thus, the annexin V homodimer may be used to attenuate RI in all of them.

Because of its high affinity for PS and reduced loss from the circulation, the annexin V homodimer will exert prolonged antithrombotic activity. This is clinically useful to prevent reinfarction, which is known to be an important event following coronary thrombosis (Andersen et al., N. Engl. J. Med. 349: 733, 2003), and is likely to be important in stroke. Prevention of thrombosis in patients undergoing arthroplasty is also a major clinical need. The additional activity of a modified annexin as an anticoagulant is therefore valuable. In several experimental animal models, annexin V inhibits arterial and venous thrombosis without increasing hemorrhage (Römisch et al., Thromb. Res. 61: 93, 1991; Van Ryn-McKenna et al., Thromb. Hemost. 69: 227, 1993; Thiagarajan and Benedict, Circulation 96: 2339, 1997). A modified annexin has the capacity to exert anticoagulant activity without increasing hemorrhage and to attenuate reperfusion injury. This combination of actions could be useful in several clinical situations. No other therapeutic agent currently used, or known to be in development, shares this desirable profile of activities.

Several annexins, other than annexin V, bind $Ca^{2+}$ and PS. Any of these might be used to prevent or diminish reperfusion injury. The molecular weight of annexin V, or another annexin, may be increased by procedures other than homodimerization. Such procedures include the preparation of other homopolymers or heteropolymers. Alternatively, an annexin might be conjugated to another protein by recombinant DNA technology or chemical manipulation. Conjugation of an annexin to polyethylene glycol or another nonpeptide compound are also envisaged.

It is expected that the annexin V homodimer will be well-tolerated. Another annexin, annexin VI, is a naturally existing homodimer of the conserved annexin sequence. However, annexin VI does not bind PS with high affinity A PS-binding protein other than an annexin may also be used in the methods of the invention. For example, a monoclonal or polyclonal antibody with a high affinity for PS (Diaz et al., Bioconjugate Chem. 9:250, 1998; Thorpe et al., U.S. Pat. No. 6,312,694) may be used according to the present invention (e.g., for decreasing or preventing reperfusion injury).

Figure 7:
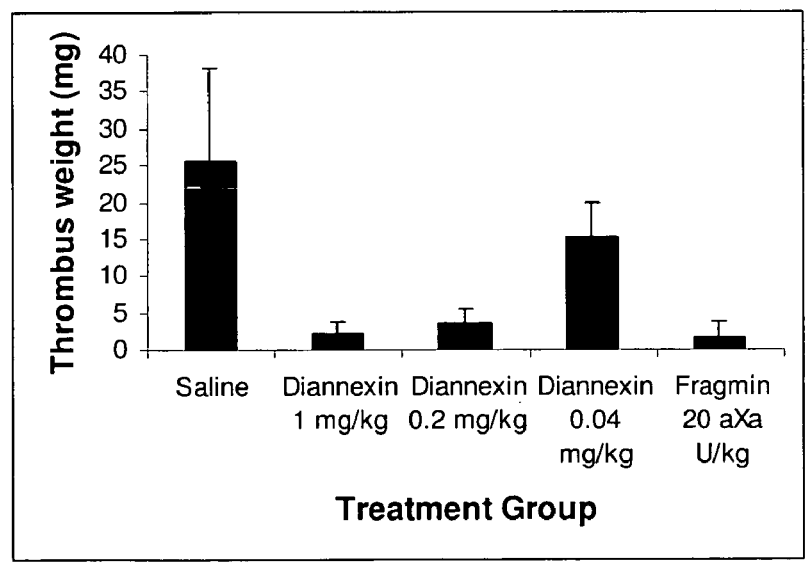
FIG. 7 shows thrombus weight in the five treatment groups of the 10-minute thrombosis study (mean±sd; n=8).
Figure 8:
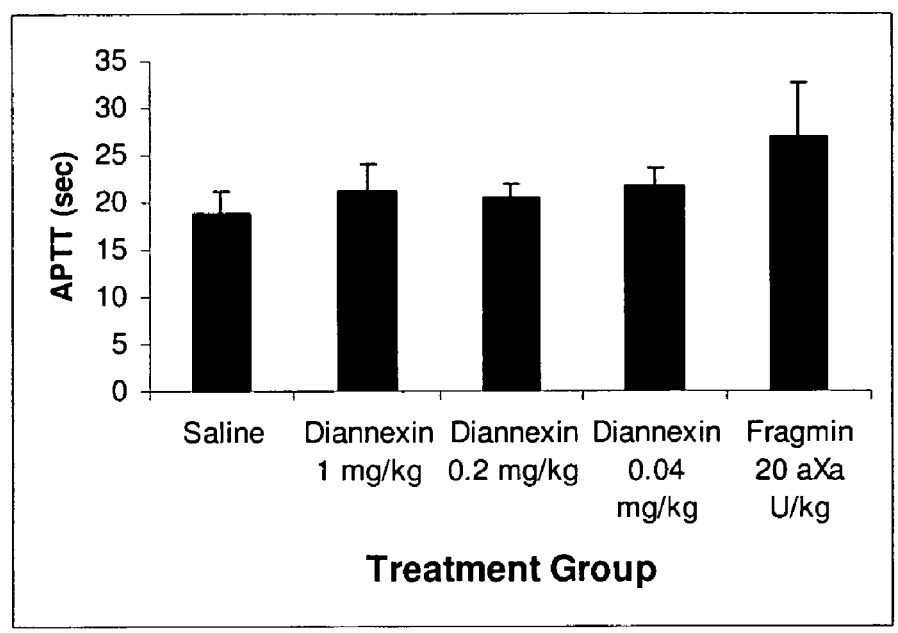
FIG. 8 shows APTT in the five treatment groups of the thrombosis study (mean±sd; n=8).
Figure 9:
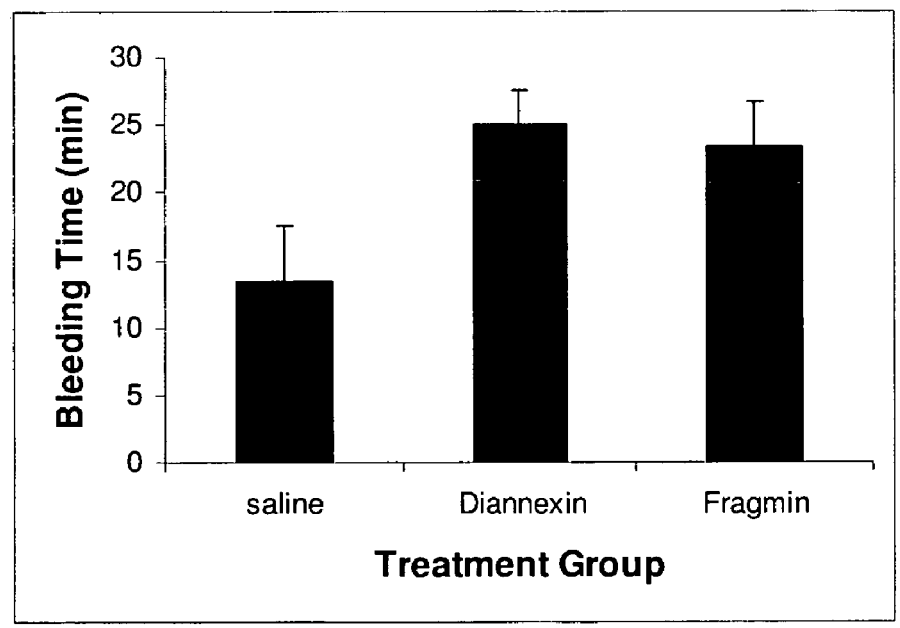
FIG. 9 shows bleeding time in the three groups of the tail bleeding study (mean±sd; n=8).
Figure 10:
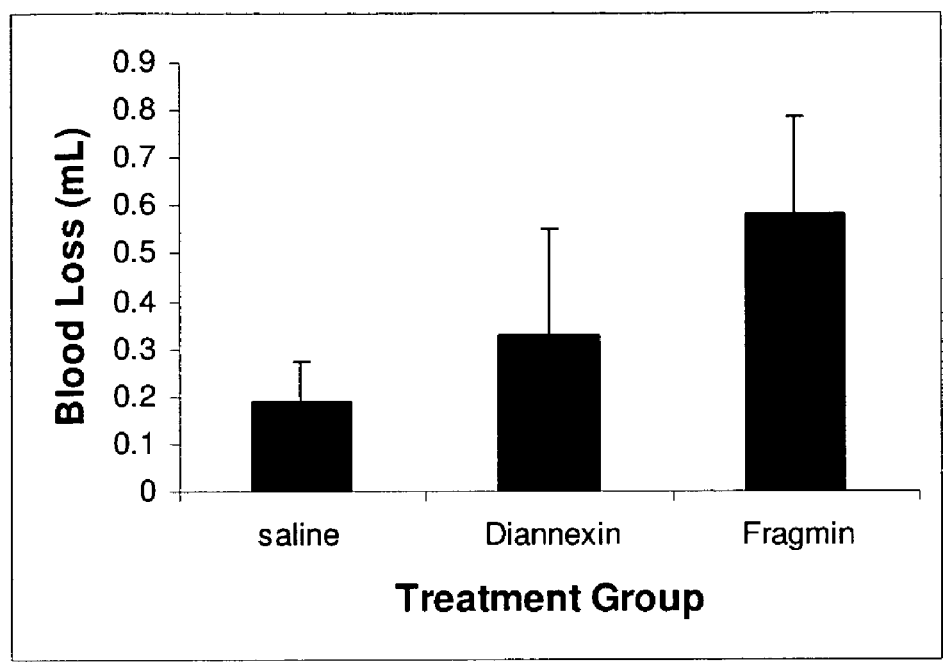
FIG. 10 shows blood loss in the three groups of the tail bleeding study (mean±sem; n=8).

Diannexin (SEQ ID NO: 27) has dose-related antithrombotic activity in the rat (FIG. 7). In contrast, Fragmin (low molecular weight heparin) administered at 140 aXa units/kg (approx. 7× therapeutic dose) significantly increased blood loss in experiments conducted simultaneously (table 4 and FIG. 10). Regarding the APTT (activated prothrombin time), none of the doses of Diannexin used increased the APTT, whereas both 20 aXa units/kg (table 2) of Fragmin, and 140 aXa units/kg (table 5 and FIG. 11) significantly increased the APTT. Clearance of iodine-labeled Diannexin could be described by a two-compartment model, an $\alpha$-phase of 9-14 min and a $\beta$-phase of 6-7 hrs (FIG. 12). The latter is significantly longer than previously reported for annexin IV monomer in several species. The 6.5 hour half life is convenient therapeutically because a single bolus injection should suffice for many clinical applications of Diannexin. In the unlikely event that Diannexin induces hemorrhage its effects will disappear fairly soon. Both Diannexin and Fragmin significantly increase the bleeding time in the rat following tail transection (FIG. 9 and table 4). In the case of Diannexin this may be due to inhibition of phospholipase $A_2$ action and thromboxane generation. In humans bleeding times are increased when cyclooxygenase is inhibited by a drug or as a result of a genetic deficiency. Diannexin administration has no effect on body weight.

The present invention provides compounds and methods for preventing or attenuating cold ischemia-warm reperfusion injury in mammals. As described above, organs to be used for transplantation are typically recovered from cadaver donors and perfused with a saline solution such as the University of Wisconsin solution originally introduced by Belzer et al. (Transplantation 1988; 45: 673). The organs are then preserved on ice for several hours before being transplanted. During this period the organ is anoxic, which results in depletion of ATP and loss of phospholipid asymmetry in the plasma membranes of endothelial cells (EC) and other cells. Under normal conditions an ATP-dependent phospholipid translocase maintains this asymmetry, which confines PS to the inner leaflet of the plasma membrane bilayer. Following anoxia PS is demonstrable on the outer leaflet of the EC plasma membrane, as shown by annexin V binding to the surface of cultured cells (Ran et al. Cancer Res. 2002; 62: 6132) Generally, the present invention comprises a method of protecting organs or tissue susceptible to IRI, wherein said organs or tissue are contacted with a modified annexin protein. Thus, the organs or tissue can be contacted with a modified annexin protein by parenterally administering about 10 to 1000 µg/kg of modified annexin protein to a patient who has organs or tissue susceptible to a condition of IRI, even in the case of donors with fatty livers. In some embodiments, the modified annexin protein is administered in a range of about 100 to 500 µg/kg. Modified annexin proteins are shown herein to attenuate IRI in organ transplantation, even in the case of patient with a fatty liver. The ability to attenuate IRI in the case of a steatotic liver transplant will increase the number of livers considered suitable for use. The present invention therefore has utility as the number of patients who would benefit from liver transplantation greatly exceeds the number of organs available.

In another embodiment of the invention, to protect organ transplants, modified annexin proteins can be added to the preservation fluid used for in situ organ perfusion and cooling in the donor and for cold storage or perfusion after the organ is harvested. The organ or tissue transplants can be perfused or flushed with a solution containing modified annexin proteins in a concentration of 0.1 to 1 mg/l. Typically, the organs or tissue are perfused with a solution containing, in addition to modified annexin proteins, components such as electrolytes and cell-protecting agents. According to the present invention, a modified annexin, such as SEQ ID NO:6, SEQ ID NO:19, or SEQ ID NO:23 is used.

In summary, when used for treating patients, modified annexin proteins are, according to the present invention, administered intravenously, subcutaneously, or by other suitable route. In addition we have demonstrated that when Diannexin is added to the University of Wisconsin solution perfusing rat livers ex vivo after recovery, before overnight storage at 4° and just before transplantation, it is also effective in preventing IRI and protecting organs in recipients. This provides an alternative or supplementary method of administration when Diannexin is used to prevent IRI and protect the organ in liver graft recipients. Addition of Diannexin to the fluid perfusing kidneys, hearts and other organs may also decrease IR following transplantation.

Turning now to the use of modified annexin proteins in preservation or rinse solutions it can be reiterated that by adding modified annexin proteins to the preservation solution used for organ perfusion and cooling in the donor and for cold storage or perfusion after the organ is harvested, IR injury in the organ transplant can be prevented and functional recovery after transplantation promoted. Modified annexin proteins may be added to different types of preservation solutions, which typically contain electrolytes (such as $Na^+$, $K^+$, $Mg^{++}$, $Cl^-$, $SO_4^{2-}$, $HPO_4^{2-}$, $Ca^{2+}$ and $HCO_3^-$) and may contain various other agents protecting the cells during cold storage. For example, AGP and/or AAT can be added to the University of Wisconsin Belzer solution which contains 50 g/l hydroxyethyl starch, 35.83 g/l lactobionic acid, 3.4 g/l potassium phosphate monobasic, 1.23 g/l magnesium sulfate heptahydrate, 17.83 g/l raffinose pentahydrate, 1.34 g/l adenosine, 0.136 g/l allopurinol, 0.922 g/l glutathionine, 5.61 g/l potassium hydroxide and sodium hydroxide for adjustment of pH to pH 7.4. Another example of a suitable preservation solution is the Euro-Collins solution, which contains 2.05 g/l monopotassium phosphate, 7.4 g/l dipotassium phosphate, 1.12 g/l potassium chloride, 0.84 g/l sodium bicarbonate and 35 g/l glucose. These intracellular type preservation solutions are rinsed away from the donor organ before completion of transplantation into the recipient by using a physiological infusion solution, such as Ringer's solution, and modified annexin proteins can be also added to a rinse solution. Further, modified annexin proteins can be added to extracellular type preservation solutions which need to be flushed away, such as PEFADEX (Vitrolife, Sweden), which contains 50 g/l dextran, 8 g/l sodium chloride, 400 mg/l potassium chloride, 98 mg/l magnesium sulfate, 46 mg/l disodium phosphate, 63 mg/l potassium phosphate and 910 mg/l glucose.

The novel preservation and rinsing solutions according to the present invention may have a composition essentially corresponding to any of the three commercial solutions described above. However, the actual concentrations of the conventional components may vary somewhat, typically within a range of about ±50%, preferably about ±30%, of the mean values given above.

In one embodiment, to ensure maximum activity, modified annexin proteins are added to a ready-made preservation or rinse solution just before use. Alternatively, a suitable preservation solution containing modified annexin proteins may be prepared beforehand.

By administrating modified annexin proteins to a recipient of an organ transplant at time of transplantation, development of IR injury in the organ transplant can be prevented and the organ can be protected. As a result of this, the function of the organ transplant is more rapidly recovered , which is a prerequisite for the success of the organ transplantation. In kidney transplantations, the prevention of renal dysfunction after transplantation decreases dependence of the patient on hemodialysis. In liver, heart and lung transplantations, the early proper function of the organ transplant is critical and prevention of graft dysfunction should decrease mortality of the patients. By adding modified annexin proteins to the artificial preservation solution used for organ perfusion and cooling and for cold storage, IR injury in the organ transplant can be also prevented, the organ protected, and functional recovery after transplantation promoted.

By administrating modified annexin proteins to patients undergoing cardiac or angioplastic surgery, development of IR injury following the operation can be prevented and the heart can be protected. This decreases the need of postoperative critical care. Correspondingly, by administering modified annexin proteins to patients undergoing thrombolytic therapy, development of IR injury during reperfusion of the occluded vessel can be prevented and organ dysfunction can be avoided. In thrombolytic therapy of myocardial infarction this may prevent cardiac arrhythmias and cardiac insufficiency. In thrombolytic therapy of brain infarction, this may decrease neurological symptoms and palsies. By administrating modified annexin proteins to patients suffering from bleeding shock, septic shock, or other forms of shock, development of IR injury can be prevented.

According to an embodiment of the present invention, modified annexin proteins and mixtures thereof are used in methods for preparing pharmaceutical compositions intended for use in any of the therapeutic methods of treatment described above.

The present invention is also directed toward therapeutic compositions comprising the modified annexin proteins of the present invention. Compositions of the present invention can also include other components such as a pharmaceutically acceptable excipient, an adjuvant, and/or a carrier. For example, compositions of the present invention can be formulated in an excipient that the animal to be treated can tolerate. Examples of such excipients include water, saline, Ringer's solution, dextrose solution, mannitol, Hanks' solution, and other aqueous physiologically balanced salt solutions. Nonaqueous vehicles, such as triglycerides may also be used. Excipients can also contain minor amounts of additives, such as substances that enhance isotonicity and chemical stability. Examples of buffers include phosphate buffer, bicarbonate buffer, Tris buffer, histidine, citrate, and glycine, or mixtures thereof, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

One embodiment of the present invention is a controlled release formulation that is capable of slowly releasing a composition of the present invention into an animal. As used herein, a controlled release formulation comprises a composition of the present invention in a controlled release vehicle. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release formulations of the present invention include liquids that, upon administration to an animal, form a solid or a gel in situ. Preferred controlled release formulations are biodegradable (i.e., bioerodible).

Generally, the therapeutic agents used in the invention are administered to an animal in an effective amount. Generally, an effective amount is an amount effective to either (1) reduce the symptoms of the disease sought to be treated or (2) induce a pharmacological change relevant to treating the disease sought to be treated.

Therapeutically effective amounts of the therapeutic agents can be any amount or doses sufficient to bring about the desired effect and depend, in part, on the condition, type and location of the thrombosis, the size and condition of the patient, as well as other factors readily known to those skilled in the art. The dosages can be given as a single dose, or as several doses, for example, divided over the course of several days.

The present invention is also directed toward methods of treatment utilizing the therapeutic compositions of the present invention. The method comprises administering the therapeutic agent to a subject in need of such administration.

The therapeutic agents of the instant invention can be administered by any suitable means, including, for example, parenteral, topical, oral or local administration, such as intradermally, by injection, or by aerosol. In one embodiment of the invention, the agent is administered by injection. Such injection can be locally administered to any affected area. A therapeutic composition can be administered in a variety of unit dosage forms depending upon the method of administration. Suitable delivery methods for a therapeutic composition of the present invention include intravenous administration and local administration by, for example, injection or introduction into an intravenous drip. For particular modes of delivery, a therapeutic composition of the present invention can be formulated in an excipient. A therapeutic reagent of the present invention can be administered to any animal, preferably to mammals, and more preferably to humans.

The particular mode of administration will depend on the condition to be treated. It is contemplated that administration of the agents of the present invention may be via any bodily fluid, or any target or any tissue accessible through a body fluid.

Examples of such fluid include blood and blood products. In liver transplantation, which is included in the present invention, thrombocytopenia is common and blood platelets are transfused. The survival of blood platelets may be improved by co-administration of an annexin or modified annexin such as Diannexin. Stored platelets often express phosphatidylserine on their surfaces, facilitating attachment to one another on to monocyte-macrophage lineage cells. An annexin could mask PS on the surface of platelets, thereby improving their survival during storage and in patients. Accordingly, the present invention provides a method of increasing the duration of survival of blood platelets, comprising adding an isolated annexin protein to stored platelets. The isolated annexin protein may be modified, and in some embodiments may be an annexin dimer. The addition may be in a platelet storage medium. The addition may also be in a patient to whom platelets are administered, including the case where the patient is the recipient of a liver graft, including a thrombocytopenic liver graft patient.

The following examples illustrate the preparation of modified annexin proteins of the invention and in vitro and in vivo assays for anticoagulant activity of modified annexin proteins. It is to be understood that the invention is not limited to the exemplary work described or to the specific details set forth in the examples.

EXAMPLES

Example 1

Modified Annexin Preparation

A. PEGylated Annexins.

Annexins can be purified from human tissues or produced by recombinant technology. For instance, annexin V can be purified from human placentas as described by Funakoshi et al. (1987). Examples of recombinant products are the expression of annexin II and annexin V in *Escherichia coli* (Kang, H.-M., *Trends Cardiovasc. Med.* 9:92-102 (1999); Thiagarajan and Benedict, 1997, 2000). A rapid and efficient purification method for recombinant annexin V, based on $Ca^{2+}$-enhanced binding to phosphatidylserine-containing liposomes and subsequent elution by EDTA, has been described by Berger, *FEBS Lett.* 329:25-28 (1993). This procedure can be improved by the use of phosphatidylserine coupled to a solid phase support.

Annexins can be coupled to polyethylene glycol (PEG) by any of several well-established procedures (reviewed by Hermanson, 1996) in a process referred to as pegylation. The present invention includes chemically-derivatized annexin molecules having mono- or poly-(e.g., 2-4) PEG moieties. Methods for preparing a pegylated annexin generally include the steps of (a) reacting the annexin with polyethylene glycol (such as a reactive ester or aldehyde derivative of PEG) under conditions whereby the annexin becomes attached to one or more PEG groups and (b) obtaining the reaction product or products. In general, the optimal reaction conditions for the reactions must be determined case by case based on known parameters and the desired result. Furthermore, the reaction may produce different products having a different number of PEG chains, and further purification may be needed to obtain the desired product.

Conjugation of PEG to annexin V can be performed using the EDC plus sulfo-NHS procedure. EDC (1-ethyl-3-(3-dimethylaminopropyl)-carbodiimide hydrochloride) is used to form active ester groups with carboxylate groups using sulfo-NHS (N-hydroxysulfosuccinamide). This increases the stability of the active intermediate, which reacts with an amine to give a stable amide linkage. The conjugation can be carried out as described in Hermanson, 1996.

Bioconjugate methods can be used to produce homopolymers or heteropolymers of annexin; methods are reviewed by Hermanson, 1996. Recombinant methods can also be used to produce fusion proteins, e.g., annexin expressed with the Fc portion of immunoglobulin or another protein. The heterotetramer of annexin II with P11 has also been produced in *E. coli* (Kang et al., 1999). All of these procedures increase the molecular weight of annexin and have the potential to increase the half-life of annexin in the circulation and prolong its anticoagulant effect.

B. Homodimer of Annexin V.

A homodimer of annexin V can be produced using a DNA construct shown schematically in FIG. 1C (5'-3' sense strand) (SEQ ID NO:4) and coding for an amino acid sequence represented by SEQ ID NO:6. In this example, the annexin V gene is cloned into the expression vector pCMV FLAG 2 (available from Sigma-Aldrich) at EcoRI and BglII sites. The exact sequences prior to and after the annexin V sequence are unknown and denoted as "x". It is therefore necessary to sequence the construct prior to modification to assure proper codon alignment. The pCMV FLAG 2 vector comes with a strong promotor and initiation sequence (Kozak) and start site (ATG) built in. The start codon before each annexin V gene must therefore be removed, and a strong stop for tight expression should be added at the terminus of the second annexin V gene. The vector also comes with an 8-amino acid peptide sequence that can be used for protein purification (asp-tyr-lys-asp-asp-asp-asp-lys) (SEQ ID NO:9). A 14-amino acid spacer with glycine-serine swivel ends allows optimal rotation between tandem gene-encoded proteins. Addition of restriction sites PvuII and ScaI allow removal of the linker if necessary. Addition of a protease site allows cleavage of tandem proteins following expression. PreScission™ protease is available from Amersham Pharmacia Biotech and can be used to cleave tandem proteins. Two annexin V homodimers were generated. In the first, a "His tag" was placed at the amino terminal end of the dimer to facilitate purification (FIG. 1A). The linker sequence of 12 amino acids was flanked by a glycine and a serine residue at either end to serve as swivels. The structural scheme is shown in FIG. 1A. The amino acid sequence of the His-tagged annexin V homodimer is provided below:

```
                                          SEQ ID NO:26
MHHHHHHQAQVLRGTVTDFPGFDERADAETLRKAMKGLGTDEESILTLLT

SRSNAQRQEISAAFKTLFGRDLLDDLKSELTGKFEKLIVALMKPSRLYDA

YELKHALKGAGTNEKVLTEIIASRTPEELRAIKQVYEEEYGSSLEDDVVG

DTSGYYQRMLVVLLQANRDPDAGIDEAQVEQDAQALFQAGELKWGTDEEK

FITIFGTRSVSHLRKVFDKYMTISGFQIEETIDRETSGNLEQLLLAVVKS

IRSIPAYLAETLYYAMKGAGTDDHTLIRVMVSRSEIDLFNIRKEFRKNFA

TSLYSMIKGDTSGDYKKALLLLCGEDDGSLEVLFQGPSGKLAQVLRGTVT

DFPGFDERADAETLRKAMKGLGTDEESILTLLTSRSNAQRQEISAAFKTL

FGRDLLDDLKSELTGKFEKLIVALMKPSRLYDAYELKHALKGAGTNEKVL

TEIIASRTPEELRAIKQVYEEEYGSSLEDDVVGDTSGYYQRMLVVLLQAN

RDPDAGIDEAQVEQDAQALFQAGELKWGTDEEKFITIFGTRSVSHLRKVF

DKYMTISGFQIEETIDRETSGNLEQLLLAVVKSIRSIPAYLAETLYYAMK

GAGTDDHTLIRVMVSRSEIDLFNIRKEFRKNFATSLYSMIKGDTSGDYKK

ALLLLCGEDD
```

The "swivel" amino acids of the linker are bolded and underlined. This His-tagged annexin V homodimer was expressed at a high level in *Escherichia coli* and purified using a nickel column. The DNA in the construct was shown to have the correct sequence and the dimer had the predicted molecular weight (74 kDa). MALDI-TOF mass spectrometry was accomplished using a PerSeptive Biosystems Voyager-DE Pro workstation operating in linear, positive ion mode with a static accelerating voltage of 25 kV and a delay time of 40 nsec.

A second human annexin V homodimer was synthesized without the His tag. The structural scheme is shown in FIG. 1B. The amino acid sequence of the (non-His-tagged) annexin V homodimer is provided below:

(SEQ ID NO:27)
MAQVLRGTVTDFPGFDERADAETLRKAMKGLGTDEESILTLLTSRSNAQR

QEISAAFKTLFGRDLLDDLKSELTGKFEKLIVALMKPSRLYDAYELKHAL

KGAGTNEKVLTEIIASRTPEELRAIKQVYEEEYGSSLEDDVVGDTSGYYQ

RMLVVLLQANRDPDAGIDEAQVEQDAQALFQAGELKWGTDEEKFITIFGT

RSVSHLRKVFDKYMTISGFQIEETIDRETSGNLEQLLLAVVKSIRSIPAY

LAETLYYAMKGAGTDDHTLIRVMVSRSEIDLFNIRKEFRKNFATSLYSMI

KGDTSGDYKKALLLLCGEDDGSLEVLFQGPSGKLAQVLRGTVTDFPGFDE

RADAETLRKAMKGLGTDEESILTLLTSRSNAQRQEISAAFKTLFGRDLLD

DLKSELTGKFEKLIVALMKPSRLYDAYELKHALKGAGTNEKVLTEIIASR

TPEELRAIKQVYEEEYGSSLEDDVVGDTSGYYQRMLVVLLQANRDPDAGI

DEAQVEQDAQALFQAGELKWGTDEEKFITIFGTRSVSHLRKVFDKYMTIS

GFQIEETIDRETSGNLEQLLLAVVKSIRSIPAYLAETLYYAMKGAGTDDH

TLIRVMVSRSEIDLFNIRKEFRKNFATSLYSMIKGDTSGDYKKALLLLCG

EDD

Again, the "swivel" amino acids of the linker are bolded and underlined. This dimer was expressed at a high level in *E. coli* and purified by ion-exchange chromatography followed by heparin affinity chromatography. The ion-exchange column was from Bio-Rad (Econo-pak HighQ Support) and the heparin affinity column was from Amersham Biosciences (HiTrap Heparin HP). Both were used according to manufacturers' instructions. Again, the DNA sequence of the annexin V homodimer was found to be correct. Mass spectrometry showed a protein of 73 kDa, as expected. The amino acid sequence of annexin and other proteins is routinely determined in this laboratory by mass spectrometry of peptide fragments. Expected sequences were obtained.

Human Annexin V has the following amino acid sequence:

(SEQ ID NO:3)
AQVLRGTVTDFPGFDERADAETLRKAMKGLGTDEESILTLLTSRSNAQRQ

EISAAFKTLFGRDLLDDLKSELTGKFEKLIVALMKPSRLYDAYELKHALK

GAGTNEKVLTEIIASRTPEELRAIKQVYEEEYGSSLEDDVVGDTSGYYQR

MLVVLLQANRDPDAGIDEAQVEQDAQALFQAGELKWGTDEEKFITIFGTR

SVSHLRKVFDKYMTISGFQIEETIDRETSGNLEQLLLAVVKSIRSIPAYL

AETLYYAMKGAGTDDHTLIRVMVSRSEIDLFNIRKEFRKNFATSLYSMIK

GDTSGDYKKALLLLCGEDD

The nucleotide sequence of human annexin V, inserted as indicated in the DNA construct illustrated in FIG. 1C, is as follows:

(SEQ ID NO:1)
GCACAGGTTCTCAGAGGCACTGTGACTGACTTCCCTGGATTTGATGAGCG

GGCTGATGCAGAAACTCTTCGGAAGGCTATGAAAGGCTTGGGCACAGATG

AGGAGAGCATCCTGACTCTGTTGACATCCCGAAGTAATGCTCAGCGCCAG

GAAATCTCTGCAGCTTTTAAGACTCTGTTTGGCAGGGATCTTCTGGATGA

CCTGAAATCAGAACTAACTGGAAAATTTGAAAAATTAATTGTGGCTCTGA

TGAAACCCTCTCGGCTTTATGATGCTTATGAACTGAAACATGCCTTGAAG

GGAGCTGGAACAAATGAAAAGTACTGACAGAAATTATTGCTTCAAGGAC

ACCTGAAGAACTGAGAGCCATCAAACAAGTTTATGAAGAAGAATATGGCT

CAAGCCTGGAAGATGACGTGGTGGGGGACACTTCAGGGTACTACCAGCGG

ATGTTGGTGGTTCTCCTTCAGGCTAACAGAGACCCTGATGCTGGAATTGA

TGAAGCTCAAGTTGAACAAGATGCTCAGGCTTTATTTCAGGCTGGAGAAC

TTAAATGGGGACAGATGAAGAAAAGTTTATCACCATCTTTGGAACACGA

AGTGTGTCTCATTTGAGAAAGGTGTTTGACAAGTACATGACTATATCAGG

ATTTCAAATTGAGGAAACCATTGACCGCGAGACTTCTGGCAATTTAGAGC

AACTACTCCTTGCTGTTGTGAAATCTATTCGAAGTATACCTGCCTACCTT

GCAGAGACCCTCTATTATGCTATGAAGGGAGCTGGGACAGATGATCATAC

CCTCATCAGAGTCATGGTTTCCAGGAGTGAGATTGATCTGTTTAACATCA

GGAAGGAGTTTAGGAAGAATTTTGCCACCTCTCTTTATTCCATGATTAAG

GGAGATACATCTGGGGACTATAAGAAAGCTCTTCTGCTGCTCTGTGG AG

AAGATGAC

C. Annexin IV Homodimer.

A homodimer of annexin IV was prepared similarly to the annexin V homodimer described in Example 1B. The vector used was pET-29a(+), available from Novagen Madison, Wis.). The plasmid sequence was denoted as pET-ANXA4-2X and was 7221 bp (SEQ ID NO:16). pET-ANXA4-2X contains an open reading frame from nucleotide number 5076 to 7049 (including 3 stop codons). The first copy of Annexin IV spans nucleotides 5076-6038 of SEQ ID NO: 16, a first swivel linker spans nucleotides 6039-6044 of SEQ ID NO: 16, the PreScission protease recognition site spans nucleotides 6045-6068 of SEQ ID NO: 16, the second swivel linker spans nucleotides 6069-6074 of SEQ ID NO: 16, the second copy of annexin IV spans nucleotides 6081-7043 of SEQ ID NO: 16, and a kanamycin resistance gene spans nucleotides 1375-560 of SEQ ID NO: 16. The sequence from nucleotide number 5076 to 7049 is further represented herein as SEQ ID NO:17. Translation of SEQ ID NO:17 results in the annexin IV homodimer polypeptide having the following amino acid sequence:

(SEQ ID NO:19)
MAMATKGGTVKAASGFNAMEDAQTLRKAMKGLGTDEDAIISVLAYRNTAQ

RQEIRTAYKSTIGRDLIDDLKSELSGNFEQVIVGMMTPTVLYDVQELRRA

MKGAGTDEGCLIEILASRTPEEIRRISQTYQQQYGRRLEDDIRSDTSFMF

QRVLVSLSAGGRDEGNYLDDALVRQDAQDLYEAGEKKWGTDEVKFLTVLC

SRNRNHLLHVFDEYKRISQKDIEQSIKSETSGSFEDALLAIVKCMRNKSA

YFAEKLYKSMKGLGTDDNTLIRVMVSRAEIDMLDIRAHFKRLYGKSLYSF

IKGDTSGDYRKVLLVLCGGDDGSlevlfqgpSG*KL*AMATKGGTVKAASGF

NAMEDAQTLRKAMKGLGTDEDAIISVLAYRNTAQRQEIRTAYKSTIGRDL

-continued

```
IDDLKSELSGNFEQVIVGMMTPTVLYDVQELRRAMKGAGTDEGCLIEILA

SRTPEEIRRISQTYQQQYGRRLEDDIRSDTSFMFQRVLVSLSAGGRDEGN

YLDDALVRQDAQDLYEAGEKKWGTDEVKFLTVLCSRNRNHLLHVFDEYKR

ISQKDIEQSIKSETSGSFEDALLAIVKCMRNKSAYFAEKLYKSMKGLGTD

DNTLIRVMVSRAEIDMLDIRAHFKRLYGKSLYSFIKGDTSGDYRKVLLVL

CGGDD
```

In the sequence above, the swivel sites are denoted by bold and underline, the PreScission protease site is in lower case, and an introduced restriction site is in italics. The annexin IV gene as cloned contained a single base substitution compared to the published sequence (GenBank accession number NM_001153) which changes the amino acid at position 137 from serine to arginine. This change is noted in bold and double underline in the amino acid sequence of the dimer above.

D. Annexin VIII Homodimer.

A homodimer of annexin VIII was prepared similarly to the annexin V homodimer described in Example 1B. The vector used was pET-29a(+), available from Novagen (Madison, Wis.). The plasmid sequence was denoted as pET-ANXA8-2X and was 7257 bp (SEQ ID NO:20). pET-ANXA4-2X contains an open reading frame from nucleotide number 5076 to 7085 (including 3 stop codons). The first copy of Annexin VIII spans nucleotides 5076-6056 of SEQ ID NO:20, a first swivel linker spans nucleotides 6057-6062 of SEQ ID NO:20, the PreScission protease recognition site spans nucleotides 6063-6086 of SEQ ID NO:20, the second swivel linker spans nucleotides 6087-6092 of SEQ ID NO:20, the second copy of annexin VIII spans nucleotides 6099-7079 of SEQ ID NO:20, and a kanamycin resistance gene spans nucleotides 1375-560 of SEQ ID NO:20. The sequence from nucleotide number 5076 to 7085 is further represented herein as SEQ ID NO:21. Translation of SEQ ID NO:21 results in the annexin VIII homodimer polypeptide having the following amino acid sequence:

```
                                           (SEQ ID NO:23)
MAWWKAWIEQEGVTVKSSSHFNPDPDAETLYKAMKGIGTNEQAIIDVLTK

RSNTQRQQIAKSFKAQFGKDLTETLKSELSGKFERLIVALMYPPYRYEAK

ELHDAMKGLGTKEGVIIEILASRTKNQLREIMKAYEEDYGSSLEEDIQAD

TSGYLERILVCLLQGSRDDVSSFVDPALALQDAQDLYAAGEKIRGTDEMK

FITILCTRSATHLLRVFEEYEKIANKSIEDSIKSETHGSLEEAMLTVVKC

TQNLHSYFAERLYYAMKGAGTRDGTLIRNIVSRSEIDLNLIKCHFKKMYG

KTLSSMIMEDTSGDYKNALLSLVGSDPGSlevlfqgpSGKLAWWKAWIEQ

EGVTVKSSSHFNPDPDAETLYKAMKGIGTNEQAIIDVLTKRSNTQRQQIA

KSFKAQFGKDLTETLKSELSGKFERLIVALMYPPYRYEAKELHDAMKGLG

TKEGVIIEILASRTKNQLREIMKAYEEDYGSSLEEDIQADTSGYLERILV

CLLQGSRDDVSSFVDPALALQDAQDLYAAGEKIRGTDEMKFITILCTRSA

THLLRVFEEYEKIANKSIEDSIKSETHGSLEEAMLTVVKCTQNLHSYFAE

RLYYAMKGAGTRDGTLIRNIVSRSEIDLNLIKCHFKKMYGKTLSSMIMED

TSGDYKNALLSLVGSDP
```

In the sequence above, the swivel sites are denoted by bold and underline, the PreScission protease site is in lower case, and an introduced restriction site is in italics. The annexin VIII gene as cloned contains a single base substitution compared to the published sequence (GenBank accession number NM_001630). The result is a codon change for tyrosine at position 92 from TAT to TAC.

Example 2

In Vitro and In Vivo Assays

In vitro assays determine the ability of modified annexin proteins to bind to activated platelets. Annexin V binds to platelets, and this binding is markedly increased in vitro by activation of the platelets with thrombin (Thiagarajan and Tait, 1990; Sun et al., 1993). Preferably, the modified annexin proteins of the present invention are prepared in such a way that perform the function of annexin in that they bind to platelets and prevent protein S from binding to platelets (Sun et al., 1993). The modified annexin proteins also perform the function of exhibiting the same anticoagulant activity in vitro that unmodified annexin proteins exhibit. A method for measuring the clotting time is the activated partial thromboplastin time (Fritsma, in *Hemostasis and thrombosis in the clinical laboratory* (Corriveau, D. M. and Fritsma, G. A., eds) J. P. Lipincott Co., Philadelphia (1989), pp.92-124, incorporated herein by reference).

In vivo assays determine the antithrombotic activity of annexin proteins. Annexin V has been shown to decrease venous thrombosis induced by a laser or photochemically in rats (Römisch et al., 1991). The maximal anticoagulant effect was observed between 15 and 30 minutes after intravenous administration of annexin V, as determined functionally by thromboelastography. The modified annexin proteins of the present invention preferably show more prolonged activity in such a model than unmodified annexin. Annexin V was also found to decrease fibrin accretion in a rabbit model of jugular vein thrombosis (Van Ryn-McKenna et al., 1993). Air injection was used to remove the endothelium, and annexin V was shown to bind to the treated vein but not to the control contralateral vein. Decreased fibrin accumulation in the injured vein was not associated with systemic anticoagulation. Heparin did not inhibit fibrin accumulation in the injured vein. The modified annexin proteins of the present invention preferably perform the function of annexin in this model of venous thrombosis. A rabbit model of arterial thrombosis was used by Thiagarajan and Benedict, 1997. A partially occlusive thrombus was formed in the left carotid artery by application of an electric current. Annexin V infusion strongly inhibited thrombosis as manifested by measurements of blood flow, thrombus weight, labeled fibrin deposition and labeled platelet accumulation. Recently, a mouse model of photochemically-induced thrombus in cremaster muscles was introduced (Vollmar et al. *Thromb. Haemost.* 85:160-164 (2001), incorporated herein by reference). Using this technique, thrombosis can be induced in any desired artery or vein. The modified annexin proteins of the present invention preferably perform the function of annexin in such models, even when administered by bolus injection.

Example 3

The anticoagulant ability of human recombinant annexin V and pegylated human recombinant annexin V were compared in vitro.

Annexin V Production. The polymerase chain reaction was used to amplify the cDNA from the initiator methionine to the stop codon with specific oligonucleotide primers from a human placental cDNA library. The forward primer was 5'-ACCTGAGTAGTCGCCATGGCACAGGTTCTC-3' (SEQ ID NO:7) and the reverse primer was 5'-CCCGAAT-TCACGTTAGTCATCTTCTCCACAGAGCAG-3' (SEQ ID NO:8). The amplified 1.1-kb fragment was digested with Nco I and Eco RI and ligated into the prokaryotic expression vector pTRC 99A. The ligation product was used to transform competent *Escherichia coli* strain JM 105 and sequenced.

Recombinant annexin V was isolated from the bacterial lysates as described by Berger et al., 1993, with some modification. An overnight culture of *E. coli* JM 105 transformed with pTRC 99A-annexin V was expanded 50-fold in fresh Luria-Bertrani medium containing 100 mg/L ampicillin. After 2 hours, isopropyl β-D-thiogalactopyranoside was added to a final concentration of 1 mmol/L. After 16 hours of induction, the bacteria were pelleted at 3500 g for 15 minutes at 4° C. The bacterial pellet was suspended in TBS, pH 7.5, containing 1 mmol/L PMSF, 5 mmol/L EDTA, and 6 mol/L urea. The bacterial suspension was sonicated with an ultrasonic probe at a setting of 6 on ice for 3 minutes. The lysate was centrifuged at 10,000 g for 15 minutes, and the supernatant was dialyzed twice against 50 vol TBS containing 1 mmol/L EDTA and once against 50 vol TBS.

Multilamellar liposomes were prepared by dissolving phosphatidylserine, lyophilized bovine brain extract, cholesterol, and dicetylphosphate in chloroform in a molar ratio of 10:15:1 and dried in a stream of nitrogen in a conical flask. TBS (5 mL) was added to the flask and agitated vigorously in a vortex mixer for 1 minute. The liposomes were washed by centrifugation at 3500 g for 15 minutes, then incubated with the bacterial extract, and calcium chloride was added to a final concentration of 5 mmol/L. After 15 minutes of incubation at 37° C., the liposomes were sedimented by centrifugation at 10,000 g for 10 minutes, and the bound annexin V was eluted with 10 mmol/L EDTA. The eluted annexin V was concentrated by Amicon ultrafiltration and loaded onto a Sephacryl S 200 column. The annexin V was recovered in the included volume, whereas most of the liposomes were in the void volume. Fractions containing annexin V were pooled and dialyzed in 10 mmol/L Tris and 2 mmol/L EDTA, pH 8.1, loaded onto an anion exchange column, and eluted with a linear gradient of 0 to 200 mmol/L NaCl in the same buffer. The purified preparation showed a single band in SDS-PAGE under reducing conditions.

The annexin V produced as above was pegylated using the method of Hermanson, 1996, as described above.

Figure 6:
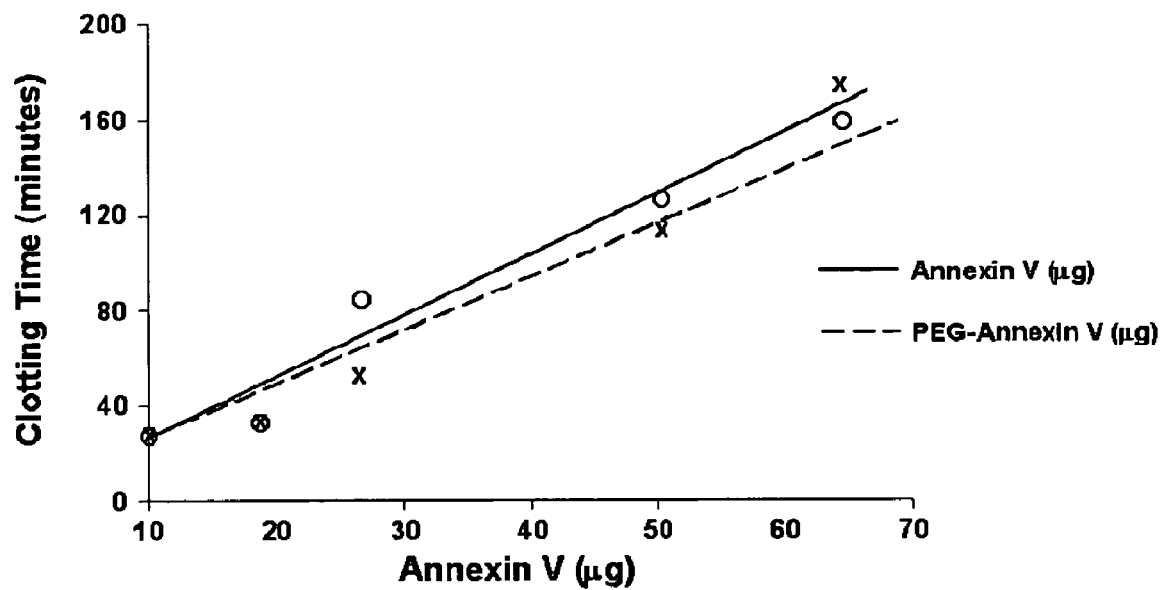
FIG. 6 is a plot of clotting time of an in vitro clotting assay comparing the anticoagulant potency of recombinant human annexin V and pegylated recombinant human annexin V.

Anti-Coagulation Assays. Prolongation of the clotting time (activated partial thromboplastin time) induced by annexin V and pegylated annexin V were compared. Activated partial thromboplastin times were assayed with citrated normal pooled plasma as described in Fritsma, 1989. Using different concentrations of annexin V and pegylated annexin V, produced as described above, dose-response curves for prolongation of clotting times were obtained. Results are shown in FIG. 6, a plot of clotting time versus annexin V and pegylated annexin V dose. As shown in the figure, the anticoagulant potency of the recombinant human annexin V and the pegylated recombinant human annexin V are substantially equivalent. The small difference observed is attributable to the change in molecular weight after pegylation. This experiment validates the assertion made herein that pegylation of annexin V can be achieved without significantly reducing its antithrombotic effects.

Example 4

The affinities of recombinant annexin V (AV) and recombinant annexin V homodimer (DAV, Diannexin) for PS on the surface of cells were compared. To produce cells with PS exposed on their surfaces, human peripheral red blood cells (RBCs) were treated with a $Ca^{2+}$ ionophore (A23187). The phospholipid translocase (flipase), which moves PS to the inner leaflet of the plasma membrane bilayer, was inactivated by treatment with N-ethyl maleimide (NEM), which binds covalently to free sulfhydryl groups. Raising intracellular $Ca^{2+}$ activates the scramblase enzyme, thus increasing the amount of PS in the outer leaflet of the plasma membrane bilayer.

Washed human RBCs were resuspended at 30% hematocrit in K-buffer (80 mM KCl, 7 mM NACl, 10 mM HEPES, pH 7.4). They were incubated for 30 minutes at 37° C. in the presence of 10 mM NEM to inhibit the flipase. The NEM-treated cells were washed and suspended at 16% hematocrit in the same buffer with added 2 mM $CaCl_2$. The scramblase enzyme was activated by incubation for 30 minutes at 37° C. with A23187 (final concentration 4 µM). As a result of this procedure, more than 95% of the RBCs had PS demonstrable on their surface by flow cytometry.

Recombinant AV and DAV were biotinylated using the FluReporter protein-labeling kit (Molecular Probes, Eugene Oreg.). Biotin-AV and biotin-DAV conjugates were visualized with R-phycoerythrin-conjugated streptavidin (PE-SA) at a final concentration of 2 µg/ml. Flow cytometry was performed on a Becton Dickinson FACScaliber and data were analyzed with Cell Quest software (Becton Dickinson, San Jose Calif.).

No binding of AV or DAV was detectable when normal RBCs were used. However, both AV and DAV were bound to at least 95% of RBCs exposing PS. RBCs exposing PS were incubated with various amounts of AV and DAV, either (a) separately or (b) mixed in a 1:1 molar ratio, before addition of PE-SA and flow cytometry. In such mixtures, either AV or DAV was biotinylated and the amount of each protein bound was assayed as described above. The experiments were controlled for higher biotin labeling in DAV than AV.

Representative results are shown in FIG. 2. In this set of experiments, RBCs exposing PS were incubated with (a) 0.2 µg of biotinylated DAV (FIG. 2A); (b) 0.2 µg of biotinylated DAV (FIG. 2B); (c) 0.2 µg of biotinylated AV and 0.2 µg nonbiotinylated DAV; and (d) 0.2 µg of biotinylated DAV and 0.2 µg nonbiotinylated AV (FIG. 2D). Comparing FIG. 2B and FIG. 2D shows that the presence of 0.2 µg of nonbiotinylated AV had no effect on the binding of biotinylated DAV. However, comparing FIG. 2A and FIG. 2C shows that the presence of 0.2 µg of nonbiotinylated DAV strongly reduced the amount of biotinylated AV bound to PS-exposing cells. These results indicate that DAV and AV compete for the same PS-binding sites on RBCs, but with different affinities; DAV binds to PS that is exposed on the surface of cells with a higher affinity than does AV.

Example 5

A cell-binding assay was established using known amounts of annexin V monomer (AV) and dimer (DAV) added to mouse serum. RBCs with externalized PS, as described above, were incubated with serum containing dilutions of AV and DAV. After washing, addition of labeled streptavidin and washing again, AV and DAV bound to the RBCs were assayed by flow cytometry. No binding was detectable when RBCs without externalized PS were used. Concentrations of AV and DAV in mouse serum, assayed by cell binding, were highly correlated with those determined by independent ELISA assays. Hence, AV and DAV in mouse plasma are not bound to other plasma proteins in a way that impairs their capacity to interact with externalized PS on cell surfaces. These observations validated the application of the cell-binding assay to compare the survival of AV and DAV in the circulation.

Figure 3A:
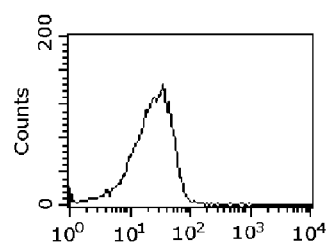
FIGS. 3A-E illustrate the levels of AV or DAV in mouse circulation at various times after injection.
Figure 3B:
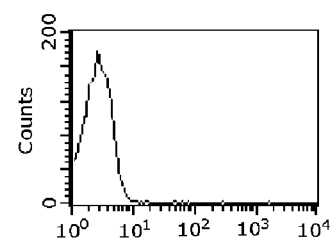
Figure 3C:
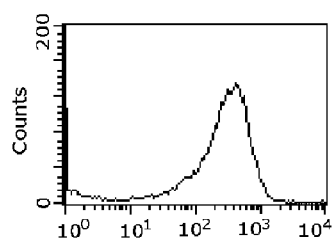
Figure 3D:
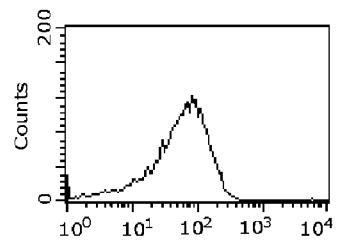
Figure 3E:
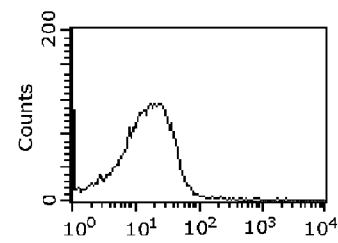

Mice were injected intravenously with AV and DAV, and peripheral blood samples were recovered at several times thereafter. Different mice were used for each time point. Representative results are shown in FIG. 3. Observations in the rabbit (Thiagarajan and Benedict, Circulation 96: 2339, 1977), cynomolgus monkey, (Römisch et al., Thrombosis Res. 61: 93, 1991) and humans (Kemerink et al., J. Nucl. Med. 44: 947, 2003) show that AV has a short half-life in the circulation (7 to 24 minutes, respectively), with a major loss into the kidney. Consistent with these reports, 20 minutes after injection of AV into the mouse, virtually none was detectable in the peripheral blood (FIG. 3B). However, even 120 minutes after intravenous injection of DAV into mice, substantial amounts of the protein were detectable in the circulation (FIG. 3E). Thus dimerization of annexin V increases its survival in the circulation and hence the duration of its therapeutic efficacy.

Example 6

The inhibitory effects of annexin V (AV) and the annexin V homodimer (DAV) on the activity of human sPLA$_2$ (Cayman, Ann Arbor Mich.) were compared. PS externalized on RBCs treated with NEM and A23187, as described above, was used as the substrate. In control cells, AV and DAV were found to bind to PS-exposing RBCs as demonstrable by flow cytometry. Incubation of the PS-exposing cells with sPLA$_2$ removes PS, so that the cells no longer bind annexin. If the PS-exposing cells are treated with AV or DAV before incubation with PLA$_2$, the PS is not removed. The cells can be exposed to a Ca$^{2+}$-chelating agent, which dissociates AV or DAV from PS, and subsequent binding of labeled AV reveals the residual PS on cell surfaces. Titration of AV and DAV in such assays shows that both are potent inhibitors of the activity of sPLA$_2$ on cell-surface PS.

The inhibition of phospholipase is also demonstrable by another method. Activity of sPLA$_2$ releases lysophosphatidylcholine (LPS), which is hemolytic. It is therefore possible to compare the inhibitory effects of AV and DAV on PLA$_2$ in a hemolytic assay. As shown in FIG. 4, both AV and DAV inhibit the action of PLA$_2$, with DAV being somewhat more efficacious. Hemolysis induced after 60 minutes incubation with pPLA$_2$ was strongly reduced in the presence of DAV or AV compared to their absence. From these results it can be concluded that the homodimer of annexin V is a potent inhibitor of secretory PLA$_2$. It should therefore decrease the formation of mediators such as thromboxane A$_2$, as well as lysophosphatidylcholine and lysophosphatidic acid, which are believed to contribute to the pathogenesis of reperfusion injury (Hashizume et al. Jpn. Heart J., 38: 11, 1997; Okuza et al., J. Physiol., 285: F565, 2003).

Example 7

A mouse liver model of warm ischemia-reperfusion injury was used to ascertain whether modified annexins protect against reperfusion injury (RI), compare the activity of annexin V with modified annexins, and determine the duration of activity of modified annexins. The model has been described by Teoh et al. (Hepatology 36:94, 2002). Female C57BL6 mice weighing 18 to 25 g were used. Under ketamine/xylazine anesthesia, the blood supply to the left lateral and median lobes of the liver was occluded with an atraumatic microvascular clamp for 90 minutes. Reperfusion was then established by removal of the vascular clamp. The animals were allowed to recover, and 24 hours later they were killed by exsanguination. Liver damage was assessed by measurement of serum alanine aminotransferase (ALT) activity and histological examination. A control group was subjected to anesthesia and sham laparotomy. To assay the activity of annexin V and modified annexins, groups of 4 mice were used. Each of the mice in the first group was injected intravenously with 25 micrograms of annexin V (AV), each of the second group received 25 micrograms of annexin homodimer (DAV), and each of the third group received 2.5 micrograms of annexin V coupled to polyethylene glycol (PEG-AV, 57 kDa). Controls received saline or the HEPES buffer in which the annexins were stored. In the first set of experiments, the annexins were administered minutes before clamping branches of the hepatic artery. In the second set of experiments, annexins and HEPES were administered 6 hours before initiating ischemia. Representative experimental results are summarized in FIG. 5.

In animals receiving annexin V (AV) just before ischemia, slight protection was observed. By contrast, animals receiving the annexin dimer (DAV) or PEG-AV, either just before or 6 hours before ischemia, showed dramatic protection against RI. Histological studies confirmed that there was little or no hepatocellular necrosis in these groups. The results show that the modified annexins (DAV and PEG-AV) are significantly more protective against ischemia reperfusion injury in the liver than is AV. Furthermore, the modified annexins (DAV and PEG-AV) retain their capacity to attenuate RI for at least 6 hours.

In sham-operated animals, levels of ALT in the circulation were very low. In animals receiving saline just before ischemia, or HEPES 6 hours before ischemia, levels of ALT were very high, and histology confirmed that there was severe hepatocellular necrosis. HEPES administered just before ischemia was found to have protective activity against RI.

Example 8

Thrombosis Study

Six groups of eight rats each were used. The rats for this study were male Wistar rats, weighing about 300 grams (Charles River Nederland, Maastricht, the Netherlands). Animals were housed in macrolon cages, and given standard rodent food pellets and acidified tap water ad lib. Experiments conformed to the rules and regulations set forward by the Netherlands Law on Animal Experiments. Rats were anaesthetized with FFM (Fentanyl/Fluanison/Midazolam), and placed on a heating pad. A cannula was inserted into the femoral vein and filled with saline. The vena cava inferior was isolated, and side branches were closed by ligation or cauterization. A loose ligature was applied around the caval vein below the left renal vein. A second loose ligature was applied 1.5 cm upstream from the first one, above the bifurcation. The test (or control) compound was given intravenously via the femoral vein cannula, and the cannula was then flushed with saline.

Test or control compounds include phosphate-buffered saline 1.0 ml/kg bodyweight (10 min); Phosphate-buffered saline 1.0 ml/kg bodyweight (12 hrs); Diannexin 0.04 mg/kg body weight; Diannexin 0.2 mg/kg body weight; Diannexin 1.0 mg/kg body weight (10 min); Diannexin 1.0 mg/kg body weight (12 hrs); Fragmin 20 aXa U/kg body weight. Ten minutes later (or in two groups: 12 hrs later), recombinant human thromboplastin (0.15 mL/kg) was rapidly injected into the venous cannula, the cannula was flushed with saline, and exactly ten seconds later the downstream ligature near the renal vein was closed. After nine minutes, a citrated venous blood sample was obtained and put on ice.

One minute later (at ten minutes) the upstream ligature near the bifurcation was closed and the thrombus that had formed in the segment was recovered. The thrombus was briefly washed in saline, blotted, and its wet weight was determined. Citrated plasma was prepared by centrifugation for 15 mm at 2000 g at 4° C., and stored at −60° C. for analysis. In the two groups in which thrombus induction took place at 12 hrs after compound injection, a different i.v. injection procedure was used. Rats were anaesthetized with s.c. DDF (Domitor/Dormicum/Fentanyl) and injected via the vein of the penis. Rats were then s.c. given an antidote (Anexate/Antisedan/Naloxon) and kept overnight in their cage.

After insertion of a femoral vein cannula, rats were intravenously injected with Diannexin or Fragmin. At 10 minutes after the intravenous injection of compound (in two groups: at 12 hrs after injection), diluted thromboplastin was injected i.v., and ten seconds later the vena cava inferior ligated. At nine minutes after ligation, blood was collected and citrated plasma was prepared. At ten minutes after ligation, the thrombosed segment was ligated, and the thrombus was recovered and weighed. aPTT (sec) was also measured. At 12 hrs after injection of Diannexin decreased the thrombus weight in a dose-dependent manner. (FIG. 7). At 1 mg/kg, suppression of thrombosis was nearly complete, and not significantly different from that produced by the reference anti-thrombotic drug, the low molecular weight heparin designated Fragmin.

TABLE 1

Effect of Treatment on Thrombus Wet Weight (mg) in the 10-min Thrombosis study.

|  | Saline | Diannexin 1 mg/kg | Diannexin 0.2 mg/kg | Diannexin 0.04 mg/kg | Fragmin 20 aXa U/kg |
|---|---|---|---|---|---|
|  | 21.0 | 1.8 | 0.0 | 15.5 | 0.5 |
|  | 43.8 | 0.0 | 4.3 | 19.6 | 1.5 |
|  | 26.6 | 3.2 | 2.1 | 220 | 4.6 |
|  | 44.5 | 0.5 | 6.0 | 7.5 | 00 |
|  | 17.6 | 3.5 | 3.1 | 10.5 | 4.3 |
|  | 24.0 | 2.7 | 2.8 | 15.6 | 30 |
|  | 10.6 | 4.3 | 5.2 | 16.6 | 0.0 |
|  | 17.8 | 0.5 | 4.7 | 15.3 | 0.0 |
| mean | 25.7 | 2.1 | 3.5 | 15.3 | 1.7 |
| sd | 12.3 | 1.6 | 1.9 | 4.6 | 20 |

By parametric ANOVA; F = 24.48; p < 0.00001
All groups < saline controls (p < 0.01)
By parametric ANOVA of the three Diannexin groups:
F = 4600, p < 0.0001
1 mg = 0.2 mg < 0.04 mg; p < 0.001

Treatment had a significant effect on thrombus weight. Both Fragmin (20 aXa U/kg) and Diannexin (0.04, 0.2 and 1.0 mg/kg) significantly reduced thrombus weight (p<0.0001), see Table 1. For Diannexin, the effect was dose-dependent. The APTT values are shown in Table 2.

TABLE 2

Effect of Treatment on the APTT (seconds) in the 10-Minute Thrombosis Study

|  | Saline | Diannexin 1 mg/kg | Diannexin 0.2 mg/kg | Diannexin 0.04 mg/kg | Fragmin 20 aXa U/kg |
|---|---|---|---|---|---|
|  | 20.7 | 26.1 | 17.6 | 20.7 | n.a. |
|  | 20.0 | 22.0 | 20.8 | 23.5 | 27.1 |
|  | 17.6 | 19.0 | 20.7 | 22.0 | 37.9 |
|  | 21.6 | 16.5 | 20.2 | 21.7 | 19.5 |
|  | 17.5 | 21.5 | 21.3 | 24.9 | 24.2 |
|  | 14.7 | 23.0 | 23.0 | 21.5 | 24.4 |
|  | 20.2 | 22.5 | 19.0 | 19.9 | 29.7 |
|  | 18.7 | 19.3 | 20.4 | 19.4 | 25.0 |
| mean | 18.9 | 21.2 | 20.4 | 21.7 | 26.8 |
| sd | 2.2 | 2.9 | 1.6 | 1.8 | 5.8 |

By parametric ANOVA; F = 6.66; p = 0.0005
Fragmin group > all other groups (p < 0.05)
Saline and Diannexin groups not significantly different Fragmin increased the APPT significantly, compared to all other groups. The APTT was slightly, though significantly increased only in the Fragmin group. The Diannexin groups did not differ from the saline control group.

In the second thrombosis study, in which rats were treated at 12 hrs before the induction of thrombus formation, no significant difference between the saline-injected control group and the Diannexin-treated group was found (Table 3).

TABLE 3

Effect of Treatment on Thrombus Wet Weight (mg) in the 12-hr Thrombosis study.

|  | Saline | Diannexin 1 mg/kg |
|---|---|---|
|  | 16.1 | 22 |
|  | 21.2 | 9.5 |
|  | 17.1 | 13.5 |
|  | 23.2 | 29.0 |
|  | 15.3 | 22.1 |
|  | 19.2 | 18.3 |
|  | 15.6 | 22.3 |
|  | 20.8 | 37.9 |
| mean | 18.6 | 21.8 |
| sd | 3 | 8.8 |

*mean time to thrombus induction: 13.6 hrs
no significant difference by t-test

Thrombus weights in the saline group were also not significantly different from thrombus weights in the saline control group of the 10-min thrombosis study (25.7±12.3 mg, see Table 1). APTT values were not different (not shown).

In summary, the observations show that Diannexin has potent antithrombotic activity in the dose range 0.2 to 1 mg/kg. This effect is no longer demonstrable 12 hours after injection. In the unlikely event that Diannexin produces hemorrhage or any other adverse effect, the patient should soon recover Example 9

Bleeding study: Three groups were studied. Groups of eight rats, as described in Example 8, were used. Rats were anaesthetized with isoflurane, intubated and ventilated, and placed on a heating pad. A cannula was inserted into the femoral vein, and filled with saline. Test or control compounds were i.v. injected via the cannula, and the cannula was then flushed with saline. Test or control compound were phosphate-buffered saline 1.0 ml/kg bodyweight; Diannexin 5.0 mg/kg body weight; Fragmin 140 aXa U/kg body weight.

At 10 min after injection of test compound, the rat tail was put in a horizontal position, and then transected at a defined fixed distance from the tail by scissors. Subsequently, bleeding from the tail was determined by gently blotting-off all blood protruding from the tail by filter paper. The time when bleeding stopped was determined. Any was noted. The experiment was terminated at 30 min after tail transection. Just prior to the end of the experiment, a citrated blood sample was obtained from the cannula. Citrated plasma was prepared by centrifugation for 15 min at 2000 g at −4° C., and stored at −60° C. for analysis. The filter papers were extracted in 20 ml of 10 mM phosphate buffer (pH=7.8), containing 0.05% Triton X-100®. The amount of blood lost was determined by measuring the hemoglobin content of the phosphate buffer (potassium cyanide 1 potassium ferricyanide procedure of Drabkin). Body weight (Table 3) did not differ between groups by parametric ANOVA. Treatment by either Diannexin (mg/kg) 140 U/kg) approximately doubled bleeding time (FIG. 9, Table 3), although these effects were only borderline significant (nonparametric; ANOVA; KW=5.72, p=0.057). Blood loss (FIG. 10, Table 4) was slightly increased in the Diannexin group, and immediately doubled in the Fragmin group, compared to the control group.

TABLE 4

Bleeding times and Blood Loss in the Tail Bleeding Study

| rat # | primary bleeding time (min) | Secondary bleeding (min) | blood loss (mL) |
|---|---|---|---|
| SALINE GROUP | | | |
| 1 | 2.5 | # | 0.049 |
| 2 | 30.0 | # | 0.400 |
| 3 | 17.67 | # | 0.58 |
| 4 | 110 | 5.5 | 0.035 |
| 5 | 30.0 | # | 0.384 |
| 6 | 10 | # | 0.001 |
| 7 | 7.5 | 2.0 | 0.009 |
| 8 | 8.67 | # | 0.034 |
| mean | 13.5 | | 0.19 |
| sd | 11.4 | | 0.23 |
| median | 9.8 | | 0.042 |
| DIANNEXIN GROUP | | | |
| 1 | 30.0 | # | 0.257 |
| 2 | 16.16 | # | 0.016 |
| 3 | 300 | # | 0.022 |
| 4 | 180 | 10.0 | 0.098 |
| 5 | 30.0 | # | 0.263 |
| 6 | 17.0 | 10.0 | 1.868 |
| 7 | 30.0 | # | 0.107 |
| 8 | 30.0 | # | 0.037 |
| mean | 25.1 | | 0.33 |
| sd | 6.7 | | 0.63 |
| median | 30 | | 0.104 |
| FRAGMIN GROUP | | | |
| 1 | 12.0 | 12.0 | 0.034 |
| 2 | 9.0 | 8.67 | 0.069 |
| 3 | 30.0 | # | 0.263 |
| 4 | 30.0 | # | 0.093 |
| 5 | 15.0 | # | nd |
| 6 | 30.0 | # | 1.846 |
| 7 | 30.0 | # | 1.520 |
| 8 | 30.0 | # | 0.213 |
| mean | 23.3 | | 0.58 |
| sd | 9.5 | | 0.77 |
| median | 30 | | 0.213 |

These differences were, however, not significant (non-parametric ANOVA, p=0.490). The APTT values are shown in Table 5 and in FIG. 11.

TABLE 5

Effect of Treatment on the APTT (seconds) in the Tail Bleeding

| | Saline | Diannexin 5 mg/kg | Fragmin 20 aXa U/kg |
|---|---|---|---|
| | 24.3 | 26.3 | 46.6 |
| | 17.8 | 27.0 | 32.1 |
| | 17.3 | 24.1 | 62.9 |
| | 16.5 | 25.5 | 69.8 |
| | 19.9 | 27.7 | 69.1 |
| | 20.3 | 25.1 | 52.4 |
| | 21.4 | 21.0 | 45.7 |
| | 21.9 | 23.2 | 56.5 |
| mean | 19.9 | 25.2 | 54.4 |
| sd | 2.6 | 2.2 | 12.9 |

Figure 11:
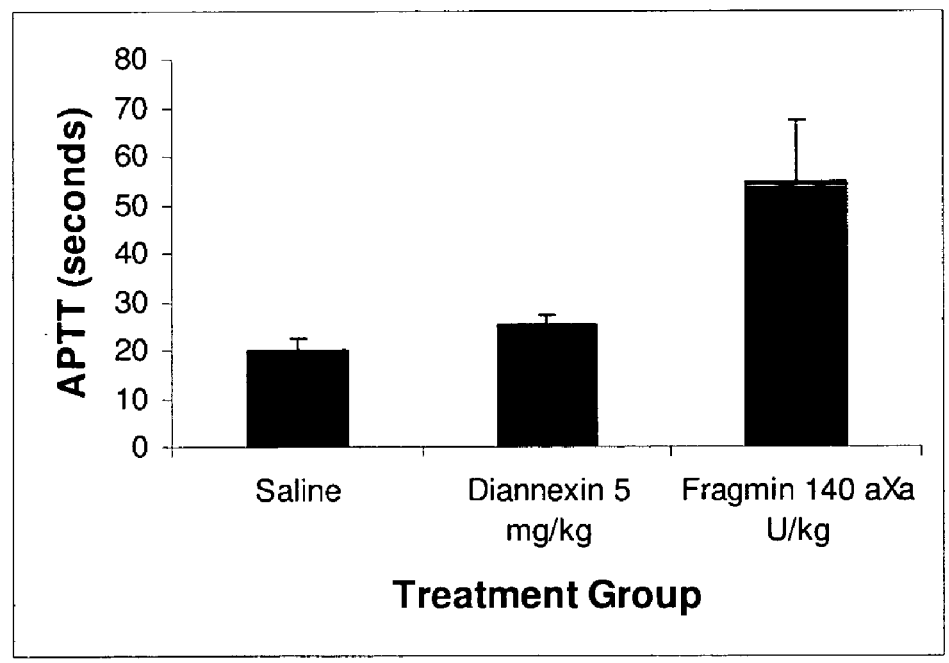
FIG. 11 shows APTT in the three groups of the tail bleeding study (mean±sd; n=8).

Fragmin approximately doubled the APTT, while the APTT in the Diannexin group did not differ from the saline control group (FIG. 11).

Blood loss and the aPTT were approximately twice as large in the Fragmin group as in the Diannexin group in the tail bleeding study. At 5.0 mg/kg i.v. Diannexin induced bleeding from a transected rat tail, though less blood was lost than after injection of 140 aXa U/kg of Fragmin.

Example 10

Clearance study. Rats were injected with radiolabeled Diannexin, blood samples were obtained at 5, 10, 15, 20, 30, 45, and 60 min and 2, 3, 4, 8, 16 and 24 hrs, and blood radioactivity was determined to construct a blood disappearance curve. (FIG. 12) Disappearance of Diannexin from blood could be described by a two-compartment model, with about 75-80% disappearing in the α-phase (t/2 about 10 min), and 15-20% in the β-phase (t/2 about 400 min). Clearance could be described by a two-compartment model, with half-lives of 9-14 min and 6-7 hrs, respectively. Two experiments were performed, each with three male Wistar rats (300 gram). Diannexin was labelled with $^{125}I$ by the method of Macfarlane, and the labeled protein was separated from free Sephadex G-50. After injection of NaI (5 mg/kg) to prevent thyroid uptake of label, about $8\times10^6$ cpm (50 μL of protein solution diluted to 0.5 mL with saline) were injected via a femoral vein catheter (rats 1 and 2) or via the vein of the penis (rat 3). At specified times thereafter (see Table below), blood samples (150 μL) were obtained from a tail vein and 100 μL was counted. After the last blood sample, rats were sacrificed by Nembutal i.v., and (pieces of) liver, lung, heart, spleen and kidneys were collected for counting.

The β-phase parameters were calculated from the data collected between 45 min and 24 hrs. The α-phase parameters were then calculated from the data between 5 and 45 min by the subtraction method. The blood radioactivity curves were analysed by a two-compartment model, using the subtraction method. The linear correlation coefficients for the α- and the β-phase were −0.99 and −0.99 in experiment 1, and −0.95 and −0.96 in experiment 2. The clearance parameters are shown in Table 6.

TABLE 6

Diannexin clearance parameters.

| | Experiment 1 | Experiment 2 |
|---|---|---|
| t/2 alpha phase | 9.2 min | 14.1 min |
| t/2 beta phase | 385 min | 433 min |

TABLE 6-continued

Diannexin clearance parameters.

| | Experiment 1 | Experiment 2 |
|---|---|---|
| % in alpha phase | 85% | 79% |
| % in beta phase | 15% | 21% |
| Isotype recovery in blood (%) | 89% | 52% |

Figure 15A:
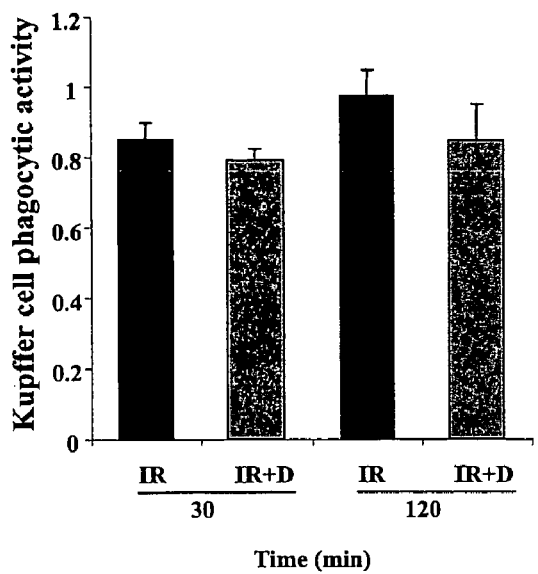
FIG. 15A shows phagocytic activity of Kupffer cells during ischemia-reperfusion injury with and without diannexin for periportal sinusoids.
Figure 15B:
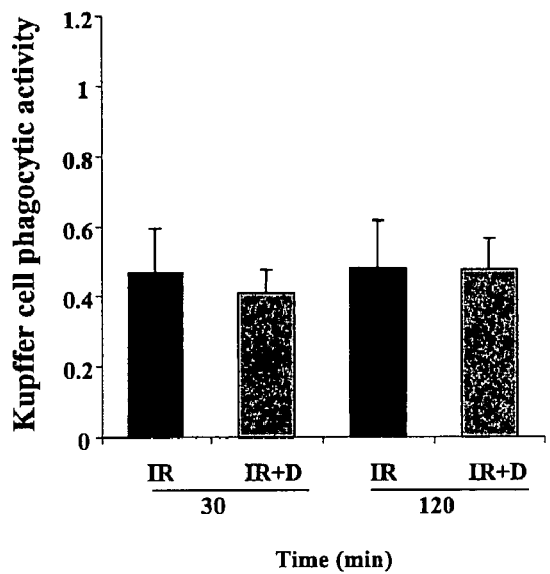
FIG. 15B shows phagocytic activity of Kupffer cells during ischemia-reperfusion injury with and without diannexin for centrilobular sinusoids.
Figure 16:
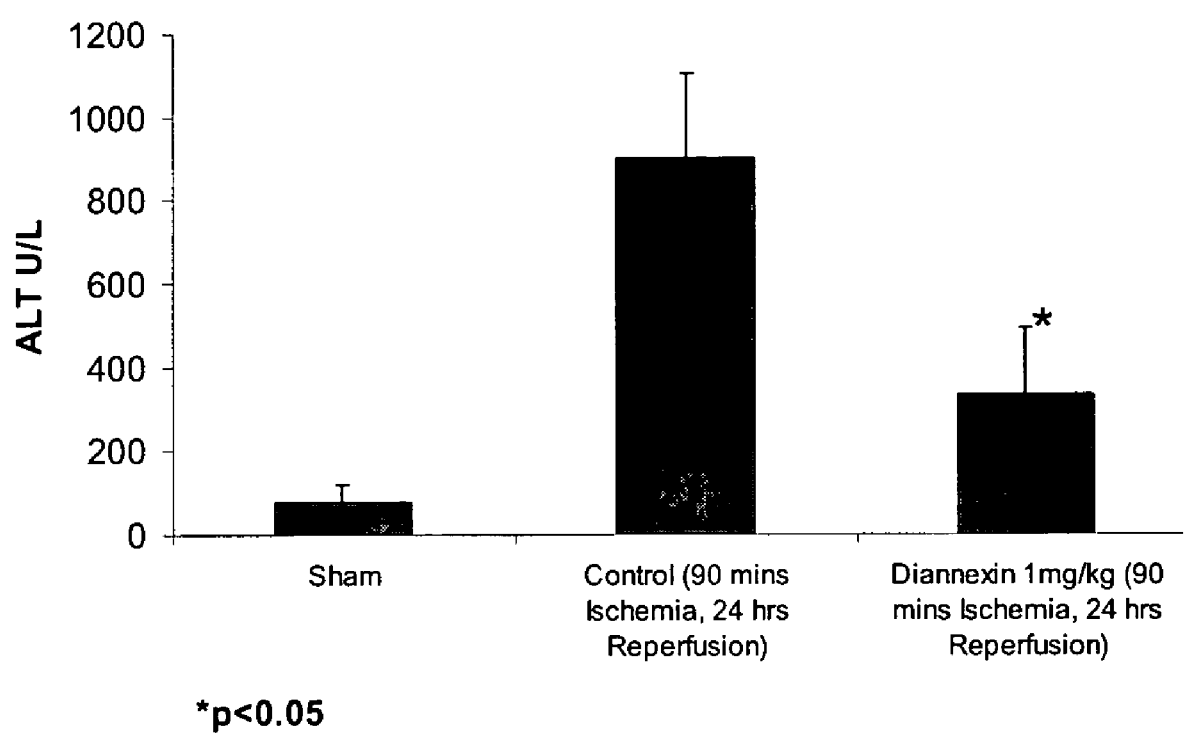
FIG. 16 shows protection by diannexin in ischemia-reperfusion injury in steatotic mice.

FIGS. 15 and 16 show the clearance curves with the alpha- and beta-phases superimposed. In Table 7 are shown the cpm recovered in lung, heart, liver spleen and kidneys (after digestion of the tissues). Of note is the high number of counts in the lung at 2 hrs after Diannexin injection.

TABLE 7

Radioactivity Recovered in Selected Tissues at 2, 8 and 24 hours after injection of $^{125}$I-Diannexin.

| | cpm/tissue | | | % of total counts | | |
|---|---|---|---|---|---|---|
| | at 2 hrs | at 8 hrs | at 24 hrs | at 2 hrs | at 8 hrs | at 24 hrs |
| Exp 1 | | | | | | |
| lung | 166740 | 41622 | 4228 | 28 | 16 | 5 |
| spleen | 82425 | 15211 | 4074 | 14 | 6 | 5 |
| heart | 22582 | 11144 | 1610 | 4 | 4 | 2 |
| liver | 181832 | 85359 | 19730 | 30 | 33 | 24 |
| kidneys | 151858 | 108241 | 53046 | 25 | 41 | 64 |
| sum | 605437 | 261577 | 82688 | 100 | 100 | 100 |
| % of 2 hrs | 100 | 43 | 14 | | | |
| Exp 2 | | | | | | |
| lung | 242130 | 12495 | 4025 | 47 | 8 | 6 |
| spleen | 55377 | 11466 | 5019 | 11 | 7 | 7 |
| heart | 14966 | 8127 | 1645 | 3 | 5 | 2 |
| liver | 37628 | 7152 | 1642 | 7 | 5 | 2 |
| kidneys | 168560 | 114030 | 60774 | 32 | 74 | 83 |
| sum | 518661 | 153270 | 73105 | 100 | 100 | 100 |
| % of 2 hrs | 100 | 30 | 14 | | | |

Example 11

Studies were undertaken to confirm the pathogenesis of ischemia-reperfusion injury (IRI) and mode of action of Diannexin. According to the hypothesis of the pathogenesis of ischemia-reperfusion injury which is part of the present invention, during ischemia, phosphatidylserine (PS) becomes accessible on the luminal surface of endothelial cells (EC) in the hepatic microvasculature. During the reperfusion phase leukocytes and platelets become attached to PS on the surface of EC the surface of EC and reduce blood flow in the hepatic microcirculation. Diannexin binds to PS on the surface of EC and decreases the attachment of leukocytes and platelets to them. By this mechanism Diannexin maintains blood flow in the hepatic microcirculation and thereby attenuates ischemia-reperfusion injury.

Figure 12A:
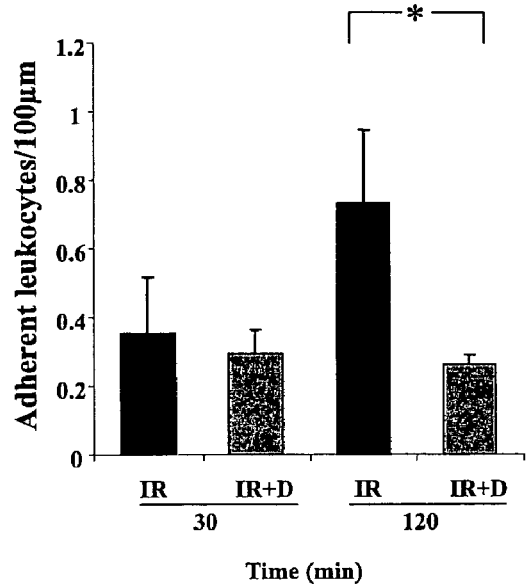
FIG. 12A shows attachment of leukocytes to endothelial cells during ischemia-reperfusion injury with and without diannexin for periportal sinusoids.
Figure 12B:
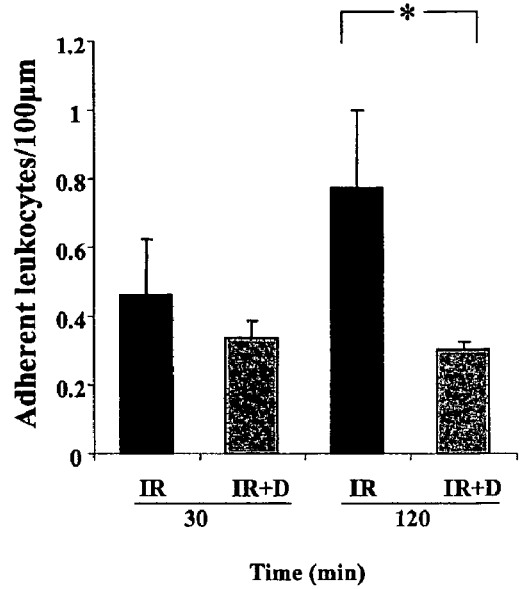
FIG. 12B shows attachment of leukocytes to endothelial cells during ischemia-reperfusion injury with and without diannexin for centrilobular sinusoids.
Figure 13A:
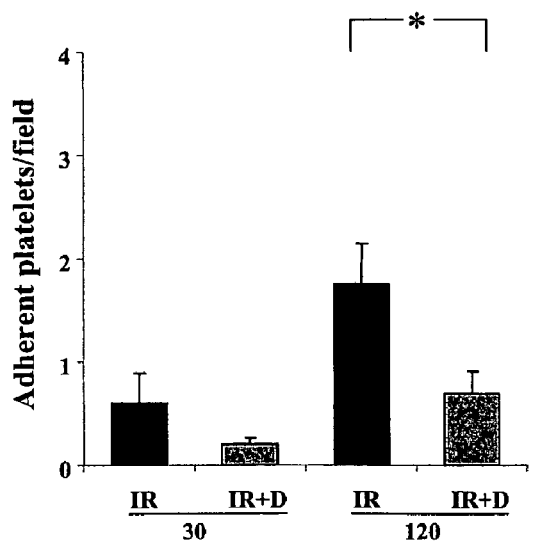
FIG. 13A shows attachment of platelets to endothelial cells during ischemia-reperfusion injury with and without diannexin for periportal sinusoids.
Figure 13B:
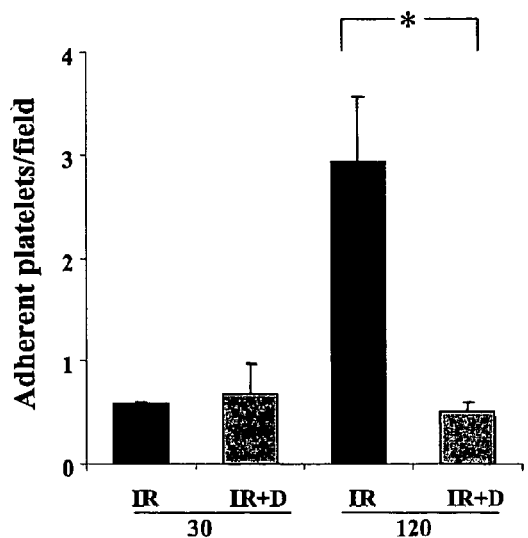
FIG. 13B shows attachment of platelets to endothelial cells during ischemia-reperfusion injury with and without diannexin for centrilobular sinusoids.
Figure 14A:
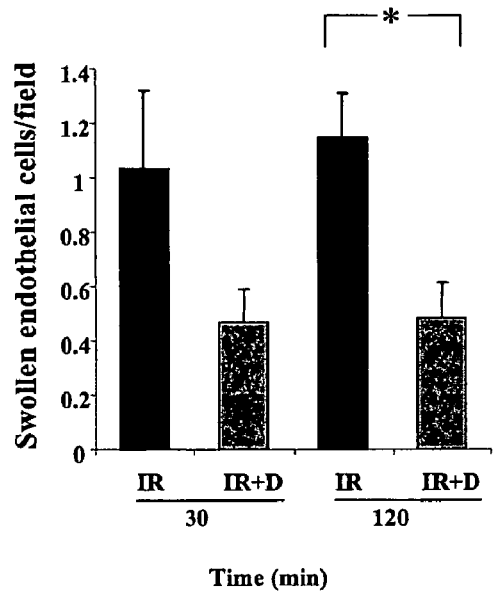
FIG. 14A shows swelling of endothelial cells during ischemia-reperfusion injury with and without diannexin for periportal sinusoids.
Figure 14B:
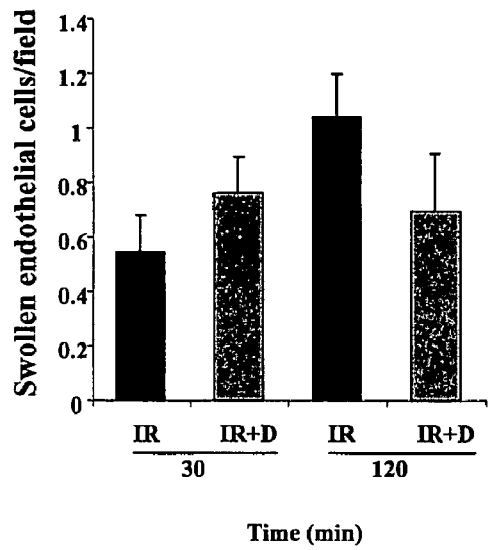
FIG. 14B shows swelling of endothelial cells during ischemia-reperfusion injury with and without diannexin for centrilobular sinusoids.

This hypothesis was tested by observing the microcirculation in the mouse liver in vivo using published methods (McCuskey et al., Hepatology 40: 386,2004). As described in example 7, 90 minutes of ischemia was followed by various times of reperfusion. FIGS. 12A and 12B show that during reperfusion many leukocytes become attached to EC in both the periportal and centrilobular areas (IR). Diannexin (1 mg/kg) IV) reduces such attachment in a statistically significant manner (IR+D). FIGS. 13A and 13B show that this is also true of the adherence of platelets to EC during reperfusion. As predicted, EC damage (reflected by swelling) is prominent during reperfusion and is significantly decreased by Diannexin (FIGS. 14A and 14B). Our hypothesis of the mode of action of Diannexin in attenuating ischemia-reperfusion injury is therefore confirmed. As shown in FIGS. 15A and 15B, Diannexin does not influence the phagocytic activity of Kupffer cells in either location. Hence, Diannexin has no effect on this defense mechanism against pathogenic organisms. This finding supports other evidence that Diannexin does not have adverse effects.

Example 12

The efficacy of Diannexin in protection of organs of cold ischemia-warm reperfusion injury was evaluated in a rat liver transplantation model (Sawitzki, B. et al. Human Gene Therapy 13: 1495, 2002). Livers were recovered from adult male Sprague-Dawley rats, perfused with University of Wisconsin solution, kept at 4° C. for 24 hrs and transplanted orthotopically into syngeneic recipients. Under these conditions 60% of untreated recipients died within 48 hours of transplantation, as previously observed in similar experiments. Another 10 recipients of liver grafts were given Diannexin (0.2 mg/kg intravenously) 10 minutes and 24 hrs after transplantation. All these animals survived for more than 14 days, which on the basis of previous experience implies survival unlimited by the operation.

As shown in table 8, levels of the liver enzyme alanine aminotransferase (ALT) in the circulation of untreated recipients at 6 hrs and 24 hrs after transplantation were significantly higher than in Diannexin-treated recipients. Diannexin-mediated cytoprotection was confirmed by histological examination of the livers in transplant recipients. By 7 days after transplantation ALT levels were back to the normal range in all recipients.

In second group of 10 recipients Diannexin was used in a different way. Rat livers were obtained from Sprague-Dawley donors and perfused ex vivo with University of Wisconsin Solution containing Diannexin (0.2 mg/liter) twice, before 24 hr of 4° cold storage and just before orthotopic transplantation. No Diannexin was given post-transplant to these recipients, all of which survived >14 days. Again ALT levels at 6 and 24 hrs were significantly lower than in untreated animals and histological examination showed a substantial difference between the well preserved livers in Diannexin-treated and the partially necrotic livers in control graft recipients.

These observations show that Diannexin markedly attenuates IRI in a cold ischemia-warm reperfusion rat liver model which is similar to the situation in human liver transplantation. Diannexin is equally efficacious when included in the solution used to perfuse the liver ex vivo when administered to recipients of liver grafts shortly after transplantation.

TABLE 8

Serum ALT levels (IU/L) in rat liver graft recipients (mean ± SD)

| | Untreated controls | Diannexin treated | P value |
|---|---|---|---|
| 6 hrs | 1345 ± 530 | 267 ± 110 | <0.001 |
| 1 day | 4031 ± 383 | 620 ± 428 | <0.001 |
| 7 days | 99 ± 31 | 72 ± 8 | >0.5 |

Example 12

As an experimental model of human steatotic livers mice were made steatotic by feeding them a diet containing 20% fat for 8 weeks. Groups of 5 female C57BL6 mice weighing 18 to 25 g were subjected to 90 minutes ischemia and 24 hours reperfusion. One group of recipients received 1 mg/kg Diannexin just before the commencement of reperfusion. As shown by the liver enzyme levels in FIG. 16, Diannexin provided highly significant protection against IRI.

Example 13

This experiment was undertaken to ascertain whether Diannexin can protect the liver from IRI when administration of the protein is delayed until after the commencement of reperfusion. Our standard protocol for the mouse liver warm IRI was used: adult female C57BL6 mice, 90 minutes ischemia and 24 hrs reperfusion. Endpoints were serum ALT levels and liver pathology at 24 hours. Diannexin (1 mg/kg) was administered 10 minutes and 60 minutes after commencement of reperfusion. As shown in table 9, both of these procedures significantly decreased ALT levels, and protective effects were confirmed by liver histology. These observations show that Diannexin administration can be delayed until at least 1 hour after the initiation of reperfusion, implying that endothelial changes during the first hour are reversible. The findings also show that administration of Diannexin a few minutes after re-establishing the circulation in recipients of transplanted organs should attenuate IRI.

TABLE 9

| Effect of Diannexin (1 mg/kg) Administration during Reperfusion | | |
|---|---|---|
| Time after commencement of reperfusion | Serum ALT mean ± s.d. | Probability |
| 0 (untreated control) | 840 ± 306 | |
| 10 minutes | 153 ± 83 | p < 0.05 |
| 60 minutes | 255 ± 27 | p < 0.05 |

What is claimed is:

1. A method of protecting an organ or a tissue susceptible to ischemia reperfusion injury (IRI), comprising administering to a patient who is a recipient of an organ transplant a composition comprising an isolated annexin dimer at least 95% identical to a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3 and SEQ ID NO: 15-linker-SEQ ID NO: 12, wherein the linker is at least one glycine-serine sequence, and whereby said administering protects said organ and tissue.

2. The method of claim 1, wherein said composition is administered in an intravascular dose of 10 to 1000 μg/kg.

3. The method of claim 2, wherein said composition is administered in an intravascular dose of 100 to 500 μg/kg.

4. The method of claim 1, wherein said composition is administered to the recipient patient during the transplantation.

5. The method of claim 1, wherein said annexin dimer is selected from the group consisting of SEQ ID NO: 6, SEQ ID NO: 19, SEQ ID NO: 27, SEQ ID NO:23, SEQ ID NO: 3-linker-SEQ ID NO: 3, SEQ ID NO: 12-linker-SEQ ID NO: 12, and SEQ ID NO: 15-linker-SEQ ID NO: 15, SEQ ID NO: 3-linker-SEQ ID NO: 12, SEQ ID NO: 3-linker-SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3, and SEQ ID NO: 15-linker-SEQ ID NO: 12.

6. A method of protecting an organ or a tissue susceptible to ischemia reperfusion injury (IRI), comprising administering to a patient who is a recipient of an organ transplant a composition comprising an isolated annexin dimer at least 95% identical to a protein selected from the group consisting of SEQ ID NO: 6, SEQ ID NO: 26, SEQ ID NO: 27, SEQ ID NO: 19, SEQ ID NO: 23, SEQ ID NO: 3-linker-SEQ ID NO: 12, SEQ ID NO: 3-linker-SEQ ID NO: 15, SEQ ID NO: 12 -linker-SEQ ID NO: 15, SEQ ID NO: 12 -linker-SEQ ID NO: 3, SEQ ID NO: 15-linker-SEQ ID NO: 3 and SEQ ID NO: 15-linker-SEQ ID NO: 12, wherein the linker is at least one glycine-serine sequence, and whereby said administering protects said organ and tissue.

7. A method of protecting organ or tissue transplants susceptible to ischemia reperfusion injury (IRI), comprising contacting said transplant with a preservation fluid for perfusion and storage, wherein said preservation fluid comprises an isolated annexin dimer at least 95% identical to a protein selected from the group consisting of SEQ ID NO: 6, SEQ ID NO: 19, SEQ ID NO: 27, SEQ ID NO:23, SEQ ID NO: 3-linker-SEQ ID NO: 3, SEQ ID NO: 12 -linker-SEQ ID NO: 12, and SEQ ID NO: 15-linker-SEQ ID NO: 15, SEQ ID NO: 3-linker-SEQ ID NO: 12, SEQ ID NO: 3-linker -SEQ ID NO: 15, SEQ ID NO: 12-linker-SEQ ID NO: 15, SEQ ID NO: 12-linker-SEQ ID NO: 3, SEQ ID NO: 15-linker-SEQ ID NO: 3, and SEQ ID NO: 15-linker-SEQ ID NO: 12: wherein the linker is at least one glycine-serine sequence, and whereby said contacting protects said organ and tissue transplants.

8. The method of claim 7, wherein said preservation fluid comprises an isolated annexin dimer in a concentration of 0.1 to 1 mg/l.

* * * * *

UNITED STATES PATENT AND TRADEMARK OFFICE
CERTIFICATE OF CORRECTION

PATENT NO. : 7,635,676 B2
APPLICATION NO. : 11/267837
DATED : December 22, 2009
INVENTOR(S) : Anthony Allison It is certified that error appears in the above-identified patent and that said Letters Patent is hereby corrected as shown below:

Column 111, line 48 should be corrected to read "NO: 15-linker-SEQ ID NO: 12, wherein the linker has at least".

Column 112, line 45 should be corrected to read "15-linker-SEQ ID NO: 12, wherein the linker has at least one".

Column 112, line 60 should be corrected to read "the linker has at least one glycine-serine sequence, and".

Signed and Sealed this

Twenty-third Day of March, 2010

David J. Kappos
*Director of the United States Patent and Trademark Office*